(12) United States Patent
Sepp et al.

(10) Patent No.: US 8,084,213 B2
(45) Date of Patent: Dec. 27, 2011

(54) SELECTION

(75) Inventors: Armin Sepp, Cambridge (GB); Andrew Griffiths, Strasbourg (FR)

(73) Assignee: Domantis Limited (GB)

( * ) Notice: Subject to any disclaimer, the term of this patent is extended or adjusted under 35 U.S.C. 154(b) by 419 days.

(21) Appl. No.: 11/654,820

(22) Filed: Jan. 17, 2007

(65) Prior Publication Data
US 2009/0176209 A1 Jul. 9, 2009

Related U.S. Application Data

(63) Continuation of application No. PCT/GB2005/003243, filed on Aug. 19, 2005.

(30) Foreign Application Priority Data

Aug. 20, 2004 (GB) .................................. 048651.6

(51) Int. Cl.
| | |
|---|---|
| C12Q 1/68 | (2006.01) |
| C12P 21/08 | (2006.01) |
| C12P 21/00 | (2006.01) |
| C12N 15/00 | (2006.01) |
| C12N 5/00 | (2006.01) |
| A61K 38/16 | (2006.01) |
| C07K 14/00 | (2006.01) |
| C07H 21/04 | (2006.01) |

(52) U.S. Cl. ......... 435/6.19; 435/69; 435/320; 435/325; 430/350; 430/358; 430/387.3; 536/23.53

(58) Field of Classification Search ...................... None
See application file for complete search history.

(56) References Cited

U.S. PATENT DOCUMENTS
5,830,663 A * 11/1998 Embleton et al. ................ 435/6
7,153,666 B2 * 12/2006 Yuan et al. ...................... 435/23
7,455,988 B2 * 11/2008 Fandl et al. ................. 435/69.1

FOREIGN PATENT DOCUMENTS
| | | |
|---|---|---|
| WO | PCT/US92/08879 A1 | 4/1996 |
| WO | PCT/GB98/01889 | 1/1999 |
| WO | PCT/GB98/02630 | 3/1999 |
| WO | PCT/GB2003/003860 | 3/2004 |

OTHER PUBLICATIONS

Kropinski (Journal of Bacteriology, 2000, vol. 182, pp. 6472-6481).*
Abstract of Vershon et al (Journal of Biological Chemistry, 1987, vol. 195, pp. 323-331).*
Abstract of Youderian et al (Cell, 1982, vol. 30, pp. 843-853).*
Robinson et al (Biochemistry, 1996, vol. 35, pp. 109-116).*
Clark (Protein Engineering of Antibody Molecules for Prophylactic and Therapeutic Applications in Man, 1993, pp. 4-5).*
"Anti-HA High Affinity Rat monoclonal antibody (clone 3F10)," Catalog Nos. 11 867 423 001 (50 µg) and 11 867 431 001 (500 µg), Roche, 3 pages (2008).
"Anti-HA High Affinity (3F10) for immunoblotting and immunoprecipitating epitope-tagged proteins," *Biochemica*, No. 2, 1 page (1997).
Robert E. Speight et al., A New Plasmid Display Technology for the in vitro Selection of Functional Phenotype-Genotype Linked Proteins, Chemistry & Biology 8 (2001) 951-965, XP-002217504.
Duncan P. McGregor et al., External Surface Display of Proteins Linked to DNA-Binding Domains, Analytical Biochemistry 294, 108-117 (2001).
Richard Odegrip et al., CIS Display: In Vitro Selection of Peptides From Libraries of Protein-DNA Complexes, PNAS, 2806-2810, Mar. 2, 2004 vol. 101, No. 9.
Masato Yonezawa et al, DNA display for in Vitro Selection of Diverse Peptide Libraries, Nucleic Acids Research, 2003, vol. 31, No. 19.
Armin Sepp, et al., Microbead Display by In Vitro Compartmentalisation; Selection for Binding Using Flow Cytometry, FEBS Letters 532 (2002) 455-458.
Dan S. Tawfik et al, Man-made Cell-like Compartments for Molecular Evolution, Nature Biotechnology, vol. 16, Jul. 1998, 652-656.

* cited by examiner

*Primary Examiner* — Karen Canella
(74) *Attorney, Agent, or Firm* — William Peter Long; William T. Han

(57) ABSTRACT

The present invention to a nucleotide sequence encoding one or more Arc DNA binding domains, one or more Arc DNA binding sites and at least one polypeptide domain.

44 Claims, 30 Drawing Sheets

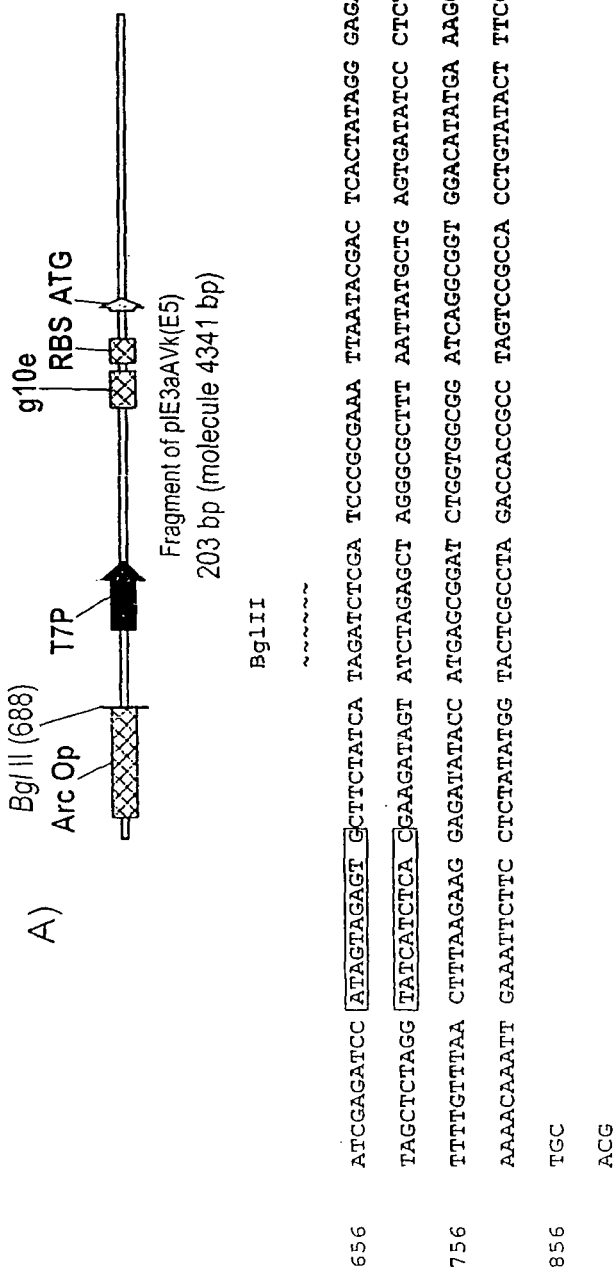

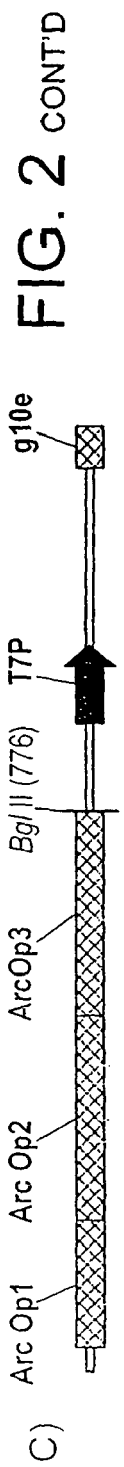

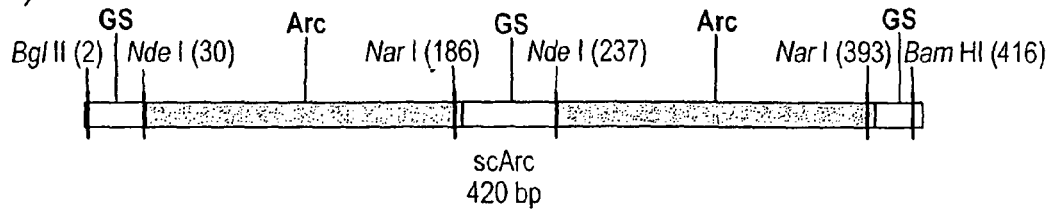

B)

```
       BglII                           NdeI
       ~~~~~~                          ~~~~~~

R  S  G  G  G  S  G  G  G  H  M  K  G  M  S  K  M  P  Q  F  N  L  R  W  P  R  E
  1    AGATCTGGTGGCGGATCAGGCGGTGGACATATGAAAGGAATGAGCAAAATGCCGCAGTTCAATTTGCGGTGGCCTAGAGAA

V  L  D  L  V  R  K  V  A  E  E  N  G  R  S  V  N  S  E  I  Y  Q  R  V  M  E  S
  82   GTATTGGATTTGGTACGCAAGGTAGCGGAAGAGAATGGTCGGTCTGTTAATTCTGAGATTTATCAGCGAGTAATGGAAAGC

NarI                                                    NdeI
                         ~~~~~~                                                  ~~~~~~

F  K  K  E  G  R  I  G  A  G  G  G  S  G  G  G  S  G  G  G  S  G  G  H  M  K
  163  TTTAAGAAGGAAGGGCGCATTGGCGCCGGTGGCGGATCAGGCGGTGGATCTGGTGGCGGATCAGGCGGTGGACATATGAAA

G  M  S  K  M  P  Q  F  N  L  R  W  P  R  E  V  L  D  L  V  R  K  V  A  E  E  N
  244  GGAATGAGCAAAATGCCGCAGTTCAATTTGCGGTGGCCTAGAGAAGTATTGGATTTGGTACGCAAGGTAGCGGAAGAGAAT

NarI
                                                                           ~~~~~~

G  R  S  V  N  S  E  I  Y  Q  R  V  M  E  S  F  K  K  E  G  R  I  G  A  G  G  G
  325  GGTCGGTCTGTTAATTCTGAGATTTATCAGCGAGTAATGGAAAGCTTTAAGAAGGAAGGGCGCATTGGCGCCGGTGGCGGA

BamHI
          ~~~~~~

S  G  G  G  S
  406  TCAGGCGGTGGATCC
```

BglII

657 TCGAGATCTCGATCCCGCGAAATTAATACGACTCACTATAGGGAGACCACAACGGTTTCCCTCTAGAAATAATTTTGTTT
658

NcoI    SalI        NotI

M  G  S  T  G  G  A  A  A  G  S  G  G  G  S  G  G  H  M ·

737 AACTTTAAGAAGGAGATATACCATGGGGTCGACCGGCGGCGCGGCCGCAGGATCTGGTGGCGGATCAGGCGGTGGACATA

· K  G  M  S  K  M  P  Q  F  N  L  R  W  P  R  E  V  L  D  L  V  R  K  V  A  E

817 TGAAAGGAATGAGCAAAATGCCGCAGTTCAATTTGCGGTGGCCTAGAGAAGTATTGGATTTGGTACGCAAGGTAGCGGAA

E  N  G  R  S  V  N  S  E  I  Y  Q  R  V  M  E  S  F  K  K  E  G  R  I  G  A  G ·

897 GAGAATGGTCGGTCTGTTAATTCTGAGATTTATCAGCGAGTAATGGAAAGCTTTAAGAAGGAAGGGCGCATTGGCGCCGG

· G  G  S  G  G  G  S  G  G  G  S  G  G  G  H  M  K  G  M  S  K  M  P  Q  F  N  L ·

977 TGGCGGATCAGGCGGTGGATCTGGTGGCGGATCAGGCGGTGGACATATGAAACGAATGAGCAAAATGCCGCAGTTCAATT

R  W  P  R  E  V  L  D  L  V  R  K  V  A  E  E  N  G  R  S  V  N  S  E  I  Y

1057 TGCGGTGGCCTAGAGAAGTATTGGATTTGGTACGCAAGGTAGCGGAAGAGAATGGTCGGTCTGTTAATTCTGAGATTTAT

BamHI

Q  R  V  M  E  S  F  K  K  E  G  R  I  G  A  G  G  G  S  G  G  G  S  Y  P  Y  D ·

1137 CAGCGAGTAATGGAAAGCTTTAAGAAGGAAGGGCGCATTGGCGCCGGTGGCGGATCAGGCGGTGGATCCTATCCGTATGA

XhoI

· V  P  D  Y  A  *

1217 TGTGCCGGATTATGCGTAACTCGAGAGATCCGGTAACAAAGCCCGAAAGGAAGCTGAGTTGGCTGCTGCCACCGCTGAGC

1297 AATAACTAGCATAACCCCTTGGGGCCTCTAAACGGGTCTTGAGGGGTTTTTTGCTGAAAGG

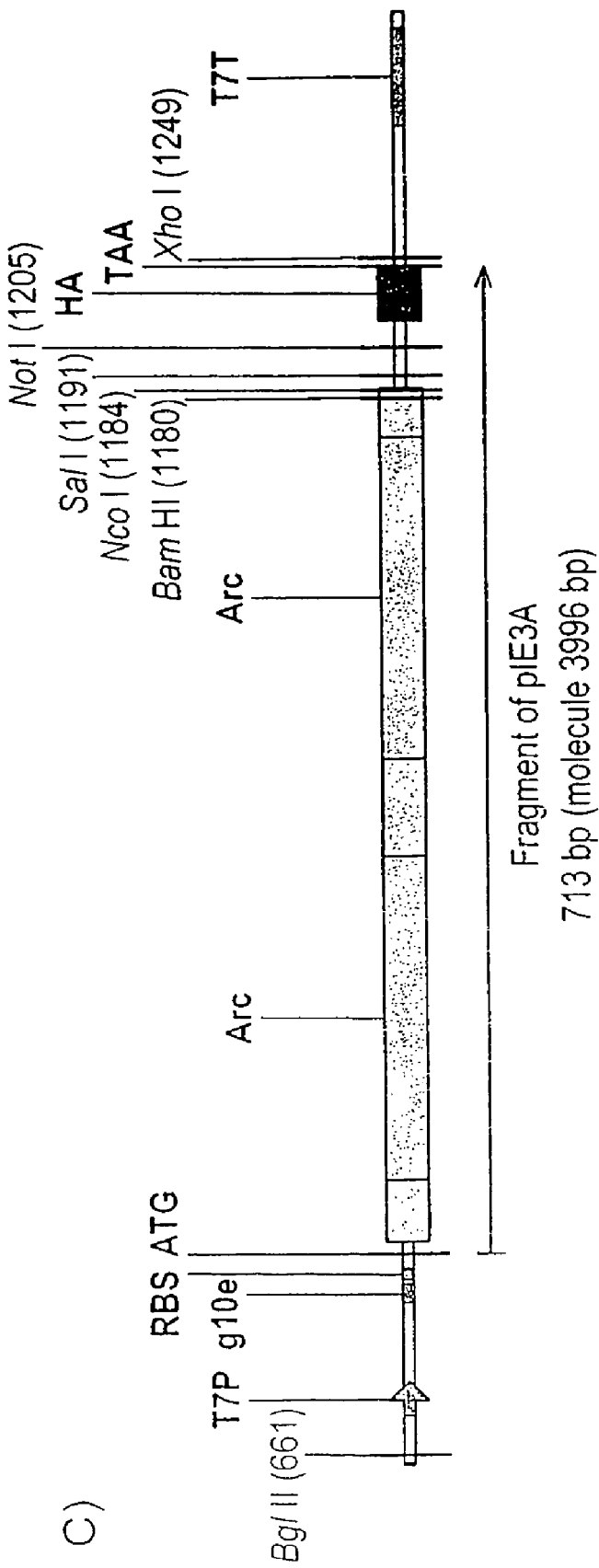

BglII

```
657   TCGAGATCTCGATCCCGCGAAATTAATACGACTCACTATAGGGAGACCACAACGGTTTCCCTCTAGAAATAATTTTGTTT
                              M  S  G  S  G  G  G  S  G  G  G  H  M  K  G  M  S  K  M  P

737   AACTTTAAGAAGGAGATATACCATGAGCGGATCTGGTGGCGGATCAGGCGGTGGACATATGAAAGGAATGAGCAAAATGC
       Q  F  N  L  R  W  P  R  E  V  L  D  L  V  R  K  V  A  E  E  N  G  R  S  V  N

817   CGCAGTTCAATTTGCGGTGGCCTAGAGAAGTATTGGATTTGGTACGCAAGGTAGCGGAAGAGAATGGTCGGTCTGTTAAT
        S  E  I  Y  Q  R  V  M  E  S  F  K  K  E  G  R  I  G  A  G  G  G  S  G  G  G  S

897   TCTGAGATTTATCAGCGAGTAATGGAAAGCTTTAAGAAGGAAGGGCGCATTGGCGCCGGTGGCGGATCAGGCGGTGGATC
        G  G  G  S  G  G  G  H  M  K  G  M  S  K  M  P  Q  F  N  L  R  W  P  R  E  V  L

977   TGGTGGCGGATCAGGCGGTGGACATATGAAAGGAATGAGCAAAATGCCGCAGTTCAATTTGCGGTGGCCTAGAGAAGTAT
        D  L  V  R  K  V  A  E  E  N  G  R  S  V  N  S  E  I  Y  Q  R  V  M  E  S  F

1057  TGGATTTGGTACGCAAGGTAGCGGAAGAGAATGGTCGGTCTGTTAATTCTGAGATTTATCAGCGAGTAATGGAAAGCTTT
                                                NcoI

BamHI          SalI            NotI

K  K  E  G  R  I  G  A  G  G  G  S  G  G  G  S  M  G  S  T  G  A  A  A  R

1137  AAGAAGGAAGGGCGCATTGGCGCCGGTGGCGGATCAGGCGGTGGATCCATGGGGTCGACCGGCGGCGCGGCCGCAAGATC
                                                 XhoI

Y  P  Y  D  V  P  D  Y  A

1217  CTATCCGTATGATGTGCCGGATTATGCGTAACTCGAGAGATCCGGTAACAAAGCCCGAAAGGAAGCTGAGTTGGCTGCTG
1297  CCACCGCTGAGCAATAACTAGCATAACCCCTTGGGGCCTCTAAACGGGTCTTGAGGGGTTTTTTGCTGAAAGG
```

BglII

3862 ATCGAGATCC`ATAGTAGAGTGCTTCTATCAT`AGATCTCGATCCCGCGAAATTAATACGACTCACTATAGGGAGACCACAA

NcoI  SalI

M  G  S  T  D  I  Q  M  T  Q

3942 CGGTTTCCCTCTAGAAATAATTTTGTTTAACTTTAAGAAGGAGATATACCATGGGGTCGACGGACATCCAGATGACCCAG

S  P  S  S  L  S  A  S  V  G  D  R  V  T  I  T  C  R  A  S  Q  S  V  S  S  Y  L

4022 TCTCCATCCTCCCTGTCTGCATCTGTAGGAGACAGAGTCACCATCACTTGCCGGGCAAGTCAGAGCGTTAGCAGCTATTT

N  W  Y  Q  Q  K  P  G  K  A  P  K  L  L  I  Y  L  A  S  R  L  Q  S  G  V  P  S

4102 AAATTGGTATCAGCAGAAACCAGGGAAAGCCCCTAAGCTCCTGATCTATCTTGCATCCCGTTTGCAAAGTGGGGTCCCAT

R  F  S  G  S  G  S  G  T  D  F  T  L  T  I  S  S  L  Q  P  E  D  F  A  T  Y

4182 CAAGGTTCAGTGGCAGTGGATCTGGGACAGATTTCACTCTCACCATCAGCAGTCTGCAACCTGAAGATTTTGCAACTTAC

NotI

Y  C  Q  Q  N  W  W  L  P  P  T  F  G  Q  G  T  K  V  E  I  K  R  A  A  A  G  S

4262 TACTGTCAACAGAATTGGTGGCTGCCTCCTACGTTCGGCCAAGGGACCAAGGTGGAAATCAAACGGGCGGCCGCAGGATC

G  G  G  S  G  G  G  H  M  K  G  M  S  K  M  P  Q  F  N  L  R  W  P  R  E  V  L

13 TGGTGGCGGATCAGGCGGTGGACATATGAAAGGAATGAGCAAAATGCCGCAGTTCAATTTGCGGTGGCCTAGAGAAGTAT

D  L  V  R  K  V  A  E  E  N  G  R  S  V  N  S  E  I  Y  Q  R  V  M  E  S  F

93 TGGATTTGGTACGCAAGGTAGCGGAAGAGAATGGTCGGTCTGTTAATTCTGAGATTTATCAGCGAGTAATGGAAAGCTTT

K  K  E  G  R  I  G  A  G  G  G  S  G  G  G  S  G  G  G  S  G  G  G  H  M  K  G

173 AAGAAGGAAGGGCGCATTGGCGCCGGTGGCGGATCAGGCGGTGGATCTGGTGGCGGATCAGGCGGTGGACATATGAAAG

M  S  K  M  P  Q  F  N  L  R  W  P  R  E  V  L  D  L  V  R  K  V  A  E  E  N  G

253 AATGAGCAAAATGCCGCAGTTCAATTTGCGGTGGCCTAGAGAAGTATTGGATTTGGTACGCAAGGTAGCGGAAGAGAATG

R  S  V  N  S  E  I  Y  Q  R  V  M  E  S  F  K  K  E  G  R  I  G  A  G  G  G

333 GTCGGTCTGTTAATTCTGAGATTTATCAGCGAGTAATGGAAAGCTTTAAGAAGGAAGGGCGCATTGGCGCCGGTGGCGGA

BamHI                              XhoI

S  G  G  G  S  Y  P  Y  D  V  P  D  Y  A  *

413 TCAGGCGGTGGATCCTATCCGTATGATGTGCCGGATTATGCGTAACTCGAGAGATCCGGTAACAAAGCCCGAAAGGAAGC

493 TGAGTTGGCTGCTGCCACCGCTGAGCAATAACTAGCATAACCCCTTGGGGCCTCTAAACGGGTCTTGAGGGGTTTTTTGC

573 TGAAAGG

```
                    BglII
                    ~~~~~
658    CGAGATCC[ATAGTAGAGTGCTTCTATCAT]AGATCTCGATCCCGCGAAATTAATACGACTCACTATAGGGAGACCACAACG
                                                       M  S  G  S  G  G  G  S  G  G  G ·

738    GTTTCCCTCTAGAAATAATTTTGTTTAACTTTAAGAAGGAGATATACCATGAGCGGATCTGGTGGCGGATCAGGCGGTGG
       · H  M  K  G  M  S  K  M  P  Q  F  N  L  R  W  P  R  E  V  L  D  L  V  R  K  V  A ·

818    ACATATGAAAGGAATGAGCAAAATGCCGCAGTTCAATTTGCGGTGGCCTAGAGAAGTATTGGATTTGGTACGCAAGGTAG
       · E  E  N  G  R  S  V  N  S  E  I  Y  Q  R  V  M  E  S  F  K  K  E  G  R  I  G

898    CGGAAGAGAATGGTCGGTCTGTTAATTCTGAGATTTATCAGCGAGTAATGGAAAGCTTTAAGAAGGAAGGGCGCATTGGC
          A  G  G  G  S  G  G  G  S  G  G  G  S  G  G  G  H  M  K  G  M  S  K  M  P  Q  F ·

978    GCCGGTGGCGGATCAGGCGGTGGATCTGGTGGCGGATCAGGCGGTGGACATATGAAAGGAATGAGCAAAATGCCGCAGTT
       · N  L  R  W  P  R  E  V  L  D  L  V  R  K  V  A  E  E  N  G  R  S  V  N  S  E  I ·

1058   CAATTTGCGGTGGCCTAGAGAAGTATTGGATTTGGTACGCAAGGTAGCGGAAGAGAATGGTCGGTCTGTTAATTCTGAGA
                                                                              NcoI
                                                                              ~~~~~

BamHI         SalI
                                                              ~~~~~~         ~
       · Y  Q  R  V  M  E  S  F  K  K  E  G  R  I  G  A  G  G  G  S  G  G  G  S  M  G

1138   TTTATCAGCGAGTAATGGAAAGCTTTAAGAAGGAAGGGCGCATTGGCGCCGGTGGCGGATCAGGCGGTGGATCCATGGGG
       SalI
       ~~~~~
```

D)

```
          S  T  D  I  Q  M  T  Q  S  P  S  S  L  S  A  S  V  G  D  R  V  T  I  T  C  R  A ·
1218  TCGACGGACATCCAGATGACCCAGTCTCCATCCTCCCTGTCTGCATCTGTAGGAGACAGAGTCACCATCACTTGCCGGGC
        · S  Q  S  V  S  S  Y  L  N  W  Y  Q  Q  K  P  G  K  A  P  K  L  L  I  Y  L  A  S ·
1298  AAGTCAGAGCGTTAGCAGCTATTTAAATTGGTATCAGCAGAAACCAGGGAAAGCCCCTAAGCTCCTGATCTATCTTGCAT
        · R  L  Q  S  G  V  P  S  R  F  S  G  S  G  S  G  T  D  F  T  L  T  I  S  S  L
1378  CCCGTTTGCAAAGTGGGGTCCCATCAAGGTTCAGTGGCAGTGGATCTGGGACAGATTTCACTCTCACCATCAGCAGTCTG
          Q  P  E  D  F  A  T  Y  Y  C  Q  Q  N  W  W  L  P  P  T  F  G  Q  G  T  K  V  E ·
1458  CAACCTGAAGATTTTGCAACTTACTACTGTCAACAGAATTGGTGGCTGCCTCCTACGTTCGGCCAAGGGACCAAGGTGGA
                  NotI                                          XhoI
        · I  K  R  A  A  A  R  S  Y  P  Y  D  V  P  D  Y  A
1538  AATCAAACGGGCGGCCGCAAGATCCTATCCGTATGATGTGCCGGATTATGCGTAACTCGAGAGATCCGGTAACAAAGCCC
1618  GAAAGGAAGCTGAGTTGGCTGCTGCCACCGCTGAGCAATAACTAGCATAACCCCTTGGGGCCTCTAAACGGGTCTTGAGG
1698  GGTTTTTTGCTGAAAGGA
```

A) pIE2A    pIE2aA
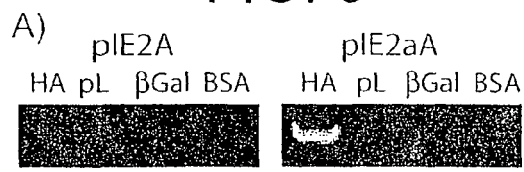

B) pIE3A    pIE3aA

FIG. 11
A)
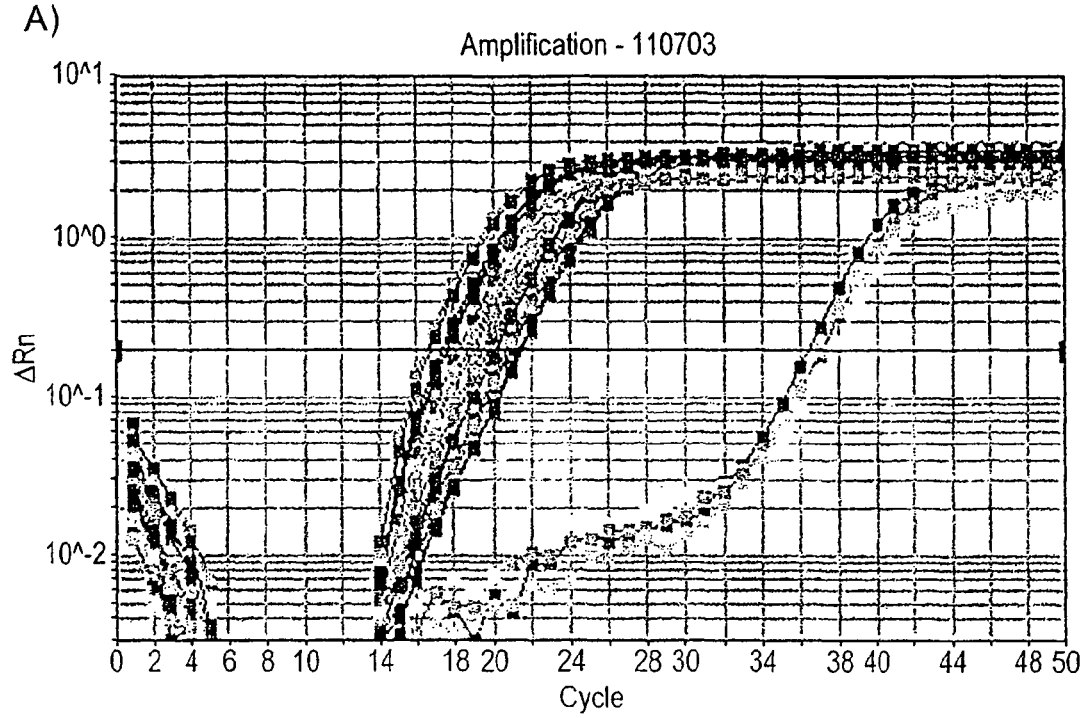
B)
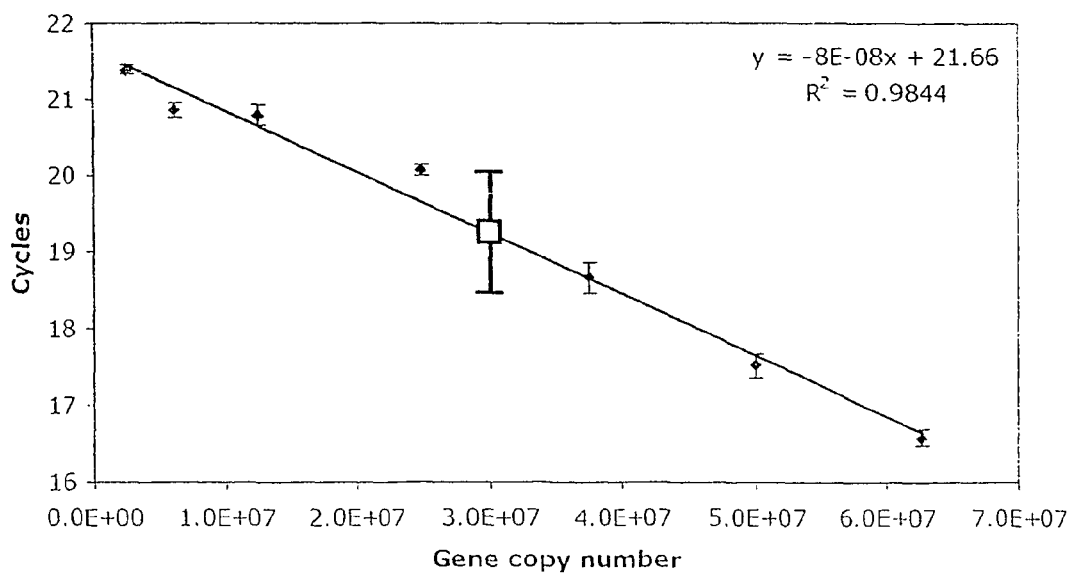

FIG. 16

FIG. 17
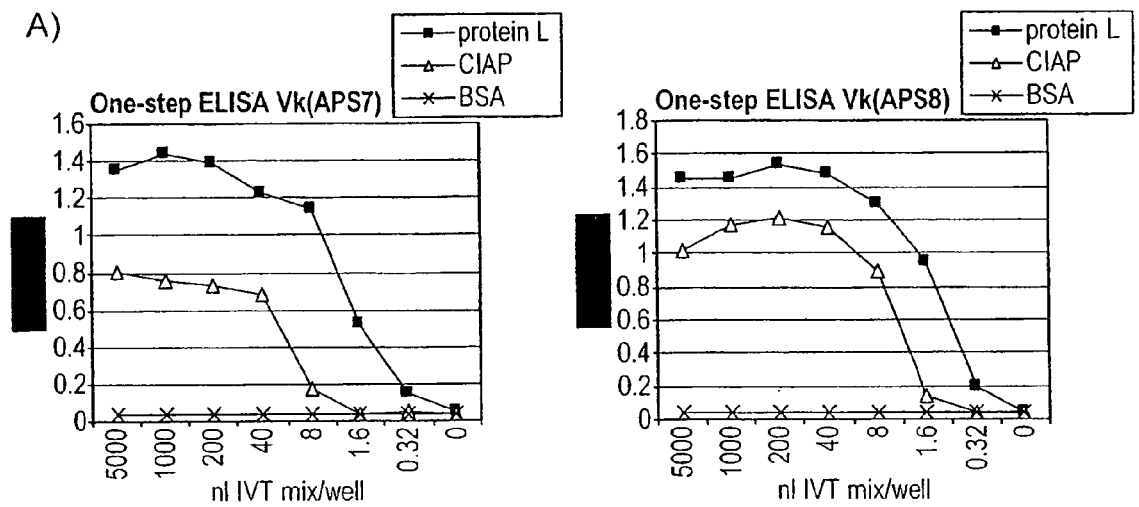
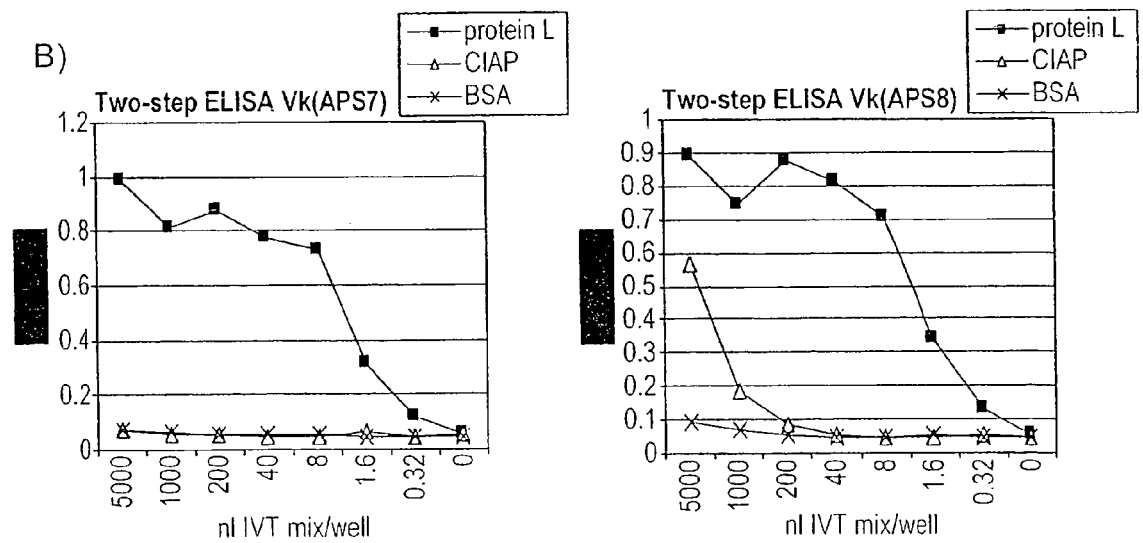

FIG. 18 CONT'D

```
                                        BglII
4231  ATCGAGATCCATAGTAGAGTGCTTCTATCATAGATCTCGATCCCGCGAAATTAATACGACTCACTATAGGGAGACCACAA
      TAGCTCTAGGTATCATCTCACGAAGATAGTATCTAGAGCTAGGGCGCTTTAATTATGCTGAGTGATATCCCTCTGGTGTT
                                                                    NcoI
                                                          M  A  E  V  Q  L  L  E  S  G
4311  CGGTTTCCCTCTAGAAATAATTTTGTTTAACTTTAAGAAGGAGATATACCATGGCCGAGGTGCAGCTGTTGGAGTCTGGG
      GCCAAAGGGAGATCTTTATTAAAACAAATTGAAATTCTTCCTCTATATGGTACCGGCTCCACGTCGACAACCTCAGACCC

G  G  L  V  Q  P  G  G  S  L  R  L  S  C  A  A  S  G  F  T  F  E  W  Y  W  M  G ·
32    GGAGGCTTGGTACAGCCTGGGGGGTCCCTGCGTCTCTCCTGTGCAGCCTCCGGATTCACCTTTGAGTGGTATTGGATGGG
      CCTCCGAACCATGTCGGACCCCCAGGGACGCAGAGAGGACACGTCGGAGGCCTAAGTGGAAACTCACCATAACCTACCC

·  W  V  R  Q  A  P  G  K  G  L  E  W  V  S  A  I  S  G  S  G  G  S  T  Y  Y  A  D ·
112   TTGGGTCCGCCAGGCTCCAGGGAAGGGTCTAGAGTGGGTCTCAGCTATCAGTGGTAGTGGTGGTAGCACATACTACGCAG
      AACCCAGGCGGTCCGAGGTCCCTTCCCAGATCTCACCCAGAGTCGATAGTCACCATCACCACCATCGTGTATGATGCGTC

·  S  V  K  G  R  F  T  I  S  R  D  N  S  K  N  T  L  Y  L  Q  M  N  S  L  R  A
192   ACTCCGTGAAGGGCCGGTTCACCATCTCCCGCGACAATTCCAAGAACACGCTGTATCTGCAAATGAACAGCCTGCGTGCC
      TGAGGCACTTCCCGGCCAAGTGGTAGAGGGCGCTGTTAAGGTTCTTGTGCGACATAGACGTTTACTTGTCGGACGCACGG

E  D  A  A  V  Y  Y  C  A  K  V  K  L  G  G  G  P  N  F  G  Y  R  G  Q  G  T  L ·
272   GAGGACGCCGCGGTATATTACTGTGCGAAAGTTAAGTTGGGGGGGGGGCCTAATTTTGGCTACCGGGGCCAGGGAACCCT
      CTCCTGCGGCGCCATATAATGACACGCTTTCAATTCAACCCCCCCCCGGATTAAAACCGATGGCCCCGGTCCCTTGGGA

XhoI     NotI
      ·  V  T  V  S  S  A  A  A  G  S  G  G  G  S  G  G  G  H  M  K  G  M  S  K  M  P  Q ·
352   GGTCACCGTCTCGAGCGCGGCCGCAGGATCTGGTGGCGGATCAGGCGGTGGACATATGAAAGGAATGAGCAAAATGCCGC
      CCAGTGGCAGAGCTCGCGCCGGCGTCCTAGACCACCGCCTAGTCCGCCACCTGTATACTTTCCTTACTCGTTTTACGGCG

·  F  N  L  R  W  P  R  E  V  L  D  L  V  R  K  V  A  E  E  N  G  R  S  V  N  S
432   AGTTCAATTTGCGGTGGCCTAGAGAAGTATTGGATTTGGTACGCAAGGTAGCGGAAGAGAATGGTCGGTCTGTTAATTCT
      TCAAGTTAAACGCCACCGGATCTCTTCATAACCTAAACCATGCGTTCCATCGCCTTCTCTTACCAGCCAGACAATTAAGA

E  I  Y  Q  R  V  M  E  S  F  K  K  E  G  R  I  G  A  G  G  G  S  G  G  G  S  G ·
512   GAGATTTATCAGCGAGTAATGGAAAGCTTTAAGAAGGAAGGCGCATTGGCGCCGGTGGCGGATCAGGCGGTGGATCTGG
      CTCTAAATAGTCGCTCATTACCTTTCGAAATTCTTCCTTCCGCGTAACCGCGGCCACCGCCTAGTCCGCCACCTAGACC

·  G  G  S  G  G  G  H  M  K  G  M  S  K  M  P  Q  F  N  L  R  W  P  R  E  V  L  D ·
592   TGGCGGATCAGGCGGTGGACATATGAAAGGAATGAGCAAAATGCCGCAGTTCAATTTGCGGTGGCCTAGAGAAGTATTGG
      ACCGCCTAGTCCGCCACCTGTATACTTTCCTTACTCGTTTTACGGCGTCAAGTTAAACGCCACCGGATCTCTTCATAACC

·  L  V  R  K  V  A  E  E  N  G  R  S  V  N  S  E  I  Y  Q  R  V  M  E  S  F  K
672   ATTTGGTACGCAAGGTAGCGGAAGAGAATGGTCGGTCTGTTAATTCTGAGATTTATCAGCGAGTAATGGAAAGCTTTAAG
      TAAACCATGCGTTCCATCGCCTTCTCTTACCAGCCAGACAATTAAGACTCTAAATAGTCGCTCATTACCTTTCGAAATTC
                                            BamHI                              XhoI
       K  E  G  R  I  G  A  G  G  G  S  G  G  G  S  Y  P  Y  D  V  P  D  Y  A
752   AAGGAAGGGCGCATTGGCGCCGGTGGCGGATCAGGCGGTGGATCCTATCCGTATGATGTGCCGGATTATGCGTAACTCGA
      TTCCTTCCCGCGTAACCGCGGCCACCGCCTAGTCCGCCACCTAGGATAGGCATACTACACGGCCTAATACGCATTGAGCT

XhoI
832   GAGATCCGGTAACAAAGCCCGAAAGGAAGCTGAGTTGGCTGCTGCCACCGCTGAGCAATAACTAGCATAACCCCTTGGGG
      CTCTAGGCCATTGTTTCGGGCTTTCCTTCGACTCAACCGACGACGGTGGCGACTCGTTATTGATCGTATTGGGGAACCCC

912   CCTCTAAACGGGTCTTGAGGGGTTTTTTGCTGAAAGG
      GGAGATTTGCCCAGAACTCCCCAAAAAACGACTTTCC
```

FIG. 20

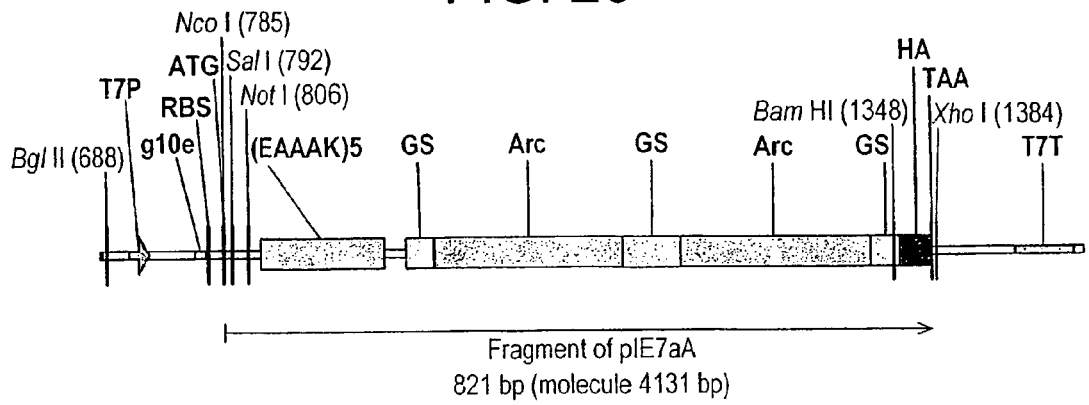

Fragment of pIE7aA
821 bp (molecule 4131 bp)

```
         BglII
684  CATAGATCTCGATCCCGCGAAATTAATACGACTCACTATAGGGAGACCACAACGGTTTCCCTCTAGAAATAATTTTGTTT

NcoI   SalI        NotI
             M  G  S  T  G  G  A  A  A  K  E  A  A  A  K  E  A  A  A  K
764  AACTTTAAGAAGGAGATATACCATGGGTCGACCGGCGGCGCGGCCGCAAAAGAAGCGGCGGCGAAAGAAGCGGCGGCGA

E  A  A  A  K  E  L  A  A  K  E  A  A  A  K  E  A  A  A  K  E  A  A  A  K  E
844  AAGAAGCGGCGGCGAAAGAATTGGCCGCAAAAGAAGCGGCGGCGAAAGAAGCGGCGGCGAAAGAAGCGGCGGCGAAAGAA

L  A  A  G  S  G  G  G  S  G  G  G  H  M  K  G  M  S  K  M  P  Q  F  N  L  R  W
924  TTGGCCGCAGGATCTGGTGGCGGATCAGGCGGTGGACATATGAAAGGAATGAGCAAAATGCCGCAGTTCAATTTGCGGTG

P  R  E  V  L  D  L  V  R  K  V  A  E  E  N  G  R  S  V  N  S  E  I  Y  Q  R  V
1004 GCCTAGAGAAGTATTGGATTTGGTACGCAAGGTAGCGGAAGAGAATGGTCGGTCTGTTAATTCTGAGATTTATCAGCGAG

M  E  S  F  K  K  E  G  R  I  G  A  G  G  G  S  G  G  G  S  G  G  G  S  G  G
1084 TAATGGAAAGCTTTAAGAAGGAAGGGCGCATTGGCGCCGGTGGCGGATCAGGCGGTGGATCTGGTGGCGGATCAGGCGGT

G  H  M  K  G  M  S  K  M  P  Q  F  N  L  R  W  P  R  E  V  L  D  L  V  R  K  V
1164 GGACATATGAAAGGAATGAGCAAAATGCCGCAGTTCAATTTGCGGTGGCCTAGAGAAGTATTGGATTTGGTACGCAAGGT

A  E  E  N  G  R  S  V  N  S  E  I  Y  Q  R  V  M  E  S  F  K  K  E  G  R  I  G
1244 AGCGGAAGAGAATGGTCGGTCTGTTAATTCTGAGATTTATCAGCGAGTAATGGAAAGCTTTAAGAAGGAAGGGCGCATTG

BamHI                              XhoI
      A  G  G  G  S  G  G  G  S  Y  P  Y  D  V  P  D  Y  A
1324 GCGCCGGTGGCGGATCAGGCGGTGGATCCTATCCGTATGATGTGCCGGATTATGCGTAACTCGAGAGATCCGGTAACAAA

1404 GCCCGAAAGGAAGCTGAGTTGGCTGCTGCCACCGCTGAGCAATAACTAGCATAACCCCTTGGGGCCTCTAAACGGGTCTT

1484 GAGGGGTTTTTTGCTGAAAGG
```

SELECTION

RELATED APPLICATIONS

This application is a Continuation of PCT/GB2005/003243 filed on Aug. 19, 2005, which claims priority to GB 048651.6, filed on Aug. 20, 2004, the entirety of which is incorporated herein by reference.

FIELD OF INVENTION

The present invention relates to the selection of polypeptide domains.

In particular, the present invention relates to the selection of one or more polypeptide domains using a nucleotide sequence encoding one or more Arc DNA binding domains, one or more Arc DNA binding sites and at least one polypeptide domain.

BACKGROUND TO THE INVENTION

Evolution requires the generation of genetic diversity (diversity in nucleic acid) followed by the selection of those nucleic acids which result in beneficial characteristics. Because the nucleic acid and the activity of the encoded gene product of an organism are physically linked (the nucleic acids being confined within the cells which they encode) multiple rounds of mutation and selection can result in the progressive survival of organisms with increasing fitness. Systems for rapid evolution of nucleic acids or proteins in vitro should mimic this process at the molecular level in that the nucleic acid and the activity of the encoded gene product must be linked and the activity of the gene product must be selectable.

Recent advances in molecular biology have allowed some molecules to be co-selected according to their properties along with the nucleic acids that encode them. The selected nucleic acids can subsequently be cloned for further analysis or use, or subjected to additional rounds of mutation and selection.

Common to these methods is the establishment of large libraries of nucleic acids. Molecules having the desired characteristics (activity) can be isolated through selection regimes that select for the desired activity of the encoded gene product, such as a desired biochemical or biological activity, for example binding activity.

Phage display technology has been highly successful as providing a vehicle that allows for the selection of a displayed protein by providing the essential link between nucleic acid and the activity of the encoded gene product (Smith, 1985; Bass et al., 1990; McCafferty et al., 1990; for review see Clackson and Wells, 1994). Filamentous phage particles act as genetic display packages with proteins on the outside and the genetic elements, which encode them on the inside. The tight linkage between nucleic acid and the activity of the encoded gene product is a result of the assembly of the phage within bacteria. As individual bacteria are rarely multiply infected, in most cases all the phage produced from an individual bacterium will carry the same nucleotide sequence and display the same protein.

However, phage display relies upon the creation of nucleic acid libraries in vivo in bacteria. Thus, the practical limitation on library size allowed by phage display technology is of the order of $10^7$ to $10^{11}$, even taking advantage of λ phage vectors with excisable filamentous phage replicons. The technique has mainly been applied to selection of molecules with binding activity. A small number of proteins with catalytic activity have also been isolated using this technique, however, in no case was selection directly for the desired catalytic activity, but either for binding to a transition-state analogue (Widersten and Mannervik, 1995) or reaction with a suicide inhibitor (Soumillion et al., 1994; Janda et al., 1997).

Another method is called Plasmid Display in which fusion proteins are expressed and folded within the *E. coli* cytoplasm and the phenotype-genotype linkage is created by the fusion proteins binding in vivo to DNA sequences on the encoding plasmids whilst still compartmentalised from other members of the library. In vitro set on from a protein library can then be performed and the plasmid DNA encoding the proteins can be recovered for re-transformation prior to characterisation or further selection. Specific peptide ligands have been selected for binding to receptors by affinity selection using large libraries of peptides linked to the C terminus of the lac repressor LacI (Cull et al., 1992). When expressed in *E. coli* the repressor protein physically links the ligand to the encoding plasmid by binding to a lac operator sequence on the plasmid. Speight et al. (2001) describe a Plasmid Display method in which a nuclear factor κB p50 homodimer is used as a DNA binding protein which binds to a target κB site in the −10 region of a lac promoter. The protein-DNA complexes that are formed have improved stability and specificity.

An entirely in vitro polysome display system has also been reported (Mattheakis et al., 1994) in which nascent peptides are physically attached via the ribosome to the RNA which encodes them.

In vitro RNA selection and evolution (Ellington and Szostak, 1990), sometimes referred to as SELEX (systematic evolution of ligands by exponential enrichment) (Tuerk and Gold, 1990) allows for selection for both binding and chemical activity, but only for nucleic acids. When selection is for binding, a pool of nucleic acids is incubated with immobilised substrate Non-binders are washed away, then the binders are released, amplified and the whole process is repeated in iterative steps to enrich for better binding sequences. This method can also be adapted to allow isolation of catalytic RNA and DNA (Green and Szostak, 1992; for reviews see Chapman and Szostak, 1994; Joyce, 1994; Gold et al., 1995; Moore, 1995).

WO99/02671 describes an in vitro sorting method for isolating one or more genetic elements encoding a gene product having a desired activity, comprising compartmentalising genetic elements into microcapsules; expressing the genetic elements to produce their respective gene products within the microcapsules; and sorting the genetic elements which produce the gene product having the desired activity. The invention enables the in vitro evolution of nucleic acids by repeated mutagenesis and iterative applications of the method of the invention.

In contrast to other methods WO99/02671 describes a man-made "evolution" system which can evolve both nucleic acids and proteins to effect the full range of biochemical and biological activities (for example, binding, catalytic and regulatory activities) and that can combine several processes leading to a desired product or activity.

A prerequisite for in vitro selection from large libraries of proteins is the ability to identify those members of the library with the desired activity (eg. specificity). However, direct analysis of the selected protein requires much larger amounts of materials than are typically recovered in such experiments. One way in which this problem can be addressed involves the creation of a physical association between the encoding gene and the protein throughout the selection process and so the protein can be amplified and characterised by the encoding DNA or RNA.

The present invention seeks to provide an improved method for the in vitro selection of polypeptide domains according to their binding activity.

SUMMARY OF THE INVENTION

The present invention relates, in part, to the surprising finding that Arc can be used for the in vitro selection of a polypeptide domain.

Thus, in a first aspect, the present invention relates to a nucleotide sequence encoding one or more Arc DNA binding domains, one or more Arc DNA binding sites and at least one polypeptide domain.

The nucleotide sequence is expressed to produce its respective polypeptide domain gene product in fusion with the Arc DNA-binding domain (eg. a single chain Arc DNA-binding domain). Once expressed, the polypeptide domain gene product becomes associated with its respective nucleotide sequence through the binding of the Arc DNA binding domain in the gene product to the Arc DNA binding site of the respective nucleotide sequences. Typically, the nucleotide sequence of the present invention will be expressed within a microcapsule. The microcapsules comprising the nucleotide sequence can teen be pooled into a common compartment in such a way that the nucleotide sequence bound to the polypeptide domain, preferably, an polypeptide domain (eg. an antibody domain) with desirable properties (eg. specificity or affinity), may be selected.

The nucleotide sequences according to the present invention may be cloned into a construct or a vector to allow further characterisation of the nucleotide sequences and their polypeptide domain gene products.

Thus, in a second aspect, the present invention relates to a construct comprising the nucleotide sequence according to the first aspect of the present invention.

In a third aspect, the present invention relates to a vector comprising the nucleotide sequence according to the first aspect of the present invention.

In a fourth aspect, the present invention relates to a host cell comprising the construct according to the second aspect of the present invention or the vector according to the third aspect of the present invention.

In a fifth aspect, the present invention relates to a protein encoded by the nucleotide sequence according to the first aspect of the present invention.

In a sixth aspect, the present invention relates to a protein-DNA complex comprising the protein according to the fifth aspect of the present invention bound to a nucleotide sequence according to the first aspect of the present invention—such as via one or more Arc DNA binding sites.

Successful selection of polypeptide (eg. antibody) domain-Arc fusion proteins on the basis of the antigen-binding activity depends among other factors also on the stability of the protein-DNA complex. The dissociation rate of the fusion protein-DNA interaction should be sufficiently low to maintain the genotype-phenotype linkage throughout the emulsion breakage and the subsequent affinity capture stage. Surprisingly, the inventors have found that it is possible to stabilise the protein-DNA complex via their tags sequences using a protein—such as a monoclonal antibody.

In a seventh aspect, the present invention relates to a method for preparing a protein-DNA complex according to the sixth aspect of the present invention, comprising the steps of: (a) providing a nucleotide sequence according to the first aspect of the present invention, a construct according to the second aspect of the present invention or a vector according to the third aspect of the present invention; and (b) expressing the nucleotide sequence to produce its respective protein; and (c) allowing for the formation of the protein-DNA complex.

In an eighth aspect, the present invention relates to a method for isolating one or more nucleotide sequences encoding a polypeptide domain with a desired specificity, comprising the steps of: (a) providing a nucleotide sequence according to the first aspect of the present invention, a construct according to the second aspect of the present invention or a vector according to the third aspect of the present invention; (b) compartmentalising the nucleotide sequence into microcapsules; (c) expressing the nucleotide sequence to produce its respective polypeptide domain; (d) pooling the microcapsules into a common compartment; and (e) selecting the nucleotide sequence which produces a polypeptide domain having the desired specificity.

The polypeptide domain nucleotide sequences are expressed to produce their respective polypeptide domain gene products within a microcapsule, such that the gene products are associated with the nucleotide sequences encoding them and the complexes thereby formed can be sorted. Advantageously, this allows for the nucleotide sequences and their associated gene products to be sorted according to the polypeptide domain specificity.

The nucleotide sequences may be sorted by a multi-step procedure, which involves at least two steps, for example, in order to allow the exposure of the polypeptide domain nucleotide sequences to conditions, which permit at least two separate reactions to occur. As will be apparent to a person skilled in the art, the first microencapsulation step must result in conditions which permit the expression of the polypeptide domain nucleotide sequences—be it transcription, transcription and/or translation, replication or the like. Under these conditions, it may not be possible to select for particular polypeptide domain specificity, for example because the polypeptide domain may not be active under these conditions, or because the expression system contains an interfering activity.

Therefore, the selected polypeptide domain nucleotide sequence(s) may be subjected to subsequent, possibly more stringent rounds of sorting in iteratively repeated steps, reapplying the method of the present invention either in its entirety or in selected steps only. By tailoring the conditions appropriately, nucleotide sequences encoding polypeptide domain gene products having a better optimised specificity may be isolated after each round of selection.

The nucleotide sequence and the polypeptide domain thereby encoded are associated by confining each nucleotide sequence and the respective gene product encoded by the nucleotide sequence within the same microcapsule. In this way, the gene product in one microcapsule cannot cause a change in any other microcapsules.

Additionally, the polypeptide domain nucleotide sequences isolated after a first round of sorting may be subjected to mutagenesis before repeating the sorting by iterative repetition of the steps of the method of the invention as set out above. After each round of mutagenesis, some polypeptide domain nucleotide sequences will have been modified in such a way that the specificity of the gene products is enhanced.

In a ninth aspect, the present invention relates to a method for preparing a polypeptide domain, comprising the steps of (a) providing a nucleotide sequence according to the first aspect of the present invention, a construct according to the second aspect of the present invention or a vector according to the third aspect of the present invention; (b) compartmentalising the nucleotide sequences; (c) expressing the nucleotide sequences to produce their-respective gene products; (d) sorting the nucleotide sequences which produce polypeptide domains having the desired specificity; and (e) expressing the polypeptide domains having the desired specificity.

In a tenth aspect, the present invention relates to a protein-DNA complex obtained or obtainable by the method according to the seventh aspect of the present invention.

In an eleventh aspect, the present invention relates to a polypeptide domain obtained or obtainable by the method according to the eighth or ninth aspects of the present invention.

In a twelfth aspect, the present invention relates to the use of Arc in the selection of a polypeptide domain.

In a thirteenth aspect, the present invention relates to the use of oxidised glutathione for the preparation of a protein-DNA complex.

Preferably, the polypeptide domain is an antibody domain.

Preferably, the antibody domain is a $V_L$, $V_H$ or Camelid $V_{HH}$ domain.

Preferably, the nucleotide sequence comprises a tag sequence.

Preferably, the tag sequence is included at the 3' end of the nucleotide sequence.

Preferably, the tag sequence is selected from the group consisting of HA, FLAG or c-Myc.

Preferably, the polypeptide domain is fused directly or indirectly to the N- or C-terminus of the Arc DNA binding domain(s).

Preferably, the Arc DNA binding domain(s) comprises or consists of the sequence set forth in Seq ID No 4 or Seq ID No 5.

Preferably, the nucleotide sequence additionally comprises one or more linkers.

Preferably, the nucleotide sequence comprises 2, 3 or 4 Arc DNA-binding domains.

Preferably, the antibody domain is $V_\kappa$.

Preferably, the complex additional comprises a protein bound to the tag sequence.

Preferably, the tag sequence is HA.

Preferably, the protein bound to the tag sequence is an antibody.

Preferably, the antibody is a monoclonal antibody.

Preferably, the monoclonal antibody is αHA rat mAb 3F10 (Roche), a monoclonal antibody that binds the same HA epitope as αHA rat mAb 3F10 (Roche), or competes with αHA rat mAb 3F10 (Roche) for binding to HA.

Preferably, the monoclonal antibody is used at a concentration of about 3.4 nM.

Preferably, the nucleotide sequence is expressed in the presence of glutathione.

Preferably, the glutathione is oxidised glutathione.

Preferably, the method according to the eighth aspect further comprises the additional step of: (f) introducing one or more mutations into the polypeptide domain.

Preferably, the method according to the eighth aspect further comprises iteratively repeating one or more of steps (a) to (e).

Preferably, the method according to the eighth aspect further comprises amplifying the polypeptide domain.

Preferably, the polypeptide domains are sorted by affinity purification.

Preferably, the polypeptide domains are sorted using protein L.

Preferably, the polypeptide domains are sorted by selective ablation of polypeptide domains, which do not encode the desired polypeptide domain gene product.

DESCRIPTION OF THE FIGURES

FIG. 3 The sequence of scArc construct in pBS/scArc. A) The domain structure of the scArc protein. B) The DNA sequence of scArc repressor. The chimeric BamHI/BglII site used for concatemerization of GS-flanked Arc repressor monomers is underlined. The sequences shown correspond to SEQ ID NOs 65 and 66.

FIG. 6 The formation of protein-DNA complex between HA-tagged protein, derived form series pIE2 (A) or series pIE3 (B) vectors, and its encoding DNA fragment depends on the presence of the Arc operator on the genetic element. The complex formation is detected through capture by biotinylated α-HA mAb, protein L (pL), β-galactosidase (βGal) or BSA, all immobilised onto streptavidin-coated PCR tubes, in ELISA-like format using PCR (C).

FIG. 11 Quantitative PCR assay of protein DNA complexes recovered from an emulsified reaction sample expressing the template derived from pIE3a$^4$AVκ(E5). A) Amplification profiles of the standard, negative control and unknown samples. B) Calibration curve for the standard samples (filled diamonds) with the unknown (empty square) superimposed on the plot.

FIG. 16 Amino acid sequences of 11 CIAP-binding V[kappa] clones after five rounds of selection. The CIAP-binding sequences fall into two categories with prototype sequences chosen as APS7 and APS8 respectively. The residues from randomised positions in the library are underlined. The sequences correspond to SEQ ID NOs: 79-87.

FIG. 17 The antigen-binding activities of in vitro translated anti-CIAP V$_\kappa$ dAb clones APS7 and APS8, as detected by one-step ELISA (A) or two-step ELISA (B). Protein L binding is indicative of the V$_\kappa$ concentration in the well, BSA serves as a negative control and CIAP measures specific binding.

FIG. 20 The multiple cloning site of vectors pIE7a<n>A where n=I-4 encodes an additional (KAAAE)6 linker upstream of the N-terminal GS-linker that serves to further isolate the scFv and scArc domains of the fusion protein. The sequences shown correspond to SEQ ID NOs 77 and 78.

DETAILED DESCRIPTION OF THE INVENTION

Polypeptide Domain

Figure 1:
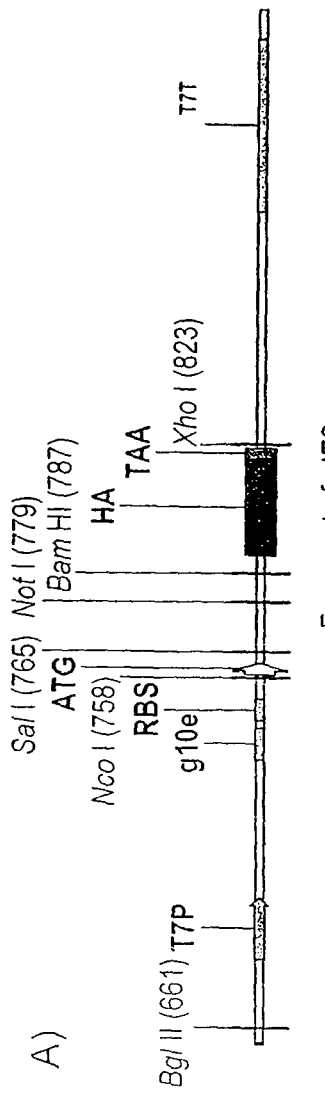
FIG. 1 The expression cassettes of the pIE in vitro expression vectors where T7P denotes T7 promoter, glOe—glO enhancer, RBS—ribosome binding site, ATG—translation start site, HA—HA tag, TAA—stop codon and T7T—T7 terminator. A) The scheme and the MCS sequence for pIE2. B) The scheme and the MCS sequence for pIE2. The sequences shown correspond to SEQ ID NOs 57-60.
Figure 1:
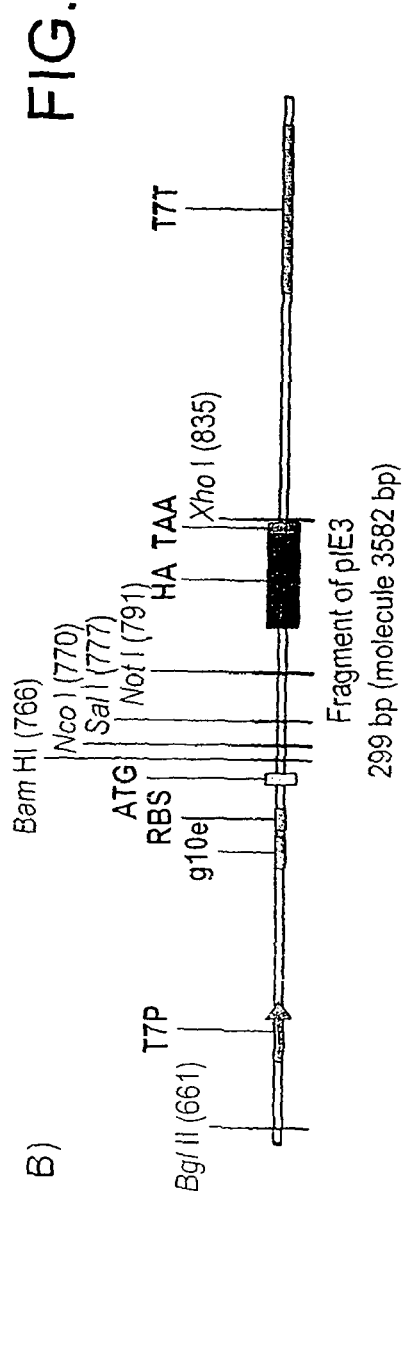

As used herein, the term "polypeptide domain" refers to a molecule or molecular construct that encodes a polypeptide domain—such as a V$_H$ or a V$_L$ domain.

In a preferred embodiment, the polypeptide domain is an antibody domain.

A typical antibody is a multi-subunit protein comprising four polypeptide chains; two "heavy" chains and two "light" chains. The heavy chain has four domains, the light chain has two domains. All of the domains are classified as either variable or constant.

The antigen binding domain of an antibody comprises two separate regions: a heavy chain variable domain (V$_H$) and a light chain variable domain (V$_L$: which can be either V$_\kappa$ or V$_\lambda$).

The antigen-binding site itself is formed by six polypeptide loops: three from the V$_H$ domain (H1, H2 and H3) and three from the V$_L$ domain (L1, L2 and L3).

The V$_H$ gene is produced by the recombination of three gene segments, V$_H$, D and J$_H$. In humans, there are approximately 51 functional V$_H$ segments (Cook and Tomlinson (1995) *Immunol Today*, 16: 237), 25 functional D segments (Corbett et al. (1997) *J. Mol. Biol.*, 268: 69) and 6 functional J$_H$ segments (Ravetch et al. (1981) *Cell*, 27: 583), depending on the haplotype. The V$_H$ segment encodes the region of the polypeptide chain which forms the first and second antigen binding loops of the V$_H$ domain (H1 and H2), whilst the V$_H$, D and J$_H$ segments combine to form the third antigen binding loop of the V$_H$ domain (H3).

The V$_L$ gene is produced by the recombination of two gene segments, V$_L$ and J$_L$. In humans, there are approximately 40 functional V$_\kappa$ segments (Schäble and Zachau (1993) *Biol. Chem. Hoppe-Seyler*, 374: 1001), 31 functional V$_\lambda$ segments (Williams et al. (1996) *J. Mol. Biol.*, 264: 220; Kawasaki et al. (1997) *Genome Res.*, 7: 250), 5 functional J$_\kappa$ segments (Hieter et al. (1982) *J. Biol. Chem.*, 257: 1516) and 4 functional J$_\lambda$ segments (Vasicek and Leder (1990) *J. Exp. Med.*, 172: 609), depending on the haplotype. The V$_L$ segment encodes the region of the polypeptide chain which forms the first and second antigen binding loops of the $V_L$ domain (L1 and L2), whilst the $V_L$ and $J_L$ segments combine to form the third antigen binding loop of the $V_L$ domain (L3). Antibodies selected from this primary repertoire are believed to be sufficiently diverse to bind almost all antigens with at least moderate affinity. High affinity antibodies are produced by "affinity maturation" of the rearranged genes, in which point mutations are generated and selected by the immune system on the basis of improved binding.

The polypeptide domains may be provided in the form of a library.

Typically, the antibody domains will be provided in the form of a library, which will in most cases require the screening of a large number of variant antibody domains. Libraries of antibody domains may be created in a variety of different ways, including the following.

Pools of naturally occurring antibody domains may be cloned from genomic DNA or cDNA (Sambrook et al., 1989); for example, phage antibody libraries, made by PCR amplification repertoires of antibody genes from immunised or unimmunised donors have proved very effective sources of functional antibody fragments (Winter et al., 1994; Hoogenboom, 1997). Libraries of genes encoding antibody domains may also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries may also be made by introducing mutations into an antibody domain or pool of antibody domains 'randomly' by a variety of techniques in vivo, including; using 'mutator strains', of bacteria such as E. coli mutD5 (Liao et al., 1986; Yamagishi et al., 1990; Low et al., 1996), and using the antibody hypermutation system of B-lymphocytes (Yelamos et al., 1995) Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). 'Random' mutations can also be introduced into antibody domains genes in vitro during polymerisation for example by using error-prone polymerases (Leung et al., 1989).

Further diversification may be introduced by using homologous recombination either in vivo (see Kowalczykowski et al., 1994 or in vitro (Stemmer, 1994a; Stemmer, 1994b)).

Preferably, the antibody domain is a $V_H$ or a $V_L$ antibody domain.

The antibody domain may be a Camelid VHH domain (ie. a V domain derived or derivable from a Camelid antibody consisting of two heavy chains).

The antibody domain may be part of a monoclonal antibody (mAb), eg. $V_L$ or $V_K$ single-domain antibody (dAb). dabs are described in Ward et al. (1989) Nature 341, p 544-546.

Preferably, the antibody $V_L$ domain is $V_K$.

The polypeptide domain may be fused directly or indirectly to the N-terminus or the C-terminus of the Arc DNA binding domain(s).

Preferably, the polypeptide domain is fused directly or indirectly to the N-terminus of the Arc DNA binding domain(s).

In this context, the term "directly" means that the polypeptide domain is fused to the Arc DNA binding domain(s) in the absence of a linker.

In this context, the term "indirectly" means that the polypeptide domain is fused to the Arc DNA binding domain(s) via at least a linker.

Preferably, the polypeptide domain is fused indirectly to the N-terminus or the C-terminus of the Arc DNA binding domain(s). More preferably, the polypeptide domain is fused indirectly to the N-terminus of the Arc DNA binding domain(s).

Typically, the Arc DNA binding site will be located at the 5' end of the nucleotide sequence.

Variable domains may even be linked-together to form multivalent ligands by, for example: provision of a hinge region at the C-terminus of each V domain and disulphide bonding between cysteines in the hinge regions.

DNA-Binding Domains

The DNA-binding domain that provides the genotype-phenotype linkage in an emulsion-based in vitro selection should satisfy several criteria.

The DNA-binding proteins should form a highly stable protein-DNA complex in the in vitro translation mix. High stability means in this context, a very low dissociation rate constant such that the genotype-phenotype linkage between a gene and its encoded protein product is faithfully maintained throughout the processes of breaking the emulsion and the affinity capture of the protein-DNA complexes with desired properties. Typically, the genotype-linkage should be maintained at arc acceptable level for at least approximately ten minutes, meaning that the dissociation rate constant should be at least in the region of $10^{-3}$ s$^{-1}$ or smaller.

Ideally, the DNA-binding domain should not interfere with the binding properties of the polypeptide domain (whether or not it is fused to the N- or C-terminus) and should not lose any DNA-binding activity itself in the fusion protein format.

Finally, it can be advantageous if the DNA-binding protein does not have any Cystein residues (either reduced or oxidised) in the functionally active form of the fusion protein. Cystein residues in the DNA-binding domain of the fusion protein format may interfere with the intradomain oxidation of the cystein residues of the polypeptide (eg. antibody) domain. Additionally, the redox conditions which are optimal for in vitro expression may not be optimal for the DNA binding domain.

Many different DNA-binding proteins have been identified from species ranging from bacteria to vertebrates. As of July 2001, the SWISS-PROT database (Release 38) contained 3238 full-length sequences which contained at least one DNA-binding domain. These 3238 sequences were further classified into 22 structurally related families (Karmirantzou & Hamodrakas (2001). Many of these DNA-binding proteins have been studied in great detail, including binding characteristics and three-dimensional structures, often in complex with DNA fragments bearing-cognate binding sites (Karmirantzou & Hamodrakas (2001). For example, among the best-studied DNA-binding proteins with lower Kd values are Zn-finger proteins, e.g. TFIIIA from Xenopus (Miller et al. 1985) and Arc repressor from phage P22 (Raumann et al. (1994)).

The consensus sequence for the TFIIIA-type zinc finger domains is Tyr/Phe-X-Cys-X24-Cys-X3-Phe-X5-Leu-X2-His-X3-5-His (where X is any amino acid). As a rule there are from 2 up to 37 Zn-finger domains per protein, usually arranged in tandem. Each zinc finger is an autonomously folding mini-domain, which is dependent on a zinc ion for stability. The tertiary structure of a typical Zn-finger domain is comprised of an anti parallel β-sheet packed against a predominantly α-helical domain, with the invariant cysteines and histidines chelating the zinc ion and the three conserved hydrophobic residues forming a core (Choo & Klug (1993)). However, although extremely high-affinity Zn-finger proteins have been designed and characterised, with Kd values in low pM range, these proteins require the presence of 5 mM DTT for the preservation of functional activity (Moore et al. (2001)). Such strongly reducing conditions are unsuitable for the in vitro expression of antibody fragments, as demonstrated in the case of single-chain antibodies (Ryabova & Desplancq, et al. (1997)).

In contrast, wild-type Arc repressor from the P22 bacteriophage is a member of the ribbon-helix-helix family of transcription factors which controls transcription during the lytic growth of bacteriophage P22 by binding to the semi-palindromic Arc operator as a dimer of dimers. Each Arc dimer uses an antiparallel beta-sheet to recognize bases in the major groove whilst a different part of the protein surface is involved in dimer-dimer interactions.

At high concentrations, the Arc repressor is a reasonably stable dimer. However, at the sub-nanomolar concentrations where half-maximal operator binding is observed, Arc dimers disassociate and most molecules exist as unfolded monomers.

The dimers of Arc repressor are significantly stabilised if expressed in the form of a glycin-serine-linked single-chain protein (scArc). The dissociation constant Kd for such a single-chain construct has a value of about 2 pM whilst the dissociation half-life is about two hours (Robinson & Sauer (1996)).

At the same time, while the Zn-finger proteins are highly diverse in nature in the sense of frequently encoding also non-Zn-finger domains, there are no such variants known for Arc repressor and its suitability for expression in fusion protein format is more uncertain.

In general, there may be more than one operator site present on the genetic elements allowing the binding of multiple copies of the fusion protein. Such multiplication of the identical copies of protein molecules encoded by a given gene can be used to harness the avidity effect in antibody-antigen interactions, since the number of polypeptide domains associated with a DNA protein increases too when the number of DNA-bound protein molecules increases.

Interestingly, as has been shown in the case of Zn-finger proteins, the stability of such DNA-binding suitably arranged complexes can be further enhanced if a dimerising domain, e.g. leucine zipper, is expressed as part of the fusion protein (Wolfe et al. (2003)). It is conceivable that dimerisation could also further stabilise the dimer of scArc complexes on the Arc DNA binding site (eg. the Arc operator). In the first instance an anti-tag monoclonal antibody directed at a suitably placed peptide tag could cross-link the Arc DNA binding site-bound scArc, thereby stabilising the complex through the avidity effect. Alternatively, a dimerisation domain could be used, or a disulphide bond engineered into the interface between the operator-bound scArc molecules, to further stabilise that protein-DNA complex.

Arc DNA Binding Domain

As used herein, the term "Arc DNA-binding domain" refers to a domain of an Arc DNA binding protein that is required for the protein to bind to an Arc DNA binding site. The binding between the Arc DNA binding protein(s) and the Arc DNA binding site(s) will be maintained throughout the emulsion breakage and the subsequent affinity capture stage, preferably for about at least 1 hour.

Preferably, the Arc DNA binding domain(s) comprises the sequence set forth in Seq ID No. 4. More preferably, the Arc DNA binding domain consists of the sequence set forth in Seq ID No. 4.

The sequence of the DNA binding domain(s) may be modified (eg. mutated) to modulate the degree of binding.

Accordingly, mutated DNA binding domain(s) are also contemplated provided that such mutants have DNA binding domain activity, preferably being at least as biologically active as the DNA binding domain from which the mutated sequence was derived. Preferably, if the sequence of the Arc DNA binding domain(s) is modified, then the degree of binding is increased.

The nucleotide sequence according to the present invention may comprise one or more Arc DNA-binding domains, for example, 1, 2, 3, 4, 5 or even more Arc DNA-binding domains.

Preferably, the nucleotide sequence comprises 2, 3 or 4 Arc DNA-binding domains.

Advantageously, the use of more than one Arc DNA-binding domains improves the selection of the polypeptide domains. Accordingly, the Arc DNA binding domain may be a monomer or it may comprise a plurality of Arc DNA binding domains.

Advantageously, the use of a plurality of Arc DNA binding domain(s) increases the activity of the Arc DNA binding domain(s) relative to the wild type Arc DNA binding domain(s) as described in Robinson & Sauer (1996).

A plurality of Arc DNA binding domains may be obtained by designing a recombinant gene containing tandem copies of the Arc DNA binding domain(s) coding sequence with intervening DNA encoding a sequence to join the Arc DNA binding domain(s). Preferably, this sequence joins the C-terminus of one Arc DNA binding domain monomer to the N-terminus of the next Arc DNA binding domain.

The Arc DNA binding domain(s) may be joined by a linker.

Methods for obtaining novel DNA-binding proteins have been described in the art. By way of example, novel DNA-binding proteins that preferentially bind a predetermined DNA sequence in double stranded DNA are described in U.S. Pat. No. 5,096,815. Mutated genes that specify novel proteins with desirable sequence-specific DNA-binding properties are separated from closely related genes that specify proteins with no or undesirable DNA-binding properties.

A person skilled in the art will appreciate that such methods may be used to design novel Arc DNA-binding proteins—such as novel Arc repressors. Advantageously, novel Arc DNA-binding proteins that bind specific DNA sequence motifs—such as Arc wild type or mutated DNA binding sites—may be used in the present invention.

The activity of an Arc DNA binding domain(s) may be determined using various methods in the art—such as those described in Robinson & Sauer (1996)—including DNase I and copper-phenanthroline footprinting studies.

Advantageously, the present inventors have also discovered that when expressing polypeptide domains that are fused to the N-terminus of the Arc DNA binding domain(s), optimal results are obtained when a protein that binds to the tag sequence of the nucleotide sequence of the present invention is used.

Without wishing to be bound by theory, the protein (eg. the anti-tag monoclonal antibody) that binds to the tag sequence of the nucleotide sequence may cross link the DNA binding protein—such as the Arc operator-bound scArc—to stabilise the complex through an avidity effect.

Preferably, the protein that binds to the tag sequence is able to maintain the phenotype-genotype linkage throughout the emulsion breakage and subsequent affinity capture stage, for at east about 1 hour.

Preferably, the protein that binds to the tag sequence is a multivalent (eg. bivalent) reagent—such as an antibody which may include, but is not limited to, a polyclonal antibody, a monoclonal antibody, a chimeric antibody, a single chain antibody, a Fab fragment and/or a fragment produced by a Fab expression library.

For the production of antibodies, various hosts including goats, rabbits, rats, mice, etc. may be immunised by injection with a protein. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guerin) and *Corynebacterium parvum* are potentially -useful human adjuvants which may be employed.

Preferably, the antibody is a monoclonal antibody.

Monoclonal antibodies may be prepared using any technique which provides for the production of antibody molecules by continuous cell lines in culture. These include, but are not limited to, the hybridoma technique originally described by Koehler and Milstein (1975 Nature 256:495-497), the human B-cell hybridoma technique (Kosbor et al (1983) Immunol Today 4:72; Cote et al (1983) Proc Natl Acad Sci 80:2026-2030) and the EBV-hybridoma technique (Cole et al (1985) Monoclonal Antibodies and Cancer Therapy, Alan R Liss Inc, pp 77-96).

If the tag is the C-myc motif (EQKLISEED1) then an antibody that is or is derived from the monclonal antibody 9E10 (Catalogue number 1 667 149, Roche) may be used.

If the tag is the anti-FLAG-tag. (DYKDDDDK) (Hopp et. al. (1988)) then an antibody that is or is derived from the monclonal antibody M5 (Catalogue number F4042, Sigma) may be used.

In a highly preferred embodiment, the tag sequence is HA. Therefore, the antibody may be any antibody that recognises the HA peptide sequence (YPYDVPDYA) which is derived from the human hemagglutinin protein (Wilson et al. (1984)).

The antibody that binds the HA tag may be or may be derived from mouse 12CA5.

Preferably, the antibody that binds the HA tag is, or is derived from the High Affinity anti-HA (3F10) monoclonal antibody (Cat. No. 3 013 819, Roche).

Arc DNA Binding Site

The term "Arc DNA binding site" refers to a DNA sequence to which an Arc DNA-binding domain—such as an Arc repressor—binds.

Preferably, the term "Arc DNA binding site" refers to an Arc operator to which an Arc DNA-binding domain—such as an Arc repressor—binds. More preferably, the term "Arc DNA binding site" refers to an Arc operator to which an Arc repressor binds.

Preferably, the Arc DNA-binding domain can bind with high affinity and specificity.

Preferably, the Arc DNA-binding domains repeat after about a 45 bp interval which corresponds approximately to four helical turns of the B-form DNA. Without wishing to be bound by theory, this ensures that the DNA-bound fusion proteins are all exposed in the same direction in order to facilitate the avidity effect from multi-protein complexes.

Various Arc DNA binding sites have been described in the art, for example, in Accession Numbers 1PARF, 1PARE, and AF527608, *J. Biol. Chem.* (1992) 267, p 9134-9139 and *J. Biol. Chem.* (1997) 272, p 19898-19905.

Preferably, the Arc DNA binding site(s) comprises the sequence shown in Seq ID No.1 (Smith, T. L. and R. T. Sauer (1996).

Preferably, the Arc DNA binding site(s) consists of the sequence shown in Seq ID No.1

The Arc DNA binding site(s) may also comprise fragments of the sequence shown in Seq ID No.1.

The fragments of the Arc DNA binding site(s) may comprise the sequences shown in Seq ID No.2 and/or Seq ID No.3.

The fragments of the Arc DNA binding site(s) may consist of the sequences shown in Seq ID No.2 and/or Seq ID No.3.

The sequence of the DNA binding site(s) may be modified (eg. mutated) to modulate the degree of binding to the Arc DNA binding domain(s). Preferably, if the sequence of the DNA binding site(s) is modified, then the degree of binding to the Arc DNA binding domain(s) is increased.

Tag Sequence

As used herein the term "tag sequence" refers to one or more additional sequences that are added to facilitate protein purification and/or isolation.

Examples of tag sequences include glutathione-S-transferase (GST), 6xHis, GAL4 (DNA binding and/or transcriptional activation domains), β-galactosidase, the C-myc motif, the anti-FLAG-tag or the HA tag. It may also be convenient to include a proteolytic cleavage site between the tag sequence and the protein sequence of interest to allow removal of fusion protein sequences.

Preferably the fusion protein will not hinder the activity of the protein sequence.

Advantageously, epitope tags are used which can be easily detected and purified by immunological methods. A unique tag sequence is added to the nucleotide sequence by recombinant DNA techniques, creating a fusion protein that can be recognised by an antibody specific for the tag peptide. The major advantage of epitope tagging is the small size of the added peptide sequences, usually 3 to 12 amino acids, which generally have no effect on the biological function of the tagged protein. In addition, for most biochemical applications, the use of epitope tags eliminates the need to generate an antibody to the specific protein being studied.

A preferred tag sequence is the HA tag, which is a nine amino acid peptide sequence (YPYDVPDYA) present in the human influenza virus hemagglutinin protein.

The HA tag is recognised by an anti-HA antibody as described herein. The HA tag has been successfully fused to proteins at their amino terminal end, carboxy terminal end, or at various sites within the target protein sequence. In addition, HA-tagged proteins may be expressed and detected in bacteria, yeast, insect cells, and mammalian cells.

Preferably, the tag sequencers located at the 3' end of the nucleotide sequence.

Preferably, a linker is located between the 3' end of the nucleotide sequence and the tag sequence.

Linker

A linker may separate the polypeptide domain(s) and the Arc DNA binding domain(s).

If more than one Arc DNA binding domain is included in the construct, then a linker may also separate the Arc DNA binding domains.

The sequence of the linker may be based upon those used in the construction of single-chain antigen binding proteins (*Methods Enzymol.* (1991) 203, 36-89). Typically, the sequence will be chosen to maximises flexibility and solubility and allow the introduction of restriction sites for cloning and gene construction. Such sequences may be designed using the methods described in *Biochemistry* (1996) 35, 109-116 and may even comprise the sequences set forth therein.

The linker may comprise any amino acid.

The sequence that joins the Arc DNA binding domain(s) may comprise G and/or S and/or T and/or H or conservative substitutions thereof.

The linker may comprise or consist of the sequence $(G_nS)_n$ and/or $(G_nH)$. The linker may comprise or consist of the sequence $(G_3S)_2$ and/or $(G_3S)_3$. The linker may comprise or consist of the sequence $(G_3S)_2$ and/or $(G_3S)_3$ and/or $(G_3H)$. The linker may comprise or consist of the sequence $(G_3S)_2$ $(G_3H)$. The linker may comprise or consist of the sequence $(G_3S)_3$ $(G_3H)$.

The linker may consist of 2, 3, 4, 5, 6, 7, 8, 9, 10, 11, 12, 13, 14, 15 or 16 or more amino acids. Preferably, the linker consists of 8, 9 or 10 amino acids. Most preferably, the linker consists of 9 amino acids.

A person skilled in the art will appreciate that other suitable sequences may be designed using the methods described in, for example, *Biochemistry* (1996) 35, 109-116.

Nucleotide Sequence

The nucleotide sequence according to the present invention may comprise any nucleic acid (for example, DNA, RNA or any analogue, natural or artificial, thereof).

The DNA or RNA may be of genomic or synthetic or of recombinant origin (e.g. cDNA), or combinations thereof.

The nucleotide sequence may be double-stranded or single-stranded whether representing the sense strand or the antisense strand or combinations thereof. The nucleotide sequence may be a gene.

Preferably, the nucleotide sequence is selected from the group consisting of a DNA molecule, an RNA molecule, a partially or wholly artificial nucleic acid molecule consisting of exclusively synthetic or a mixture of naturally-occurring and synthetic-bases, any one of the foregoing linked to a polypeptide, and any one of the foregoing linked to any other molecular group or construct.

The one or more Arc DNA binding domains, one or more Arc DNA binding sites and at least one polypeptide domain, and optionally, the tag and/or linker sequences, are operably linked.

As used herein, the term "operably linked" refers to a juxtaposition wherein the nucleotide sequences are joined (eg. ligated) together in a relationship that permits them to be expressed as an expression product (eg. a gene product).

The nucleotide sequence may comprise suitable regulatory sequences, such as those required for efficient expression of the gene product, for example promoters, enhancers, translational initiation sequences and the like.

The nucleotide sequence may moreover be linked, covalently or non-covalently, to one or more molecules or structures, including proteins, chemical entities and groups, solid-phase supports and the like.

Expression

Expression, as used herein, is used in its broadest meaning, to signify that a nucleotide sequence is converted into its gene product.

Thus, where the nucleic acid is DNA, expression refers to the transcription of the DNA into RNA; where this, RNA codes for protein, expression may also refer to the translation of the RNA into protein. Where the nucleic acid is RNA, expression may refer to the replication of this RNA into further RNA copies, the reverse transcription of the RNA into DNA and optionally the transcription of this DNA into further RNA molecule(s), as well as optionally the translation of any of the RNA species produced into protein.

Preferably, therefore, expression is performed by one or more processes selected from the group consisting of transcription, reverse transcription, replication and translation.

Expression of the nucleotide sequence may thus be directed into either DNA, RNA or protein, or a nucleic acid or protein containing unnatural bases or amino acids (the gene product), preferably within the microcapsule of the invention, so that the gene product is confined within the same microcapsule as the nucleotide sequence.

Microcapsule

As used herein, the term "microcapsule" refers to a compartment whose delimiting borders restrict the exchange of the components of the molecular mechanisms described herein which allow the sorting of nucleotide sequences according to the specificity of the polypeptide (eg antibody) domains which they encode.

The microcapsule may be a cell—such as a yeast, fungal or bacterial cell. If the cell is a bacterial cell then it may be in the form of a spheroplast. Spheroplasts may be prepared using various methods in the art. By way of example, they may be prepared by resuspending pelleted cells in a buffer containing sucrose and lysozyme.

Preferably, the microcapsule is artificial.

Preferably, the microcapsules used in the methods of the present invention will be capable of being produced in very large numbers, and thereby able to compartmentalise a library of nucleotide sequences which encode a repertoire of polypeptide domains, for example, antibody domains The microcapsules of the present invention require appropriate physical properties to allow them to work successfully.

First, to ensure that the nucleotide sequences and gene products do not diffuse between microcapsules, the contents of each microcapsule must be isolated from the contents of the surrounding microcapsules, so that there is no or little exchange of the nucleotide sequences and gene products between the microcapsules over the timescale of the experiment.

Second, there should be only a limited number of nucleotide sequences per microcapsule. This ensures that the gene product of an individual nucleotide sequence will be isolated from other nucleotide sequences. Thus, coupling between nucleotide sequence and gene product will be highly specific. The enrichment factor is greatest with on average one or fewer nucleotide sequences per microcapsule, the linkage between nucleic acid and the activity of the encoded gene product being as tight as is possible, since the gene product of an individual nucleotide sequence will be isolated from the -products of all other nucleotide sequences. However, even if the theoretically optimal situation of, on average, a single nucleotide sequence or less per microcapsule is not used, a ratio of 5, 10, 50, 100 or 1000 or more nucleotide sequences per microcapsule may prove beneficial in sorting a large library. Subsequent rounds of sorting, including renewed encapsulation with differing nucleotide sequence distribution, will permit more stringent sorting of the nucleotide sequences. Preferably, there is a single nucleotide sequence, or fewer, per microcapsule.

Third, the formation and the composition of the microcapsules must not abolish the function of the machinery for the expression of the nucleotide sequences and the activity of the gene products.

Consequently, any microencapsulation system used should fulfil these three requirements. The appropriate system(s) may vary depending on the -precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closedmembranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed (for example, by digestion of nucleic acids with DNase or RNase) in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme-systems (Chang, 1987; Chang, 1992; Lim, 1984). Alginate/polylysine microcapsules (Lim & Sun, 1980) which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan-monooleate (Span™80; ICI) and t-octylphenoxypolyethoxy-ethanol (Triton X-100, Sigma).

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the nucleotide sequences and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1-957; Dickinson, 1994).

Aqueous microcapsules formed in water-in-oil emulsions are generally stable with little if any exchange of nucleotide sequences or gene products between microcapsules. Additionally, we have demonstrated that several biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of litres (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

The processes of expression must occur within each individual microcapsule provided by the present invention. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. Preferably, the mean volume of the microcapsules is less that $5.2 \times 10^{-16}$ m$^3$, (corresponding to a spherical microcapsule of diameter less than 10 µm, more preferably less than $6.5 \times 10^{-17}$ m$^3$ (5 µm), more preferably about $4.2 \times 10^{-18}$ m$^3$ (2 µm) and ideally about $9 \times 10^{-18}$ m$^3$ (2.6 µm).

The effective DNA or RNA concentration in the microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1-975; Rosenberg et al., 1-975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Qβ replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Even gene amplification techniques requiring thermal cycling such as PCR and LCR could be used if the emulsions and the in vitro transcription or coupled transcription-translation systems are thermostable (for example, the coupled transcription-translation systems could be made from a thermostable organism such as *Thermus aquaticus*).

Increasing the effective local nucleic acid concentration enables larger microcapsules to be used effectively. This allows a preferred practical upper limit to the microcapsule volume of about $5.2 \times 10^{-16}$ m$^3$ (corresponding to a sphere of diameter 10 μm).

The microcapsule size must be sufficiently large to, accommodate all of the required components of the biochemical reactions that are needed to occur within the microcapsule. For example, in vitro, bot transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per microcapsule ($8.33 \times 10^{-22}$ moles). In order to constitute a 2 mM solution, this number of molecules must be contained within a microcapsule of volume $4.17 \times 10^{-19}$ litres ($4.17 \times 10^{-22}$ m$^3$ which if spherical would have a diameter of 93 nm.

Furthermore, particularly in the case of reactions involving translation, it is to be noted that the ribosomes necessary for the translation to occur are themselves approximately 20 nm in diameter. Hence, the preferred lower limit for microcapsules is a diameter of approximately 0.1 μm (100 nm).

Therefore, the microcapsule volume is preferably of the order of between $5.2 \times 10^{-22}$ m$^3$ and $5.2 \times 10^{-16}$ m$^3$ corresponding to a sphere of diameter between 0.1 μm and 10 μm, more preferably of between about $5.2 \times 10^{-19}$ m$^3$ and $6.5 \times 10^{-17}$ m$^3$ (1 μm and 5 μm). Sphere diameters of about 2.6 μm are most advantageous.

It is no coincidence that the preferred dimensions of the compartments (droplets of 2.6 μm mean diameter) closely resemble those of bacteria, for example, *Escherichia* are 1.1-1.5×2.0-6.0 μm rods and *Azotobacter* are 1.5-2.0 μm diameter ovoid cells. In its simplest form, Darwinian evolution is based on a 'one genotype one phenotype' mechanism. The concentration of a single compartmentalised gene, or genome, drops from 0.4 nM in a compartment of 2 μm diameter, to 25 pM in a compartment of 5 μm diameter. The prokaryotic transcription/translation machinery has evolved to operate in compartments of ~1-2 μm diameter, where single genes are at approximately nanomolar concentrations. A singe gene, in a compartment of 2.6 μm diameter is at a concentration of 0.2 nM. This gene concentration is high enough for efficient translation. Compartmentalisation in such a volume also ensures that even if only a single molecule of the gene product is formed it is present at about 0.2 nM, which is important if the gene product is to have a modifying activity of the nucleotide sequence itself. The volume of the microcapsule should thus be selected bearing in mind not only the requirements for transcription and translation of the nucleotide sequence, but also the modifying activity required of the gene product in the method of the invention.

The size of emulsion microcapsules may be varied simply by tailoring the emulsion conditions used to form the emulsion according to requirements of the selection system. The larger the microcapsule size, the larger is the volume that will be required to encapsulate a given nucleotide sequence library, since the ultimately limiting factor will be the size of the microcapsule and thus the number of microcapsules possible per unit volume.

The size of the microcapsules is selected not only having regard to the requirements of the transcription/translation system, but also those of the selection system employed for the nucleotide sequence. Thus, the components of the selection system, such as a chemical modification system, may require reaction volumes and/or reagent concentrations which are not optimal for transcription/translation. As set forth herein, such requirements may be accommodated by a secondary re-encapsulation step; moreover, they may be accommodated by selecting the microcapsule size in order to maximise transcription/translation and selection as a whole. Empirical determination of optimal microcapsule volume and reagent concentration, for example as set forth herein, is preferred.

Preferably, PCR is used to assemble the library, introduce mutations and to amplify the selected genetic elements.

Isolating/Sorting/Selecting

The terms "isolating", "sorting" and "selecting", as wells as variations thereof, are used herein.

"Isolation", according to the present invention, refers to the process of separating an polypeptide domain with a desired specificity from a population of polypeptide domains having a different specificity.

In a preferred embodiment, isolation refers to purification of an polypeptide domain essentially to homogeneity.

"Sorting" of a polypeptide domain refers to the process of preferentially isolating desired polypeptide domains over undesired polypeptide domains. In as far as this relates to isolation of the desired polypeptide domains, the terms "isolating" and "sorting" are equivalent. The method of the present invention permits the sorting of desired nucleotide sequences from pools (libraries or repertoires) of nucleotide sequences which contain the desired nucleotide sequence.

"Selecting" is used to refer to the process (including the sorting process) of isolating a polypeptide domain according to a particular property thereof.

In a highly preferred application, the method of the present invention is useful for sorting libraries of polypeptide (eg. antibody) domain nucleotide sequences. The invention accordingly provides a method, wherein the polypeptide domain nucleotide sequences are isolated from a library of nucleotide sequences encoding a repertoire of polypeptide domains, for example, antibody domains. Herein, the terms "library", "repertoire" and "pool" are used according to their ordinary signification in the art, such that a library of nucleotide sequences encode a repertoire of gene products. In general, libraries are constructed from pools of nucleotide sequences and have properties, which facilitate sorting.

Method of In Vitro Evolution

According to a further aspect of the present invention, therefore, there is provided a method of in vitro evolution comprising the steps of: (a) selecting one or more polypeptide domains from a library according to the present invention; (b) mutating the selected polypeptide domain(s) in order to generate a further library of nucleotide sequences encoding a repertoire of gene products; and (c) iteratively repeating steps (a) and (b) in order to obtain a polypeptide domain with enhanced specificity.

Mutations may be introduced into the nucleotide sequences using various methods that are familiar to a person skilled in the art—such as the polymerase chain reaction (PCR). PCR used for the amplification of DNA sequences between rounds of selection is known to introduce, for example, point mutations, deletions, insertions and recombinations.

In a preferred aspect, the invention permits the identification and isolation of clinically or industrially useful polypeptide domains. In a further aspect of the invention, there is provided a polypeptide domain when isolated, obtained or obtainable by the method of the invention.

The selection of suitable encapsulation conditions is desirable. Depending on the complexity and size of the library to be screened, it may be beneficial to set up the encapsulation procedure such that 1 or less than 1 nucleotide sequence is encapsulated per microcapsule. This will provide the greatest power of resolution. Where the library is larger and/or more complex, however, this may be impracticable; it may be preferable to encapsulate nucleotide sequences together and rely on repeated application of the method of the invention to achieve sorting of the desired activity. A combination of encapsulation procedures may be used to obtain the desired enrichment.

Theoretical studies indicate that the larger the number of nucleotide sequence variants created the more likely it is that a molecule will be created with the properties desired (see Perelson and Oster, 1979 for a description of how this applies to repertoires of antibodies). Recently it has also been confirmed practically that larger phage-antibody repertoires do indeed give rise to more antibodies with better binding affinities than smaller repertoires (Griffiths et al., 1994). To ensure that rare variants are generated and thus are capable of being selected, a large library size is desirable. Thus, the use of optimally small microcapsules is beneficial.

In addition to the nucleotide sequences described above, the artificial microcapsules will comprise further components required for the sorting process to take place. Other components of the system will for example comprise those necessary for transcription and/or translation of the nucleotide sequence. These are selected for the requirements of a specific system from the following; a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, to allow selection of the modified gene product.

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

The in vitro translation system will usually comprise a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

After each round of selection the enrichment of the pool of nucleotide sequences for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

The invention moreover relates to a method for producing a polypeptide domain, once a nucleotide sequence encoding the gene product has been sorted by the method of the invention. Clearly, the nucleotide sequence itself may be directly expressed by conventional means to produce the polypeptide domain. However, alternative techniques may be employed, as will be apparent to those skilled in the art. For example, the genetic information incorporated in the polypeptide domain may be incorporated into a suitable expression vector, and expressed therefrom.

The invention also describes the use of conventional screening techniques to identify compounds which are capable of interacting with the polypeptide domains identified by the invention. In preferred embodiments, a polypeptide domain encoding nucleic acid is incorporated into a vector, and introduced into suitable host cells to produce transformed cell lines that express the polypeptide domain. The resulting cell lines can then be produced for reproducible qualitative and/or quantitative analysis of the effect(s) of potential drugs affecting polypeptide domain specificity. Thus polypeptide domain expressing cells may be employed for the identification of compounds, particularly small molecular weight compounds, which modulate the function of the polypeptide domains. Thus, host cells expressing polypeptide domains are useful for drug screening and it is a further object of the present invention to provide a method for identifying compounds which modulate the activity of the polypeptide domain, said method comprising exposing cells containing heterologous DNA encoding polypeptide domains, wherein said cells produce functional polypeptide domains, to at least one compound or mixture of compounds or signal whose ability to modulate the activity of said polypeptide domain is sought to be determined, and thereafter monitoring said cells for changes caused by said modulation. Such an assay enables the identification of modulators, such as agonists, antagonists and allosteric modulators, of the polypeptide domain. As used herein, a compound or signal that modulates the activity of a polypeptide domain refers to a compound that alters the specificity of the polypeptide domain in such a way that the activity of the polypeptide domain is different in the presence of the compound or signal (as compared to the absence of said compound or signal).

Cell-based screening assays can be designed by constructing cell lines in which the expression of a reporter protein, i.e. an easily assayable protein, such as β galactosidase, chloramphenicol acetyltransferase (CAT) or luciferase, is dependent on the polypeptide domain. Such an assay enables the detection of compounds that directly modulate the polypeptide domain specificity, such as compounds that antagonise polypeptide domains, or compounds that inhibit or potentiate other cellular functions required for the activity of the polypeptide domains.

The present invention also provides a method to exogenously affect polypeptide domain dependent processes occurring in cells. Recombinant polypeptide domain producing host cells, e.g. mammalian cells, can be contacted with a test compound, and the modulating effect(s) thereof can then be evaluated by comparing the polypeptide domain-mediated response in the presence and absence of test compound, or relating the polypeptide domain-mediated response of test cells, or control cells (i.e., cells that do not express polypeptide domains), to the presence of the compound.

Selection Procedure

In accordance with the present invention, only polypeptide domains that can associate with the encoding DNA are selected thus allowing the establishment of a phenotype-genotype link between the gene product and the encoding gene. The nucleotide sequence will thus comprise a nucleic acid encoding a polypeptide domain linked to the polypeptide domain gene product. Thus, in the context of the present invention, the nucleotide sequence will comprise a nucleic acid encoding a polypeptide domain linked to the polypeptide domain via an association between the Arc DNA binding site and the Arc DNA binding domain.

Since the polypeptide domain-Arc DNA binding domain gene product has affinity for the DNA binding site, the Arc DNA binding domain gene product will bind to the Arc DNA binding site and become physically linked to the nucleotide sequence which is covalently linked to its encoding sequence.

At the end of the reaction, all of the microcapsules are combined, and all nucleotide sequences and gene products are pooled together in one environment. Nucleotide sequences encoding polypeptide (eg. antibody) domains that exhibit the desired binding—such as the native binding—can be selected by various methods in the art—such as affinity purification using a molecule that specifically binds to, or reacts specifically with, the polypeptide domain.

Sorting by affinity is dependent on the presence of two members of a binding pair in such conditions that binding may occur.

In accordance with the present invention, binding pairs that may be used in the present invention include an antigen capable of binding specifically to the polypeptide (eg. antibody) domain. The antigen may be a polypeptide, protein, nucleic acid or other molecule.

The term "binding specifically" means that the interaction between the polypeptide (eg. antibody) domain and the antigen are specific, that is, in the event that a number of molecules are presented to the polypeptide domain, the latter will only bind to one or a few of those molecules presented. Advantageously, the polypeptide domain-antigen interaction will be of high affinity.

Using affinity purification, a solid phase immunoabsorbant is used—such as an antigen covalently coupled to an inert support (eg. cross linked dextran beads). The immunoabsorbant is placed in a column and the polypeptide domain is run in. Antibody to the antigen binds to the column while unbound antibody washes through. In the second step, the column is eluted to obtain the bound antibody using a suitable elution buffer, which dissociates the antigen-antibody bound.

Suitably, streptavidin-coated paramagnetic microbeads (e.g. Dynabeads, Dynal, Norway), coated with biotinylated target protein, are used as the solid phase support to capture those protein-DNA complexes which display desired activity.

More suitably, streptavidin-coated PCR tubes (e.g. Strep ThermoFast 96, ABgene, U.K.), coated with biotinylated target protein are used as the solid phase support to capture those protein DNA complexes which display desired activity.

Various immunoabsorbants for affinity purification are known in the art, for example, protein A, protein L, protein G.

Preferably, for model selection purposes, the immunoabsorbant is protein L.

Protein L exhibits a unique combination of species-specific, immunoglobulin-binding characteristics and high affinity for many classes of antibodies and antibody fragments. Protein L is a recombinant form of a *Peptostreptococcus magnus* cell wall protein that binds immunoglobulins (Ig) through light-chain interactions that do not interfere with the Ig antigen-binding site. A majority of Ig sub-classes, including IgG, IgM, IgA, IgD, IgE, and IgY, from human, mouse, rat, rabbit, and chicken possess light chains and can thus be bound with high affinity by Protein L. Protein L also binds Ig fragments, including scFv and Fab.

Commercially available kits can be obtained from, for example, Clonetech and SigmaAldrich.

Polypeptide domains binding to other molecules of interest—such as proteins, haptens, oligomers and polymers—can be isolated by coating them onto the chosen solid supports instead of protein L.

Multi-Step Procedure

It will be appreciated that according to the present invention, it is not necessary for all the processes of transcription/replication and/or translation, and selection to proceed in one single step, with all reactions taking place in one microcapsule. The selection procedure may comprise two or more steps.

First, transcription/replication and/or translation of each nucleotide sequence of a nucleotide sequence library may take place in a first microcapsule. Each polypeptide domain is then linked to the nucleotide sequence, which encoded it (which resides in the same microcapsule). The microcapsules are then broken, and the nucleotide sequences attached to their respective polypeptide domains are optionally purified. Alternatively, nucleotide sequences can be attached to their respective gene products using methods which do not rely on encapsulation. For example phage display (Smith, G. P., 1985), polysome display (Mattheakkis et al., 1994), RNA-peptide fusion (Roberts and Szostak, 1997) or lac repressor peptide fusion (Cull, et al., 1992).

In the second step of the procedure, each purified nucleotide sequence attached to its polypeptide domain is put into a second microcapsule containing components of the reaction microcapsules are again broken and the modified nucleotide sequences are selected. In the case of complicated multistep reactions in which many individual components and reaction steps are involved, one or more intervening steps may be performed between the initial step of creation and linking of polypeptide domain to nucleotide sequence, and the final step of generating the selectable change in the nucleotide sequence.

Amplification

According to a further aspect of the present invention, the method comprises the further step of amplifying the nucleotide sequences bound to the immunosorbent. Selective amplification may be used as a means to enrich for nucleotide sequences encoding the desired polypeptide domain.

In all the above configurations, genetic material comprised in the nucleotide sequences may be amplified and the process repeated in iterative steps. Amplification may be by the polymerase chain reaction (Saiki et al., 1988) or by using one of a variety of other gene amplification techniques including; Qβ replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

Preferably, amplification is performed with PCR. More preferably, amplification is performed with PCR using nested forward primers AS12-AS16, AS29 and reverse primers AS17-AS22, AS153.

Typically the amplification comprises an initial denaturation at 94° C. for 2 min, followed by 30 or 35 cycles of denaturation at 94° C. for 15 sec, annealing at 60° C. for 30 sec, extension at 72° C. for two minutes and a final extension at 72° C. for 5 min.

Construct

The term "construct"—which is synonymous with terms such as "conjugate", "cassette" and "hybrid"—includes a nucleic acid sequence directly or indirectly attached to a promoter. An example of an indirect attachment is the provision of a suitable spacer group such as an intron sequence, intermediate the promoter and the nucleotide sequence. The same is true for the term "fused" in relation to the present invention, which includes direct or indirect attachment.

Preferably, the promoter is a T7 promoter. More preferably, the T7 promoter is upstream of the nucleotide sequence.

The construct may even contain or express a marker, which allows for the selection of the construct in, for example, a bacterium.

Vectors

The nucleotide sequences of the present invention may be present in a vector.

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another such as from an *E. coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

The vectors may be transformed into a suitable host cell to provide for expression of a polypeptide.

The vectors may be for example, plasmid, virus or phage vectors provided with an origin of replication, optionally a promoter for the expression of the said polynucleotide and optionally a regulator of the promoter.

The vectors may contain one or more selectable marker nucleotide sequences. The most suitable selection systems for industrial micro-organisms are those formed by the group of selection markers which do not require a mutation in the host organism. Examples of fungal selection markers are the nucleotide sequences for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance nucleotide sequence (this may also be used in yeast, but not in filamentous fungi), the ampicillin resistance nucleotide sequence (*E. coli*), the neomycin resistance nucleotide sequence (*Bacillus*) and the *E. coli* uidA nucleotide sequence, coding for β-glucuronidase (GUS).

Vectors may be used in vitro, for example for the production of RNA or used to transfect or transform a host cell.

Thus, polynucleotides may be incorporated into a recombinant vector (typically a replicable vector), for example a cloning or expression vector. The vector may be used to replicate the nucleic acid in a compatible host cell.

Genetically engineered host cells may be used for expressing an amino acid sequence (or variant, homologue, fragment or derivative thereof).

Expression Vectors

The nucleotide sequences of the present invention may be incorporated into a recombinant replicable vector. The vector may be used to replicate and express the nucleotide sequence in and/or from a compatible host cell. Expression may be controlled using control sequences, which include promoters/enhancers and other expression regulation signals. Prokaryotic promoters and promoters functional in eukaryotic cells may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences, which direct secretion of the substance coding sequences through a particular prokaryotic or eukaryotic cell membrane.

Fusion Proteins

Amino acid sequences of the present invention may be produced as a fusion protein, for example to aid in extraction and purification, using a tag sequence.

Host Cells

As used herein, the term "host cell" refers to any cell that may comprise the nucleotide sequence of the present invention and may be used to express the nucleotide sequence.

Thus, in a further embodiment the present invention provides host cells transformed or transfected with a polynucleotide that is or expresses the nucleotide sequence of the present invention. Preferably, said polynucleotide is carried in a vector for the replication and expression of polynucleotides. The cells will be chosen to be compatible with the said vector and may for example be prokaryotic (for example bacterial), fungal, yeast or plant cells.

The gram-negative bacterium *E. coli* is widely used as a host for heterologous nucleotide sequence expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the nucleotide sequencera *Streptomyces* and *Pseudomonas*. Depending on the nature of the polynucleotide and/or the desirability for further processing of the expressed protein, eukaryotic hosts such as yeasts or other fungi may be preferred.

The use of host cells—such as yeast, fungal and plant host cells—may provide for posttranslational modifications (e.g. myristoylation, glycosylation, truncation, lapidation and tyrosine, serine or threonine phosphorylation) as may be needed to confer optimal biological activity on recombinant expression products of the present invention.

Regulatory Sequences

In some applications, polynucleotides may be linked to a regulatory sequence, which is capable of providing for the expression of the nucleotide sequence, such as by a chosen host cell. By way of example, the present invention covers a vector comprising the nucleotide sequence of the present invention operably linked to such a regulatory sequence, i.e. the vector is an expression vector.

The term "regulatory sequences" includes promoters and enhancers and other expression regulation signals.

The term "promoter" is used in the normal sense of the art, e.g. an RNA polymerase binding site.

Enhanced expression of polypeptides may be achieved by the selection of heterologous regulatory regions, e.g. promoter, secretion leader and terminator regions, which serve to increase expression and, if desired, secretion levels of the protein of interest from the chosen expression host and/or to provide for the inducible control of expression.

Aside from the promoter native to the nucleotide sequence encoding the polypeptide, other promoters may be used to direct expression of the polypeptide. The promoter may be selected for its efficiency in directing the expression of the polypeptide in the desired expression host.

In another embodiment, a constitutive promoter may be selected to direct the expression of the polypeptide. Such an expression construct may provide additional advantages since it circumvents the need to culture the expression hosts on a medium containing an inducing substrate.

Examples of strong constitutive and/or inducible promoters which are preferred for use in fungal expression hosts are those which are obtainable from the fungal nucleotide sequences for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the gIaA nucleotide sequence), acetamidase (amdS) and glyceraldehyde-3-phosphate dehydrogenase (gpd) promoters.

Examples of strong yeast promoters are those obtainable from the nucleotide sequences for alcohol dehydrogenase, lactase, 3-phosphoglycerate kinase and triosephosphate isomerase.

Examples of strong bacterial promoters are the α-amylase and SP02 promoters as well as promoters from extracellular protease-nucleotide sequences.

Hybrid promoters may also be used to improve inducible regulation of the expression construct.

The promoter can additionally include features to ensure or to increase expression in a suitable host. For example, the feature can be conserved regions such as a Pribnow Box, a TATA box or T7 transcription terminator. The promoter may even contain other sequences to affect (such as to maintain, enhance, decrease) the levels of expression of a nucleotide sequence. Suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217-225; and Dawson Plant Mol. Biol. 23 [1993] 97).

If the nucleotide sequence comprises a regulatory sequence, then the regulatory sequence may be located upstream of the one or more DNA binding sites, one or more Arc DNA binding domains, polypeptide domain and linker(s).

The regulatory sequence may be located upstream of the one or more Arc DNA binding domains, polypeptide domain and linker(s).

The regulatory sequence may be located upstream of the one or more DNA binding sites, and downstream of the one or more Arc DNA binding domains, polypeptide domain and linker(s).

Variants/Homologues/Derivatives

The present invention encompasses the use of variants, homologues, derivatives and/or fragments of the nucleotide and/or amino acid sequences described herein.

The term "variant" is used to mean a naturally occurring polypeptide or nucleotide sequences which differs from a wild-type sequence.

The term "fragment" indicates that a polypeptide or nucleotide sequence comprises a fraction of a wild-type sequence. It may comprise one or more large contiguous sections of sequence or a plurality of small sections. The sequence may also comprise other elements of sequence, for example, it may be a fusion protein with another protein. Preferably the sequence comprises at least 50%, more preferably at least 65%, more preferably at least 80%, most preferably at least 90% of the wild-type sequence.

The term "homologue" means an entity having a certain homology with the subject amino acid sequences and the subject nucleotide sequences. Here, the term "homology" can be equated with "identity".

In the present context, a homologous sequence is taken to include an amino acid sequence, which may be at least 75, 85 or 90% identical, preferably at least 95 or 98% identical to the subject sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence, which may be at least 75, 85 or 90% identical, preferably at least 95 or 98% identical to the subject sequence.

Although homology can also be considered in terms of similarity (i.e. amino acid residues having similar chemical properties/functions), in the context of the present invention it is preferred to express homology in terms of sequence identity.

Homology comparisons may be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties well of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1994, *Nucleic Acids Research* 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix—such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example, according to the Table below. Amino acids in the same block in the second column and preferably in the same line in the third column may be substituted for each other:

| ALIPHATIC | Nonpolar | G A P |
|---|---|---|
|  |  | I L V |
|  | Polar - uncharged | C S T M |
|  |  | N Q |
|  | Polar - charged | D E |
|  |  | K R |
| AROMATIC |  | H F W Y |

The present invention also encompasses homologous substitution (substitution and replacement are both used herein to mean the interchange of an existing amino acid residue, with an alternative residue) may occur i.e. like-for-like substitution—such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (Hereinafter referred to as B), norleucine ornithine (hereinafter referred to as O), pyriylalanine, thienylalanine, naphthylalanine and phenylglycine.

Replacements may also be made by -unnatural amino acids include; alpha* and alpha-disubstituted* amino acids, N-alkyl amino acids*, lactic acid*, halide derivatives of natural amino acids—such as trifluorotyrosine*, p-Cl-phenylalanine*, p-Br-phenylalanine*, p-T-phenylalanine*, L-allylglycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone#*, L-norleucine*, L-norvaline*, p-nitro-L-phenylalanine*, L-hydroxyproline#, L-tlioproline*, methyl derivatives of phenylalanine (Phe)—such as 4-methyl-Phe*, pentamethyl-Ple*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid * and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups—such as methyl, ethyl or propyl groups—in addition to amino acid spacers—such as glycine or β-alanine residues. A further form of variation involves the presence of one or more amino acid residues in peptoid form will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example, Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences may be modified by any method available in the art. Such modifications may be carried out to enhance the in vivo activity or life span of nucleotide sequences useful in the present invention.

The present invention may also involve the use of nucleotide sequences that are complementary to the nucleotide sequences or any derivative, fragment or derivative thereof. If the sequence is complementary to a fragment thereof then that sequence can be used as a probe to identify similar coding sequences in other organisms etc.

Preferably, the resultant nucleotide sequence encodes an amino acid sequence that has the same activity. The resultant nucleotide sequence may encode an amino acid sequence that has the same activity, but not necessarily the same degree of activity.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons;

New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The invention will now be further described by way of Examples, which are meant to serve to assist one of ordinary skill in the art in carrying out the invention and are not intended in any way to limit the scope of the invention.

EXAMPLES

Example 1

In Vitro Expression Vectors and Constructs pIE2

Genetic elements for the in vitro expression of domain antibodies in fusion to the N-terminus of DNA-binding domains are based on the pIE2 in vitro expression vector (FIG. 1A). pIE2 is assembled by ligating the DNA duplex formed from the annealed phosphorylated oligonucleotides AS5 and AS6 into the gel purified Nco I/Not I-cut pIE1 vector. pIE1 is assembled by ligating the DNA duplex formed from the annealed phosphorylated oligonucleotides AS1 and AS2 is into gel purified NcoI/BamHI-cut pIVEX2.2b Nde (Roche) in vitro expression vector. Typically both oligonucleotides used in a reaction are phosphorylated simultaneously in 50 µl volume at 2 µM concentration using 5 units of T4 polynucleotide kinase (NEB) in T4 DNA ligase buffer (NEB). Polynucleotide kinase is inactivated by 5 min incubation of the reaction mix at 95° C., followed by 30 min cooling step to 40° C. to allow the annealing of the oligonucleotides to take place. 0.1 µl aliquot of the annealed phosphorylated DNA duplex is added to 100 ng of digested and phosphorylated vector and ligated for 1 h at room temperature in 5 µl volume using 50 units of T4 DNA ligase (NEB). 0.5 µl aliquots of the ligation reaction are thereafter used to transform 5 µl aliquots of supercompetent XL-10 *E. coli* cells (Stratagene) according to the manufacturer's instructions. The sequences of the inserted fragments are verified by DNA sequencing of plasmid DNA minipreps (Qiagen) prepared from overnight cultures.

pIE3

Genetic elements for the in vitro expression of domain antibodies in fusion to the C-terminus of DNA-binding domains are based on the pIE3 in vitro expression vector (FIG. 1B). pIE3 is assembled by ligating the DNA duplex formed from the annealed phosphorylated oligonucleotides AS93 and AS94 into the gel purified Nco I/BamH I-cut vector pIE2, as described in Example 1.

The following in vitro expression constructs with Arc operator sites are used.

pIE2a and pIE3a-series constructs are based on the pIE2 and pIE3 vectors respectively, with one Arc operator site inserted into a unique Bgl II-site just upstream of the T7 promoter. The Arc operator motif was assembled from annealed phosphorylated oligonucleotides AS60/AS61 and ligated Bgl II-cut CIAP-dephosphorylated series pIE2 or pIE3 vectors respectively.

Figure 2:
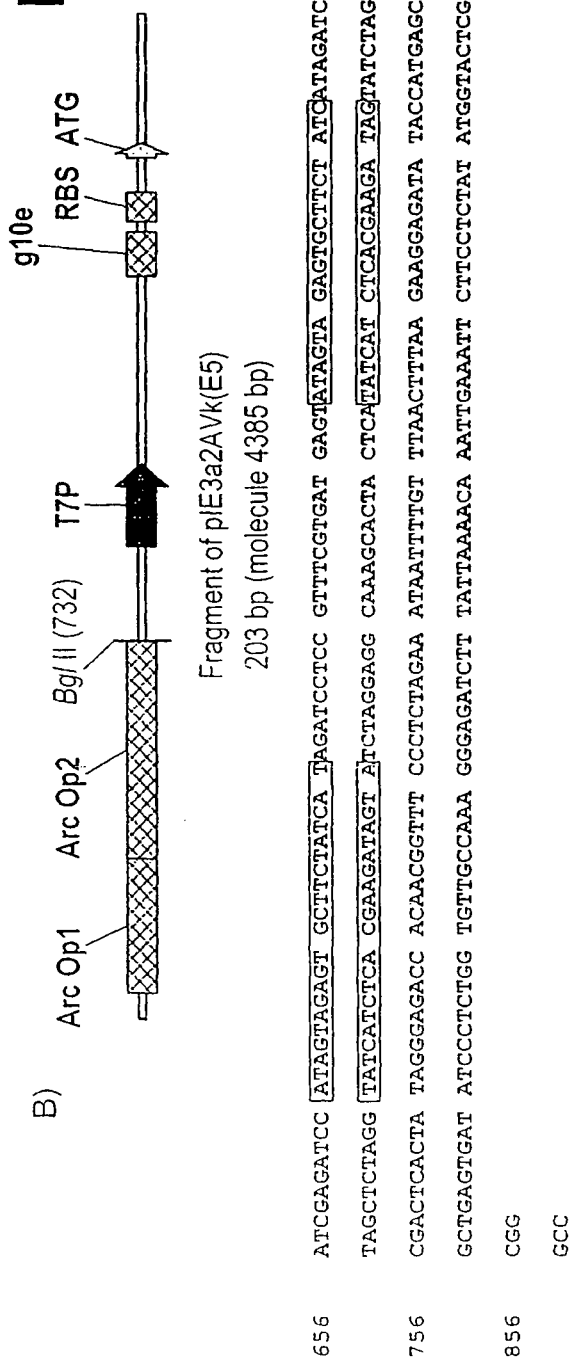
FIG. 2 Multiple Arc operator sites can be inserted into pIE2 and pIE3 series vectors to harness the potential of avidity effect from the display of multiple copies of the dAb-Arc fusion protein. As an example, the Arc operator regions of: A) pIE3a, B) pIE3a<2>, C) pIE3a<3> and D) pIE3a<4> series of vectors are shown. The highlighted region is the Arc operator motif, hi pIE2 series of vectors the Arc operator regions are identical to those in pIE3-series of vectors. The sequences shown correspond to SEQ ID NOs 61-64.
Figure 2:
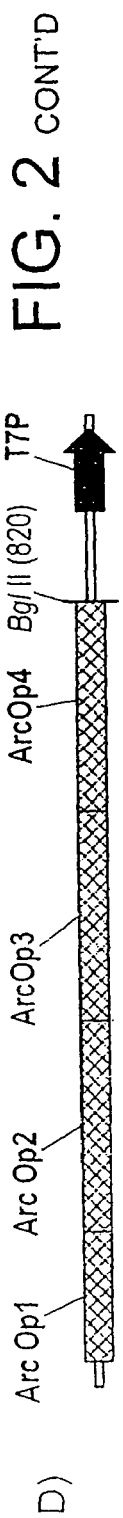

A clone sequenced with primer AS16, where the insert orientation leaves Bgl II site upstream of the Arc operator insert, i.e. closer to T7 promoter, is adopted for future work (FIG. 2A).

More Arc operator sites can be inserted into the vectors by cutting the construct with Bgl II and inserting the next copy of the operator site, assembled from the annealed phosphorylated oligonucleotides AS175/AS176 (FIGS. 2B-D).

Arc Repressor Constructs

The single-chain Arc dimer is assembled as follows. First, the GS linker is assembled by inserting synthetic DNA fragment assembled from annealed phosphorylated oligonucleotides AS51/AS52 into gel purified BamH I/Xho I-cut pBS (Stratagene) cloning vector, yielding pBS-GS vector.

Phage P22 Arc Repressor

The monomer is assembled as follows. 10-cycle PCR overlap extension reactions using phosphorylated oligonucleotides AS53, AS54 and AS62 is performed and the PCR profile 15 sec at 94 C, 30 sec at 55 C and 1 min at 72 C, followed by 25 cycles of amplification using the same cycling profile and primers AS53 and AS59. The PCR-assembled Arc monomer is thereafter cloned into pTOPO-TA (Invitrogen) and sequenced. Arc monomer is excised from pTOPO-TA/Arc by Nde I/Nar I digest and subcloned into Nde I/Nar I-cut GS linker in pBS/GS, yielding pBS/Arc.

Figure 4:
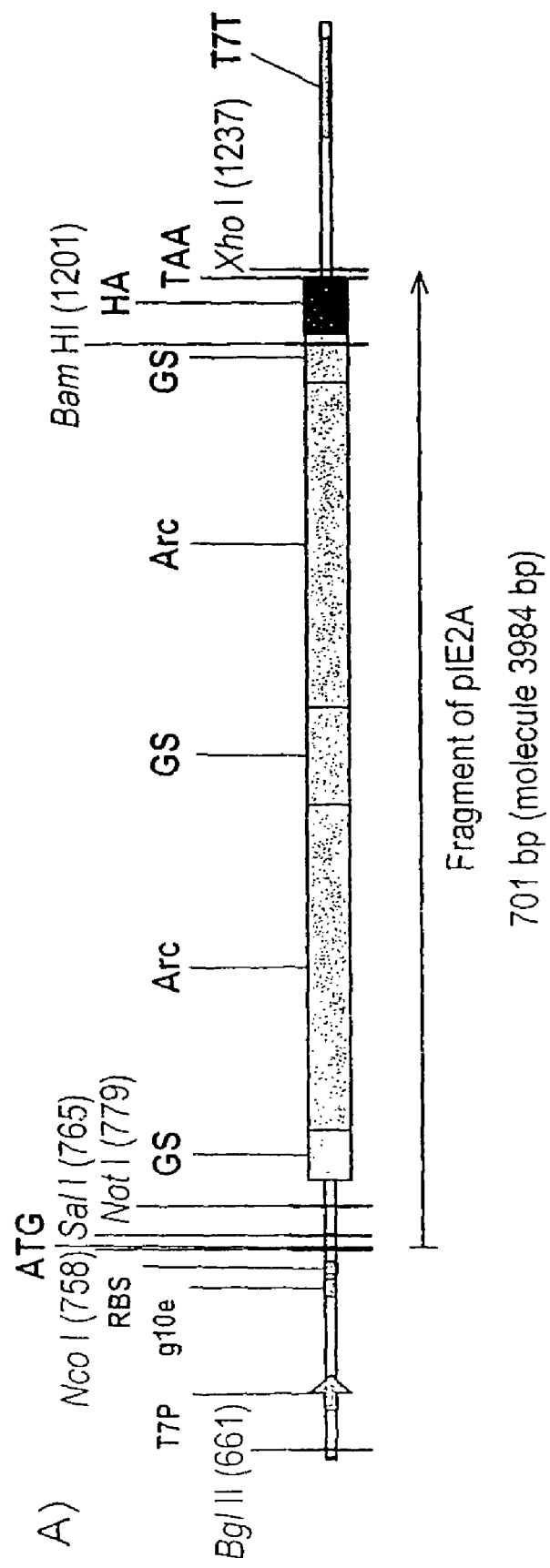
FIG. 4 pIE2-series of vectors are designed to accept the antibody domain in fusion to the N-terminus of scArc, separated by a flanking GS-linker region: A) domain structure of pIE2A construct, B) The expression cassette of pIE2A construct. pIE3-series of vectors are designed to accept the antibody domain in fusion to the C-terminus of scArc, separated by a flanking GS-linker region: A) domain structure of pIE3A construct, B) The expression cassette of pIE3A construct. The proteins expressed as both kinds of fusion proteins are always HA-tagged at the C-terminus. The sequences shown correspond to SEQ ID NOs 67-70.

Single-Chain Arc Dimer (scArc) is assembled by subcloning the BamH I/Bgl II-cut, GS-flanked, Arc monomer into the upstream Bgl II site of the existing GS-flanked Arc monomer in an other ariquot of pBS/Arc plasmid, yielding pBS/scArc (FIG. 3). The resulting single-chain construct has two Arc monomers separated by the $(G_3S)_3(G_3H)$ linker and is flanked by $(G_3S)_2$ linker at the C-terminus and $G_3SG_3H$ linker at the N-terminus. scArc can be released from pBS/scArc by BamH I/Bgl II digest and cloned into the BamH I site of pIE2 or pIE3 series vectors for assembling the fusion constructs with domain antibodies at the N- or C-terminus of the DNA-binding domain, respectively yielding constructs pIE2A and pIE3A (FIG. 4). The antibody domain constructs expressed in both N- and C-terminal fusions to scArc DNA-binding domain are always HA-tagged at the C-terminus of the protein.

scArc Fusion Constructs with $V_\kappa$-domain antibody (dAb)

Figure 5:
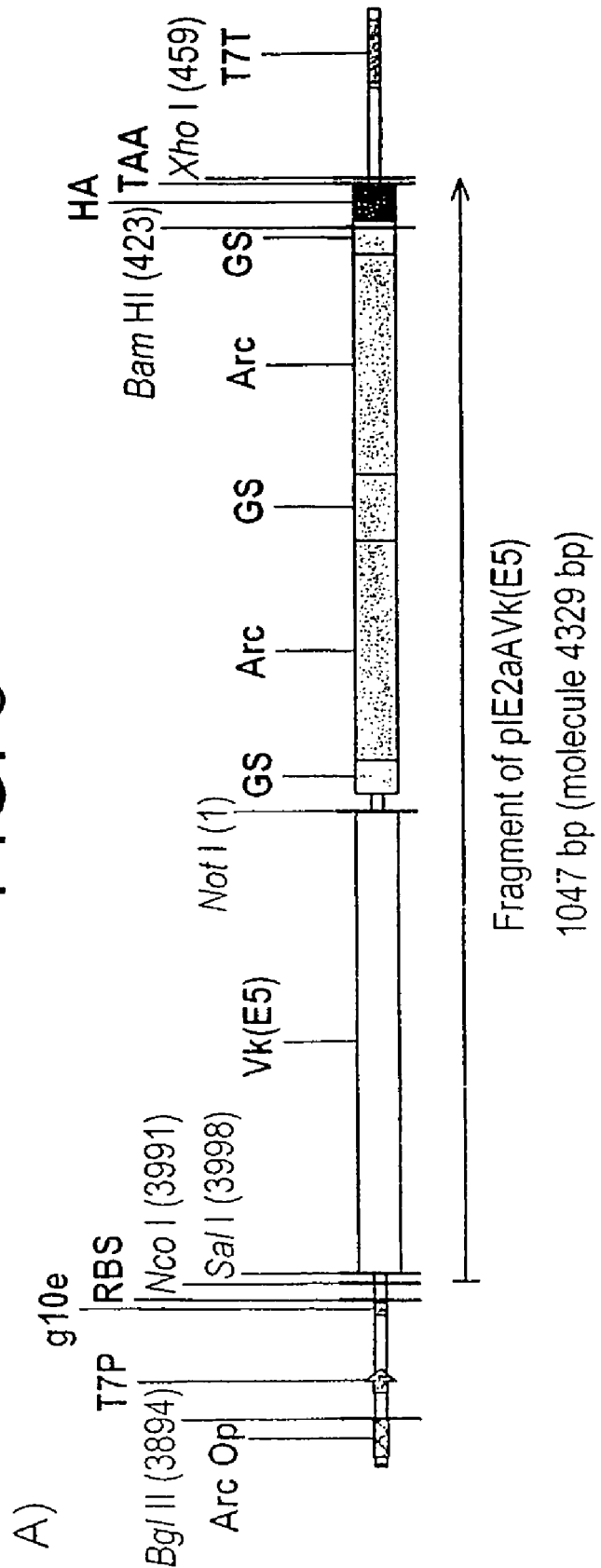
FIG. 5 The expression constructs of Vk(E5) dAb fusion protein with scArc repressor. A) The domain structure of Vlc fusion to the N-terminus of scArc in vector pIE2aAVk(E5) and its associated nucleotide sequence (B). C) The domain structure of Vk fusion to the C-terminus of scArc in vector pIE3aAVk(E5) and its associated nucleotide sequence (D). The Arc operator site that binds the DNA-binding domain of the fusion protein is shadowed. The sequences shown correspond to SEQ ID NOs 71-74.
Figure 5:
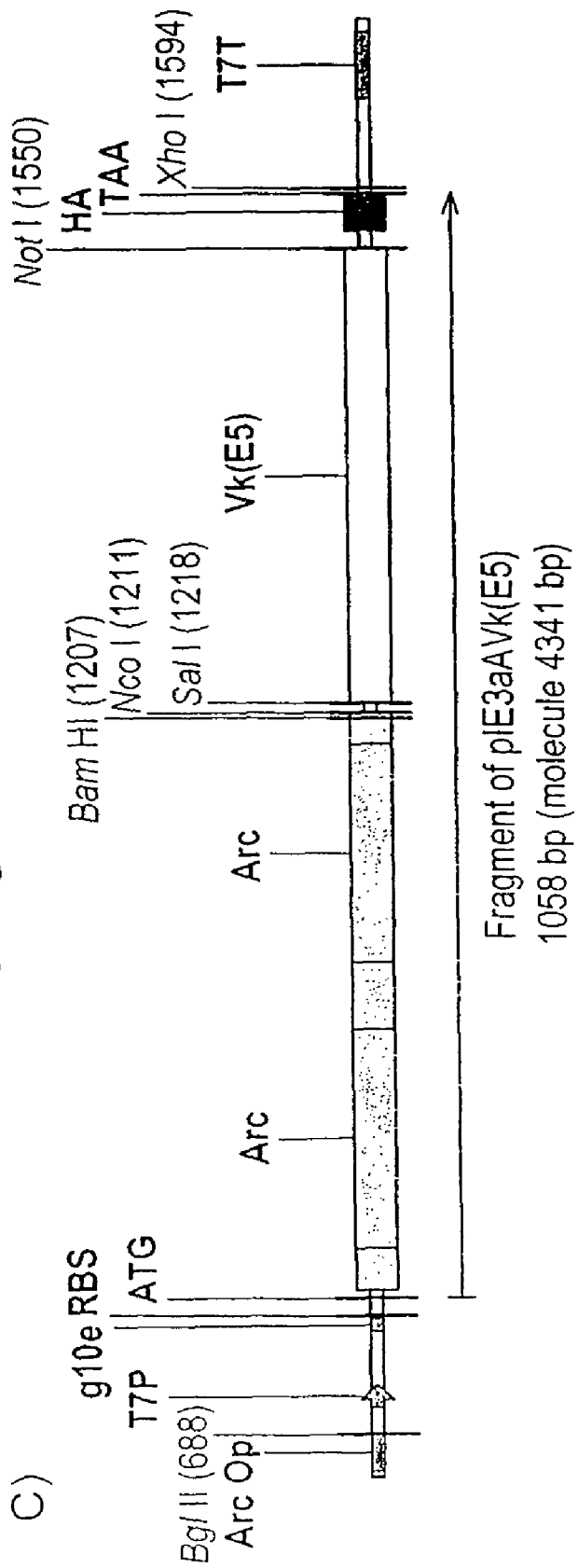

Anti-β-galactosidase $V_\kappa$-clone E5 can be cloned into the Nco I/Not I cut pIE2A and pIE3A-based vectors already harbouring the scArc construct at the BamH I and zero, one, two, three or four Arc operators inserted into the Bgl II site. As an example, fusion constructs of $V_\kappa$(E5) to the N-terminus of scArc (pIE2A-series), as well as to the C-terminus of scArc pIE3A-series), are shown on FIG. 5 with a single copy of Arc operator inserted into the Bgl II site present upstream of the T7 promoter, yielding constructs pIE2aAV$_\kappa$(E5) and pIE3aAV$_\kappa$(E5), respectively.

It can be expected that more than one in vitro expressed scArc-V$_\kappa$(E5) molecule will bind the genetic element within the compartment if the number of Arc operator sites is increased, leading potentially to the formation complexes capable of engaging in polyvalent interactions with the target molecule through the associated Vκ domains. Therefore, the expression constructs with $V_\kappa$(E5) fused both to the N- and C-terminus of scArc were prepared harbouring also two, three and four copies of Arc operator, allowing up to octavalent interaction with the target molecule. Control constructs pIE2AV$_\kappa$(E5) and pIE3AV$_\kappa$(E5) that express the fusion protein, but do not have the Arc operator present, were also assembled. The distance between the operator sites was chosen to be 23 bp, corresponding approximately to the two helical turns of the DNA helix, ensuring that all bound $V_\kappa 0$ moieties of the bound scArc-V$_\kappa$ fusion protein would be exposed in the same direction, allowing simultaneous multivalent contact with any solid surface mobilised target molecules. The distance between the Arc operator sites is approximately 7 nm.

Expression construct with two Arc operators pIE3a$^2$AV$_\kappa$(E5) can be prepared by inserting the second Arc operator, prepared from annealed phosphorylated oligonucleotides AS175 and AS176, into pIE3aAV$_\kappa$(E5) linearized with Bgl II (NEB) and dephosphorylated with alkaline phosphatase (Roche).

Expression construct with three Arc operators pIE3a$^3$AV$_\kappa$(E5) can be prepared by inserting the third-Arc operator, prepared from annealed phosphorylated oligonucleotides AS175 and AS176, into p-IE3a$^2$AV$_\kappa$(E5) linearized with Bgl II (NEB) and dephoshorylated with alkaline phosphatase (Roche).

Expression construct with four Arc operators pIE3a$^4$AV$_\kappa$(E5) can be prepared by inserting the third Arc operator, prepared from annealed phosphorylated oligonucleotides AS175 and AS176, into pIE3a$^3$AV$_\kappa$(E5) linearized with Bgl II (NEB) and dephoshorylated with alkaline phosphatase (Roche).

Expression constructs pIE2a$^2$AV$_\kappa$(E5), pIE2a$^3$AV$_\kappa$(5) and pIE2a$^4$AV$_\kappa$(E5) can be assembled similarly to constructs pIE3a$^2$AV$_\kappa$(E5), pIE3a$^3$AV$_\kappa$(E5) and pIF3a$^4$AV$_\kappa$(E5), i.e. by inserting a synthetic DNA duplex, encoding an Arc operator site and formed from the annealed phosphorylated oligonucleotides AS175 and AS176, into a recipient vector linearized with Bgl II (NEB) and dephoshorylated with calf intestine alkaline phosphatase (Roche).

Example 2

The Formation of Protein-DNA Complex Between Genetic Elements and their Encoded Protein Products Genotype-phenotype linkage involving the scArc-V$_\kappa$(E5) variants requires that the in vitro expressed protein binds to one or more Arc operator sites on the genetic element used for its expression. The formation of such protein-DNA complexes can be assayed using affinity reagents interacting with the protein component of the complex whilst detecting the amount of co-captured DNA by PCR, for example.

The DNA-binding activity of HA-tagged scArc repressor, as expressed from the pIE2 and pIE3-derived expression constructs, can be assayed by PCR, for example, as outlined on FIG. 6. This assay measures the amount of scArc-bound genetic elements in the tube when the in vitro translation pros has been allowed to interact with biotinylated molecules immobilized into streptavidin-coated PCR tubes (Strep ThermoFast 96, ABgene).

The DNA template for the in vitro translation experiments is prepared by PCR using protocol 25X60C2M. In 25X60C2M protocol 50 μl PCR reactions contain 200 μM each of dATP dTTP dGTP dCTP (Amersham), 300 nM forward and reverse primers AS11+AS17, 10 ng plasmid DNA template and 1 U pf SuperTaq DNA polymerase (HT Biotechnology) in 1× polymerase Buffer (HT Biotechnology). Initial denaturation at 94° C. for 2 min is followed by 25 cycles of denaturation at 94° C. for 15 sec, annealing at 60° C. for 30 sec and extension at 72° C. for two minutes. Final extension is at 72° C. for 5 min, followed by a hold step at 10° C. PCR products are gel purified, spectrophotometrically quantified and an aliquot diluted to 1.7 nM concentration in 0.2 mg/ml yeast tRNA (Sigma) as a carrier nucleic acid. In a typical solution expression experiment 1 μl of 1.7 nM template in 0.2 mg/ml tRNA is added to 25 μl EcoPro T7 in vitro translation mix Novagen), supplemented with 0.75 μl of 100 mM oxidized glutathione (Sigma), and incubated at 25° C. for four hours. During the translation reaction the streptavidin-coated PCR tubes, cut from Strep Thermofast 96-well plates (Abgene), are first incubated at room temperature for three hours with 50 μl of at least 40 nM biotinylated target protein in PBS. The coating buffer is thereafter removed and any remaining free biotin-binding sites are blocked with a 15 min pulse of 50 μg/ml biotinylated BSA in PBS. The pre-coated wells are thereafter three times washed with PBS and then filled with 100 μl of binding buffer C+ (100 mM KCl, 20 mM Tris, 5 mM MgCl$_2$, 0.05% Tween 20, 0.05 mM EDTA, 1% BSA). Upon completion of the translation reaction the products are diluted in Buffer C+ and applied to the pre-coated and blocked PCR tubes, allowed to bind for 30 min at room temperature and washed 4 times with 150 μl of Buffer C+. The retained genetic elements are amplified with PCR using a nested set of primers AS13/AS19 and a 30-cycle PCR protocol 30X60C2-M. In 30X60C2M protocol 50 μl PCR reactions contain 200 μM each of dATP dTTP dGTP dCTP (Amersham), 300 nM forward and reverse primers AS13+AS19 and 1 U of SuperTaq DNA polymerase (HT Biotechnology) in 1× polymerase Buffer (HT Biotechnology). Initial denaturation at 94° C. for 2 min is followed by 30 cycles of denaturation at 94° C. for 15 sec, annealing at 60° C. for 30 sec and extension at 72° C. for two minutes. Final extension is at 72° C. for 5 min, followed by hold step at 10° C.

The DNA-binding activity of pIE2- and pIE3-derived HA-tagged scArc repressor constructs was tested using the following biotinylated proteins: α-HA mAb 3F10 (Roche), protein L (Pierce), β-galactosidase (Sigma) or BSA (Sigma). As it can be seen on FIG. 6A, scArc-HA secures the capture of its genetic element onto α-HA mAb 3F10-coated surface only when it is expressed from the pIE2aA-derived construct that has a single Arc operator present on the DNA. There is little, if any, of the encoding DNA retained on the surfaces coated with proteins that either do not interact with scArc-HA or when the genetic element lack the Arc operator (as is the case with pIE2A-derived genetic element). As shown on FIG. 6B, the same is also true for the pIE3-derived scAre-HA, that has the MCS-encoded region between the scArc and the C-terminal HA-tag and not at the N-terminus, as in the case of pIE2-encoded scArc-HA. Therefore, the presence of the Arc operator on the genetic element is required for the interaction between a scArc molecule and its genetic element and the in vitro translated scArc-HA can bind to it.

Similar assays can be used to assess the functional integrity of scArc fusion constructs with Vk domain antibodies. As an example, a β-galactosidase specific clone V$_\kappa$(E5) is used to assemble a series of N- and C-terminal fusion constructs to scArc in plasmids containing no, one, two, three or four Arc operators (as outlined on FIG. 2). Construct pIE2AV$_\kappa$(E5) encodes a fusion protein where the C-terminus of Vk(E5) is linked to the N-terminus of scArc via a short GS-linker with no Arc operator sites in the construct. pIE2AaV$_\kappa$(E5), pIE2AaV$_\kappa$(E5), pIE2Aa$^3$V$_\kappa$(E5) and pIE2AaV$_\kappa$(E5) expression constructs are identical to that of pIE2AaV$_\kappa$(E5) but have respectively one, two, three or four Arc operator sites present, as outlined on FIG. 2. The Arc operator sites repeat at after 45 bp interval, corresponding approximately to four helical turns of the B-form DNA. This ensures that the DNA-bound fusion proteins are all exposed in the same direction in order to facilitate the avidity effect from multi-protein complexes. Similar expression cassettes are also assembled for the fusion of Vk(E5) to the C-terminus of scArc in pIE3 series of vectors. Accordingly, pIE3AV$_\kappa$(E5), pIE3AaV$_\kappa$(E5), pIE3Aa$^2$V$_\kappa$(E5), pIE3AaV$_\kappa$(E5) and pIE3Aa$^4$V$_\kappa$(E5)

encode scArc-Vk(E5)-HA fusion protein from a template that has none, one, two, three or four Arc operator sites present on the construct. All genetic elements are recovered from the expression constructs by 25-cycle PCR protocol 25X60C2M using primers AS11 and AS17 as described above.

Tubes from Strep Thermofast 96-well plates are coated by applying 2 µl of 0.05 mg/ml biotinylated rat anti-HA mAb (clone 3F10, Roche), 0.2 µl of 0.5 mg/ml biotinylated protein L (Pierce), 1 µl of biotinylated 1 mg/ml β-galactosidase or 0.1 µl of 5 mg/ml biotinylated BSA (Sigma) respectively in 50 µl aliquots of PBS and incubating for 3 hours at room temperature. The monoclonal high-affinity α-HA mAb 3F10 recognises the C-terminal HA tag, β-galactosidase and protein L can be expected to interact with the $V_\kappa$(E5) light chain domain, while BSA serves as the negative control. At the end of the incubation the coating solution is removed and the first blocking solution consisting of 150 µl of 10 ng/ml biotinylated BSA (Sigma) in PBS is added to the wells and incubated for 15 minutes. At the end of the incubation the wells are washed three times with 150 µl of PBS and blocked additionally for 30 min at room temperature with buffer C+.

25 µl S30 in vitro translation reactions (EcoPro T7, Novagen) are assembled according to the manufacturer's instructions and supplemented with 1.5 µl of 1.7 mM PCR-amplified template in 0.1 mg/ml RNA and 0.75 µl of 100 mM oxidized glutathione. Translation reactions are incubated at 23° C. for 4 hours and diluted with 150 µl of buffer C+ (10 mM Tris, 100 mM KCl, 0.05% Tween 20, 5 mM $MgCl_2$, 0.1 mM EDTA, 1% w/v BSA) before being applied in 50 µl aliquots to the pre-coated tubes cut from Strep Thermofast 96-well plates (Advanced Biotech) and allowed to bind for 30 min at room temperature. At the end of the binding reaction the solution is removed and the tubes are washed with three times with 200 µl aliquots of buffer C+. Finally, the captured DNA is amplified by PCR in 50 µl volume using primers AS12 and AS18 and the same profile that was used for the preparation of the template.

Figure 7:
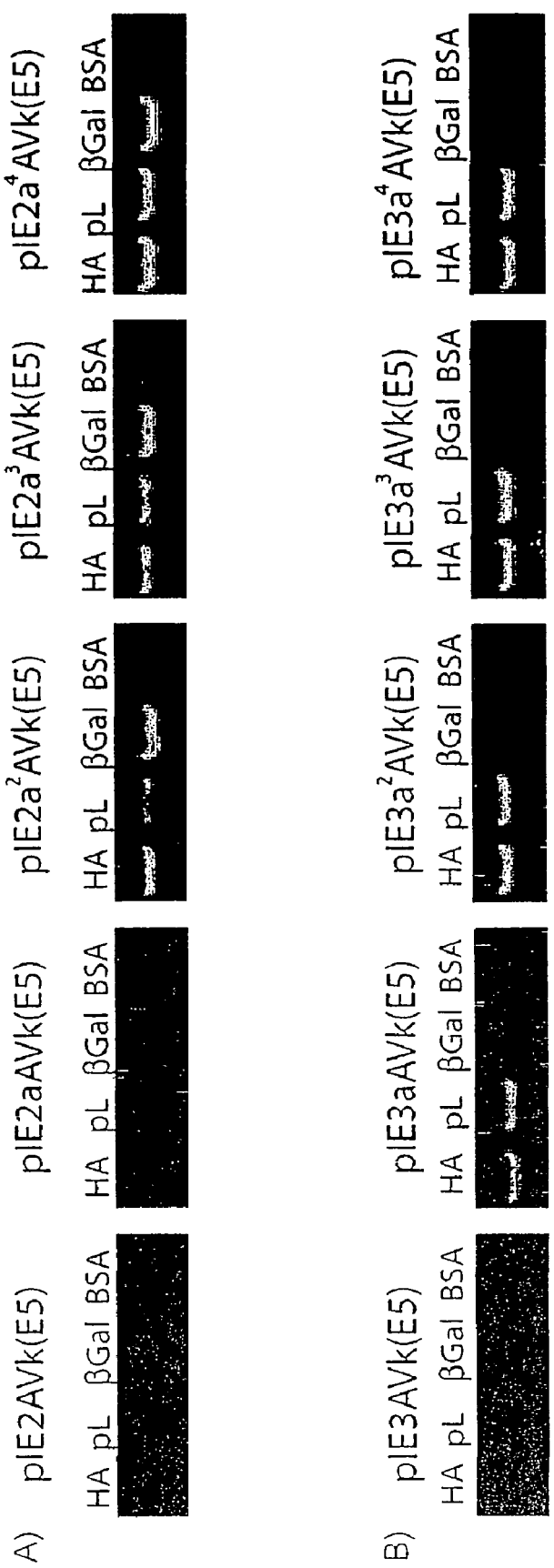
FIG. 7 The formation of protein-DNA complex between HA-tagged scArc-Vk(E5) protein, derived form series pIE2 vectors (A), or Vk(E5)-scArc protein, derived from pIE3 vectors (B), and their encoding DNA fragments depends on the presence, and the number, of the Arc operators on the genetic element. The complex formation is detected through the capture by biotinylated α-HA mAb, protein L (pL), β-galactosidase (βGal) or BSA, all immobilised onto streptavidin-coated PCR tubes.

The PCR amplification products are analysed by 1% agarose gel electrophoresis in TAE in the presence of ethidium bromide and imaged using GeneGeius Bio Imaging System (Syngene). The intensity of the band correlates with the amount of DNA retained on the surface of the tubes coated with different biotinated molecules that can interact with the in vitro expressed protein. As it can be seen on FIG. 7, there is little DNA recovered on either α-HA mAb, protein L or BSA if there are no Arc operator binding sites on the genetic element used for the expression of the $V_\kappa$(E5)-scArc-HA or scArc-$V_\kappa$(E5)-HA constructs. However, as the number of Arc operator sites increases, so does the amount of DNA recovered, as suggested by the intensity of the PCR product band on the gel, reaching plateau at 3-4 operator sites per gene. Given that each operator binds two scArc molecules, this is expected to allow up to octavalent interaction between the protein-DNA complex and the immobilised antigen. Therefore, in vitro expressed scArc-$V_\kappa$(E5)-HA fusion protein can form a complex with its encoding DNA, the complex is formed specifically, and it depends on the presence of the Arc operator(s) on the genetic element. Higher number of Arc operators results in the increased recovery of the protein-DNA complex, presumably through the avidity effect.

Significantly, only pIE2-series derived constructs with $V_\kappa$(E5) fused to the N-terminus of scArc in pIE2-series constructs, allow recovery on the β-galactosidase antigen-coated surface, suggesting strong steric hindrance in the opposite orientation in pIE3-series of constructs where the $V_\kappa$ domain antibody is fused to the C-terminus of scArc.

Example 3

The Formation of Stabile Genotype-Phenotype Linkage Between the $V_\kappa$-scArc Fusion Protein and its Genetic Element is Promoted by αHA mAb Successful in vitro selection of $V_\kappa$ domain antibody-scArc fusion proteins on the basis of the antigen-binding activity of the $V_\kappa$ domain depends among other factors also on the stability of the protein-DNA complex. The dissociation rate of the fusion protein—DNA interaction should be sufficiently low to maintain the genotype-phenotype linkage throughout the emulsion breakage and the subsequent affinity capture stage, for about at least 1 hour in total. In other words, once the emulsion is broken and the compartments are pooled, there should be little or no re-equilibration between the reversible protein-DNA complexes formed in the emulsion compartments between the expressed gene products and their encoding genetic elements.

This is not the case when $V_\kappa$ domain antibody is in fusion to the N-terminus of scArc and is expressed in the conditions described in Example 2. As it can be seen in FIG. 8A, when the $pIE2a^2AV_\kappa$(E5) and pIE2aA-derived genetic elements are used in separate in vitro translation reactions to express $V_\kappa$(E5)-scArc and scArc proteins respectively, and then mixed in equimolar ratio immediately before affinity capture stage, the $V_\kappa$-specific reagents protein L and β-galactosidase also lead to the capture of the pIE2aA-derived scArc-encoding elements, demonstrating that the $pIE2a^2AV_\kappa$(E5)-derived $V_\kappa$(E5)-scArc fusion protein was in complex with the scArc-encoding genetic elements derived form pIE2aA, proving that at least the scArc-DNA complex was relatively unstable, and probably the $V_\kappa$(E5)-scArc-DNA complex as well. Moreover, the genotype-phenotype linkage between the two species of DNA and their respective translation products, when recovered from the post-in vitro translation mix, is indistinguishable from that recovered from the reaction in which both species equimolar amounts of genetic elements are translated simultaneously in the same tube and the translation products are exposed to both species of genetic elements simultaneously. Therefore, successful target-specific recovery of genetic elements in conditions when only one type of genetic elements is used for the translation reaction is not a reliable indicator regarding the stability of the protein-DNA complex required for the in vitro selection purposes.

Given that the Arc operator is a pseudopalindromic sequence that can be expected to be capable of binding two scArc, or $V_\kappa$ fusion protein molecules, it can be shown that it is possible to stabilize the protein-DNA complex by cross-linking the operator-bound $V_\kappa$(E5)-scArc molecules via their C-terminal HA-tags using high-affinity, almost irreversible αHA rat mAb 3F10 (Roche). The distance between the C-termini of two Arc operator-bound scArc molecules, estimated from the X-ray structure, is about 3-4 nm, depending on the way the scArc DNA-binding domain is oriented on the pseudopalindromic half-site. Additionally, there is a $(G_3S)_2$ linker between the C-terminus of scArc and the nonapeptide HA-tag, adding extra flexibility to this part of the fusion protein and enabling the αHA 3F10 IgG mAb to engage both HA tags simultaneously in effectively irreversible manner, thus stabilising the protein-DNA complex trough the avidity effect. The stabilising effect of αHA mAb 3F10 on the $V_\kappa$(E5)-scArc-DNA complex is shown on FIG. 8B. The presence of 3.4 nM αHA mAb in the translation reaction, and participation in the protein-DNA complex does not interfere with the protein L- or β-galactosidase-binding activity of the $V_\kappa$ moiety of the $V_\kappa$(E5)-scArc fusion protein. In contrast, the effect of αHA mAb cross-linking on the stringency of the genotype-phenotype linkage is profound, as of the separately translated $V_\kappa$(E5)-scArc and scArc molecules only pIE2a$^2$AV$_\kappa$(E5)-derived V$_\kappa$(E5)-scArc-encoding genetic elements are recovered during V$_\kappa$-binding protein L and β-galactosidase-mediated capture.

Figure 8:
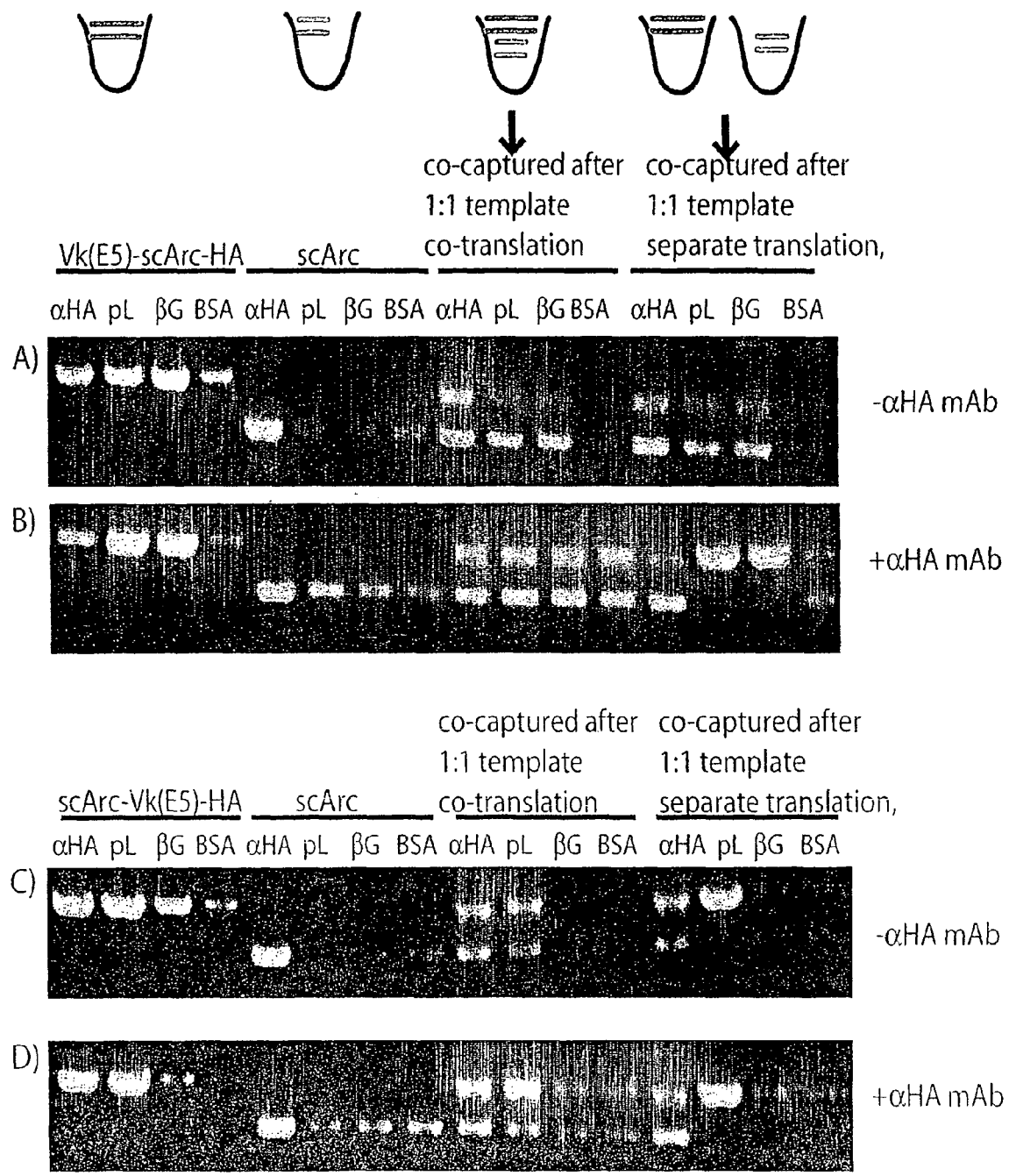
FIG. 8 The effect of αHA mAb 3F10 on the strength of the genotype-phenotype linkage between scArc-$V_\kappa$ fusion proteins and the respective genetic elements, as assayed through the effectiveness of the co-capture of the coding genetic elements on αHA mAb 3F10, protein L, β-galactosidase or BSA. The constructs are expressed and captured either separately, expressed and capered simultaneously or expressed separately but captured: simultaneously. A) $V_\kappa$(E5)-scArc and scArc in the absence of mAb 3F-10. B) $V_\kappa$(E5)-scArc and scArc in the presence of mAb 3F10. C) scArc-$V_\kappa$(E5) and scArc in the absence of mAb 3F10. B) scArc-V$_\kappa$(E5) and scArc in the presence of mAb 3F10.

The effect of the cross-linking αHA mAb 3F10 on the stability of genotype-phenotype linkage is less pronounced in the case of pIE3a$^2$AV$_\kappa$(E5)-derived fusion construct scArc-V$_\kappa$(E5)-where the V$_\kappa$ domain antibody is in fused to the C-terminus of scArc. Even in the absence of mAb, the genotype-phenotype linkage between scArc-V$_\kappa$(E5) and its pIE3a$^2$AV$_\kappa$(E5)-derived genetic element is strong enough to allow isolation on V$_\kappa$-binding protein L (the β-galactosidase-binding activity of V$_\kappa$(E5) is hindered when expressed in fusion to the C-terminus of scArc) (FIG. 8C). Correspondingly, there is little, if any improvement on that in the presence of mAb. If anything, there is a possibility that the antigen-binding activity of the V$_\kappa$(E5) domain is further compromised by cross-linking through the C-terminal HA-tag (FIG. 8D).

Therefore, the expression of V$_\kappa$ domains in fusion to the N-terminus of C-terminally HA-tagged scArc in the presence of αHA mAb 3F10 is the optimal solution regarding the antigen-binding activity of the V$_\kappa$ domain and the DNA-binding activity of the scArc domain.

Example 4

The Formation of Stable Genotpe-Phenotype Linkage Between the V$_\kappa$-scArc Fusion Protein and its Genetic Element is Promoted by αHA mAb 3F10 Also in Emulsion Successful emulsion-based in vitro selection of V$_\kappa$ domain antibody-scArc fusion proteins on the basis of the V$_\kappa$ antigen-binding activity requires that the stabilising effect of αHA mAb F10 on the V$_\kappa$-scArc-DNA complex, as demonstrated in Example 3 for the bulk solution expression, would also be retained in the emulsified in vitro translation reactions.

In order to demonstrate that the αHA mAb 3F10 stabilizes the V$_\kappa$-scArc-DNA complex also in an emulsified in vitro translation reaction, three in vitro translation reactions were assembled in the presence of 3.4 nM αHA mAb 3F10. The first two reactions 50 μl of EcoPro T7 in vitro translation mix contained 10$^9$ pIE2a$^2$AV$_\kappa$(E5)- and pIE2a$^2$A-derived genetic elements, encoding V$_\kappa$(E5)-scArc and scArc respectively. The third reaction contained 5×10$^8$ copies of both V$_\kappa$(E5)-scArc and scArc-encoding genetic elements. The assembled in vitro translation reactions were emulsified in 0.6 ml aliquots of light white mineral oil (Sigma) containing 4.5% Span-80 (Fluka) and 0.5% Triton X-100 (Sigma) by stirring the mixture in 4 ml Corning Cryogenic Vials (Cat. #430491) at 1500 rpm for 5 min at room temperature using a Variomag 15 multipoint magnetic stirrer and 2.5×8 mm magnetic stirring bars. After four hours of incubation at 25° C., i.e. immediately before the breaking step, 0.3 ml aliquots of the first two emulsions, containing respectively pIE2a$^2$AV$_\kappa$(E5)- and pIE2a$^2$A-derived genetic elements, were mixed to yield the fourth emulsion. At this point 100 μl of buffer C+ and 0.5 ml of hexane (Sigma) were added to each emulsion, mixed carefully, and then centrifuged at 4° C. in a refrigerated microcentrifuge for 1 min. The organic phase was removed and the remaining aqueous phase was further extracted six times with hexane, each time spun down by 30-sec centrifugation at 4° C., in order to remove the detergents until clear aqueous phase was obtained. The volume of the recovered aqueous phase was adjusted to 200 ml with buffer C+ and the sample was split into four 50 ml aliquots, each applied to a streptavidin-PCR tube coated with biotinylated forms of anti-HA mAb 3F3 (Roche Cat: 2 158 167), protein L (Pierce), β-galactosidase (Sigma) or BSA (Sigma). From then on, the samples were processed as described in Example 3.

Figure 9:
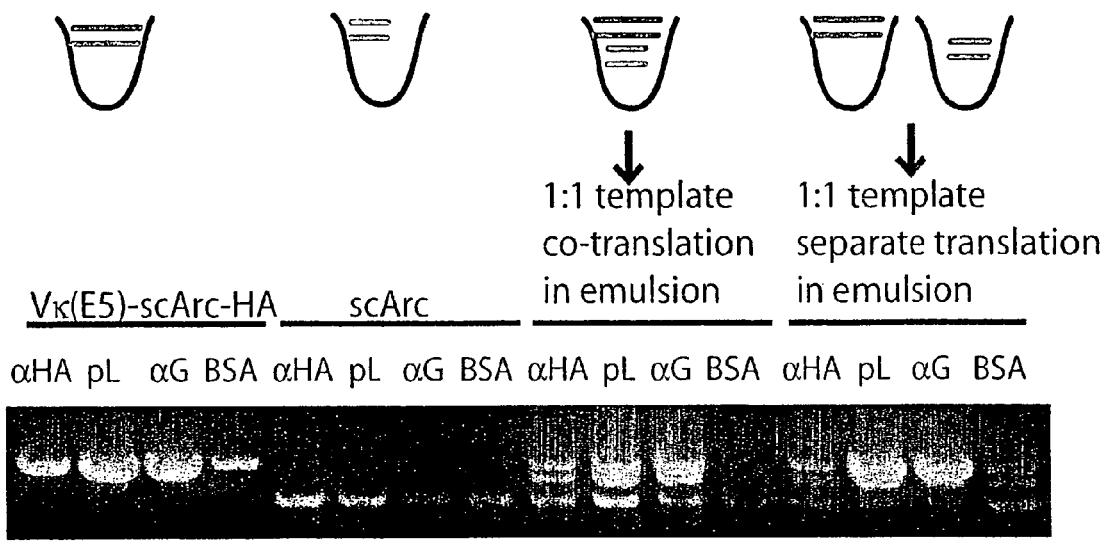
FIG. 9 αHA mAb 3F10 can stabilize the genotype-phenotype linkage between V$_\kappa$-scArc fusion proteins and the respective genetic elements also in emulsion expression, as assayed through the effectiveness of the co-capture of the genetic elements on αHA mAb 3F10, protein L, β-galactosidase or BSA-coated surfaces. The constructs are expressed in emulsion and captured either separately, expressed and captured simultaneously or expressed separately but captured simultaneously (aliquots of emulsion are mixed and broken simultaneously).
Figure 10:
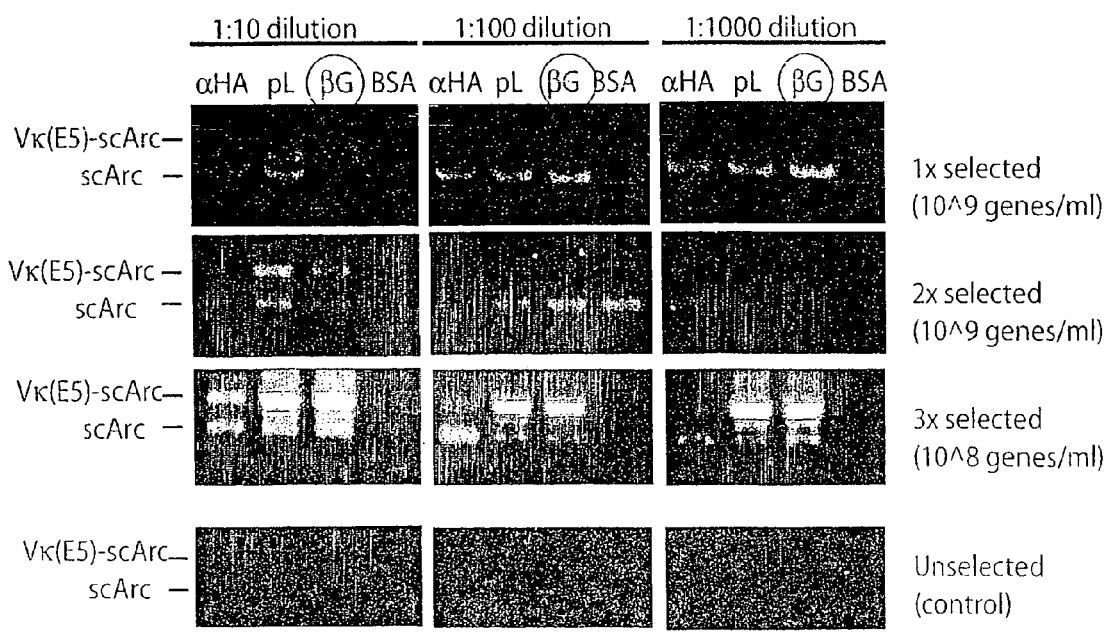
FIG. 10 Sequential enrichment of the pIE2a$^2$AV$_\kappa$(E5)-derived target construct expressing V$_\kappa$(E5)-scArc over the pIE2a$^2$A-derived competitor construct expressing scArc. The genetic elements captured by β-galactosidase-coated tubes gene were gel purified on 1.2% E-Gels and used as the starting material for the next round of selection.

As it can be seen from FIG. 9, the protein-DNA complexes, derived from the emulsified in vitro translation reactions, have essentially the same genotype-phenotype linkage characteristics as those derived from the non-emulsified sample (FIG. 8B). In vitro emulsion expressed pIE2a$^2$AV$_\kappa$(E5)-derived co-precipitates effectively it's genetic element through protein L and β-galactosidase-mediated capture, while the pIE2aA-derived scArc does not. Most importantly, when V$_\kappa$(E5)-scArc and scArc are translated in separate emulsions, that are mixed immediately before the breaking step (the fourth sample), the translation products are firmly associated with their encoding genetic elements, as demonstrated by the efficient capture of the pIE2a$^2$AV$_\kappa$(E5)-derived genetic elements on V$_\kappa$(E5)-specific reagents protein L and β-galactosidase, in spite of the presence of equimolar amount of the pIE2a$^2$A-derived competitor. Regarding the third reaction where equimolar amounts of the target and competitor genetic elements were added to the translation reaction before emulsification, there is enrichment of the pIE2a$^2$AV$_\kappa$(E5)-derived genetic elements on protein L and β-galactosidase-coated surfaces when compared with the relative amounts of the genetic elements recovered in a non-emulsified control reaction as shown on FIG. 8B. More limited co-purification of the pIE2aA-derived genetic elements on protein L and β-galactosidase in the sample where the in vitro translation mix containing equimolar amounts of both species of genetic elements, as opposed to the reaction when they were translated separately, is most likely the result of imperfect segregation of the large number of genetic elements used in the reaction (10$^9$) into individual compartments of in vitro translation mix emulsified in mineral oil.

pIE2a$^2$AV$_\kappa$(E5)-derived genetic elements can be sequentially enriched from the excess of pIE2a$^2$A-derived genetic elements by affinity purification of the pIE2a$^2$AV$_\kappa$(E5)-encoded V$_\kappa$(E5)-scArc complexed DNA on the solid surface immobilised β-galactosidase—the specific antigen of V$_\kappa$(E5). Sequential enrichment of the pIE2a$^2$AV$_\kappa$(E5)-derived target genetic construct encoding β-galactosidase-binding V$_\square$(E5)-scArc over the competitor construct scArc, derived from pIE2aA, is demonstrated on FIG. 10. In this model selection the volume of the aqueous phase recovered from the emulsion was adjusted to 200 μl and allowed to bind in 50 μl aliquots in four different tubes to immobilised αHA mAb 3F10, protein L, β-galactosidase and BSA. The surface-bound genetic elements were amplified in the first round of selection using primers AS14 and AS20, in the second round using primers AS15 and AS21, while in the final round primers AS16 and AS22 were used. In the amplification protocol 35X60C2M50 μl PCR reactions contain 200 μM each of dATP, dTTP, dGTP and dCTP (Amersham), 300 nM forward and reverse primers and 1 U of SuperTaq DNA polymerase (HT Biotechnology) in 1× polymerase Buffer (HT Biotechnology). Initial denaturation at 94° C. for 2 min is followed by 35 cycles of denaturation at 94° C. for 15 sec, annealing at 60° C. for 30 sec and extension at 72° C. for two minutes. Final extension is at 72° C. for 5 min, followed by a hold step at 10° C. 10 μl aliquots of the amplification reaction products were run on 1% agarose gels and are shown on FIG. 10. The rest of the PCR product from the β-galactosidase-coated well was purified on 1.2% E-Gels (Invitrogen) and cut out on the UV transilluminator using a razor blade whilst making sure that the excised gel fragment was sufficiently large to contain both the target and the competitor genetic elements.

The enrichment factor of the $pIE2a^2AV_\kappa(E5)$-derived target genetic element over the $pIE2a^2A$-derived competitor genetic element depends on the initial target-competitor ratio and the total concentration of genetic elements in the aqueous phase. Approximately 100-fold enrichment is observed when the target is diluted 1000-fold into the competitor and $10^9$ genetic elements are added to 50 µl aqueous phase. Further enrichment of the target genetic elements from approximately 1:10 target:competitor ratio can be achieved by improving the segregation of genetic elements by reducing their concentration 10-fold while retaining the volume of the emulsion.

Example 5

Quantitative Assay of Protein-DNA Complex Formation in Emulsified In Vitro Translation Reactions Emulsion-based in vitro selection of antibody fragments requires efficient genotype-phenotype complex formation between the genetic elements and their encoded protein products within the droplets of bacterial S30 extract emulsified in mineral oil. The efficiency of this complex formation can be assessed by measuring the concentration of protein-DNA complexes formed between the genetic elements and their encoded protein products. As an example, quantitative PCR can be used to measure the number of $pIE3a^4AV_\kappa(E5)$-derived genetic elements captured onto the surface of αHA mAb 3F10-coated PCR tubes via the C-terminal HA tag of the DNA-bound scArc-$V_\kappa$(E5) molecules in the conditions where the expected binding capacity of the surface significantly exceeds the number of both the DNA molecules submitted to the reaction as well as the number of in vitro translated protein molecules. The tubes from the Strep Thermo-Fast 96-well streptavidin-coated PCR plates, used here for the capturing and amplification purposes, are reported by the manufacturer to have free biotin-binding capacity of about 50 pmol per tube in 50 µl volume, corresponding to approximately 1 pmol of macromolecule-binding capacity. 2 µl aliquots of 500 nM biotinylated αHA mAb 3F10 (Roche) per tube in 50 µl volume were used to coat the biotin-binding sites of streptavidin with αHA mAb. This applied amount of biotinylated mAb molecules exceeds at least 40-fold the number of protein molecules expressed from approximately 0.25 fmol of DNA template, assuming the expression yield of about 100 molecules per template.

Specifically, 50 µl in vitro translation reaction was set up as described in Example 3, using 0.5 µl of 1.7 nM template derived from $pIE3a^4AV_\kappa(E5)$ using primers AS11 and AS17, and added in one aliquot to 0.5 ml light mineral oil (Sigma) supplemented with 4.5% Span-80 (Fluka) and 0.5% Triton X-100 (Sigma) whilst stirring at 1600 rpm for 5 min. Emulsification was carried out in 5 ml Becton-Dickinson FACS tubes using a 8×3 mm magnetic stirring bar and the translation reaction was allowed to proceed for 4 hours at 23° C. The aqueous phase was recovered by adding 150 µl of buffer C+ and 0.5 ml of n-hexane to the emulsion and centrifuging at 24000 g for 1 min at 20° C. in 1.5 ml Eppendorf tubes. The excess detergents were removed through seven rounds of extraction with 1 ml aliquots of n-hexane. At the end of each extraction step the aqueous phase was centrifuged down during a 24000 g spin lasting for 20 sec at 20° C. After final extraction the volume of the aqueous phase was adjusted to 200 µl with buffer C+ and added in four 50 µl aliquots to four Strep Thermofast PCR tubes coated with α-HA mAb 3F10. Adsorption and washing steps were carried out as described in Example 3.

Quantitative PCR on an ABI PRISM® 7700 Sequence Detection System (Applied Biosystems) using QuantiTect SYBR Green PCR Kit (Qiagen) with primers AS79 and AS80 was set up using the following amplification protocol: initial denaturation at 95° C. for 15 minutes was followed by 50 cycles of 15 sec at 95° C., 30 sec at 60° C. and 1 min at 72° C. Calibration curve standards were diluted from the same stock solution used for the in vitro translation reaction and run in quadruplicate at $6.25\times10^7$, $5.0\times10^7$, $3.75\times10^7$, $2.5\times10^7$, $1.25\times10^7$, $6.25\times10^6$ and $2.5\times10^6$ copies per well. The negative control had no DNA added at all. As it can be seen from FIG. 11A, the standard samples, as well as the unknown samples, require between 17 to 22 cycles to cross the detection threshold, whereas for the negative control sample without any DNA added, this figure is about 37 cycles. The threshold values for the standard samples used in the amplification reaction depended linearly on the copy number of the DNA molecules in the PCR reaction (FIG. 11B) in the concentration range used. The average threshold crossing value for the unknown emulsion-derived sample was 19.3+/−0.8 cycles corresponding to $2.9\times10^7$ copies per well and $1.2\times10^8$ copies in total from the four parallel binding reactions. Therefore, at least 23% of the total input genetic element DNA ($5\times10^8$ molecules) was recovered in complex with Arc-$V_\kappa$(E5) on αHA mAb-coated surface.

Example 6

Model Selection of a $V_\kappa$-Single Domain Antibody Fused to the C-Terminus of scArc. The Fidelity of Genotype-Phenotype Linkage in Emulsified In Vitro Translation Reactions The formation of genotype-phenotype linkage between the emulsion-expressed genetic elements and their encoded protein products, as demonstrated in Example 2-4, and the extent of protein-DNA complex formation between the genetic elements and their encoded protein products, as demonstrated in Example 5, demonstrates that it is possible to select genetic elements according to the binding activity of the $V_\kappa$ domain antibody expressed in fusion to the N-terminus of scArc DNA-binding protein.

Additionally, Example 2 also demonstrates that the fusion proteins where $V_\kappa$ domain antibodies are fused to the C-terminus of scArc are also capable of forming stable protein-DNA complexes with their encoding genetic elements. Accordingly, two model selection reactions were set up with the aim of demonstrating the possibility of selecting $V_\kappa$ domain antibodies fused to the C-terminus of scArc and exploring how the enrichment factor of the selection process depends on the number of genetic elements entered included in the selection. In both model selection reactions the target molecule was chosen to be $pIE3aAV_\kappa(E5)$-derived genetic element encoding scArc-$V_\kappa$(E5), the fusion of $V_\kappa$(E5) to the C-terminus of scArc, and the competitor molecule pIE3aA-derived scArc. Both these molecules are recognised by the αHA mAb 3F10, whilst only scArc-$V_\kappa$(E5)-HA can interact with protein L and neither of them with BSA. Both proteins are expressed from genetic elements carrying one Arc operator site. In the first model selection the target construct genetic element is diluted 1 000 000-fold into the competitor construct genetic element and the selection is carried from the aliquot of 5×10⁸ molecules. In the second model selection the target construct genetic element is diluted 10 000-fold into the competitor construct genetic element and the selection is carried from the aliquot of 5×10⁹ molecules. Given that 0.5 ml of emulsion prepared from 50 µl of in vitro translation mix and 0.5 ml of oil phase contains about 10¹⁰ droplets, it can be expected that 5×10⁸ molecules will be distributed, on average, at 1 gene per droplet, whilst at 5×10⁹ genes many of the compartments will contain two or more genes. Increased number of genetic elements will compromise the fidelity of the genotype-phenotype linkage whilst, on the other hand, allowing selections from larger libraries.

The target and the competitor genetic elements were PCR amplified from the vectors pIE3aAVκ(E5) and pIE3aA respective using primers AS11 and AS17 as described in Example 2. The amplification reaction products were gel purified on 1.2% E-gel units (Invitrogen), quantified spectrophotometrically on a Biophotometer (Eppendorf) and diluted to 1.7 nM concentration in 0.1 mg/ml yeast tRNA (Sigma). There is 344 bp difference between the length of the genetic elements. The control expression reactions in bulk solution were carried out as described in Example 2, while the emulsion expression reactions were carried out as described in Example 5. 5 µl aliquots of the unpurified PCR amplification products were also run separately on a conventional 1×TAE 1% agarose gel to monitor the progress of the selection process. In each subsequent round of selection the primers used for 1 amplification reaction were applied in nested pairs. In round 1 the primers were AS12 and AS18, in round 2 AS13 and AS19, in round 3 AS14 and AS20, in round 4 AS15 and AS21, in round 5 AS16 and AS22 and in round 6 AS29 and AS153. Although the length of the genetic elements decreases from round to round because of the nesting process, the difference between the two competing species remains constant at 344 bp (i.e. length of the unit encoding Vκ(E5)), allowing discrimination between the genetic elements by agarose gel electrophoresis.

Figure 12:
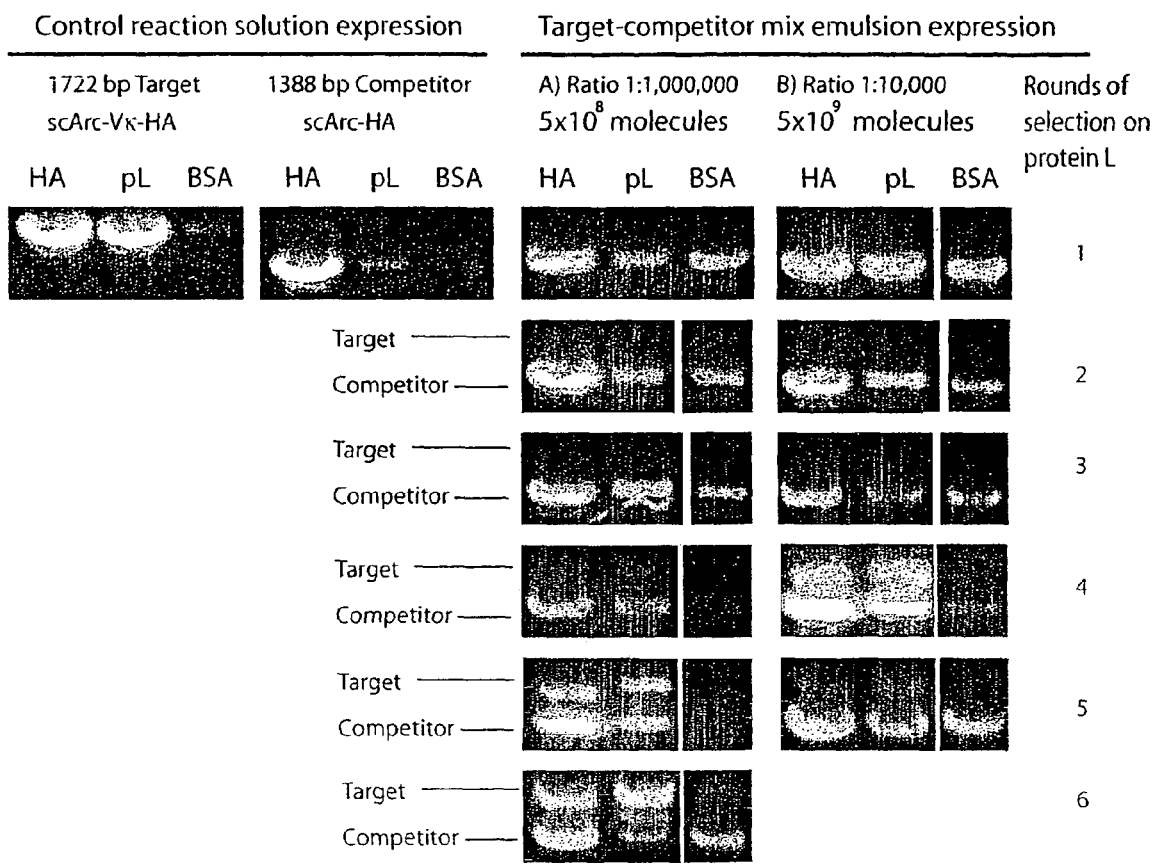
FIG. 12 Model selections of scArc-Vκ(E5)-HA from the background of scArc-HA at two different DNA concentrations. The model library of 1:1 000 000 dilution was selected at 5×10$^8$ molecules per reaction, whereas the 1:10 000 diluted model library was selected at 5×10$^9$ molecules per reaction in 50 µl volume translation mix emulsified in 0.5 ml oil phase.

As it can be seen on FIG. 12, the target construct remains undetectable by electrophoresis through the first 2-3 rounds of selection. It takes five rounds of selection from the 1:1 000 000 model library at 5×10⁸ molecules per reaction to reach approximate equimolarity of the genetic elements, suggesting the average factor of enrichment in the region of 15. There is further enrichment in round 6 as well, but it is obviously less than 15, although the target construct does become dominating. In contrast, for the model selection from 1:10 000 diluted model library at 5×10⁹ molecules per reaction reaches plateau by the fourth round at approximate target to competitor ratio 1:10, suggesting the enrichment factor to have the value around 6. Therefore, emulsion-based expression of Vκ0 light chains in fusion to the C-terminus of scArc DNA-binding protein can be used for the selection of Vκ light chains according to their binding specificities. In a manner that should be applicable also to the N-terminal fusions, it has also been shown that the enrichment factor of the selection process depends on the total number of genetic elements added to the translation mix. Higher number of genetic elements enables to select from larger libraries but at the cost of decreased enrichment factor. Obviously, this gives rise to the opportunity, according to the need, to optimize the library size vs to the enrichment factor. It can be envisaged that during the first few rounds of selection larger sized libraries may be entered to the emulsion in order to maximize the diversity, at the cost of enhanced enrichment. During the later stages of selection when the diversity is already reduced, it will be possible to accelerate the selection process by decreasing the number of genetic elements entering the emulsion.

Example 7

Selection of Calf Intestine Anti-Alkaline Phosphatase (CIAP) Domain Antibodies from a Naïve Synthetic Vκ Library In Example 4 we demonstrated the model selection of a weak ($K_d$>1 µM) anti-β-galactosidase Vκ(E5) and noted that the same setup could be used for the selection of novel dAbs against other antigens from naïve Vκ dAb libraries expressed in N-terminal fusion to scArc from constructs with two Arc operator sites per gene.

Preparation of the Library Insert

The naïve combinatorial human Vκ dAb library was obtained by PCR amplification from the phage display library G4 using primers AS251 and AS252. In total 8×10⁹ pfu of phage particles were amplified in six parallel 50 µl amplification reactions using protocol 15D35X60C2M. In protocol 15D35X60C2M each 50 µl PCR reaction contains 200 µM each of dATP, dTTP, dGTP and dCTP (Amersham), 300 mM forward and reverse primers and 1 U of SuperTaq DNA polymerase (HT Biotechnology) in 1× polymerase Buffer (HT Biotechnology). Initial denaturation at 94° C. for 15 min is followed by 35 cycles of denaturation at 94° C. for 15 sec, annealing at 60° C. for 30 sec and extension at 72° C. for two minutes. Final extension is at 72° C. for 5 min, followed by a hold step at 10° C. The amplification reaction products were gel purified by gel electrophoresis on disposable 1.2%-E-Gel agarose gels (Invitrogen), cut out from the gel under UV illumination and extracted from the gel slices using QiaPCR (Qiagen) disposable purification columns. The DNA fragments were eluted in water and cut with Nco I and Not I enzymes (both NEB). The digested Vκ library fragment was purified by electrophoresis on a disposable 2% E-Gel agarose gel (Invitrogen), cut out from the gel under UV illumination and, as before, extracted from the gel slice using QiaPCR (Qiagen) disposable purification columns. DNA was eluted from the column in water and its concentration was measured spectrophotometrically (Ultrospec 3300 Pro, Pharmacia).

Preparation of the Library Vector

The pIE2a²A vector was cut with Nco I and Not I enzymes (both NEB). The digested vector fragment was purified by electrophoresis on a disposable 2% a E-Gel agarose gel (Invitrogen), cut out from the gel under UV illumination and extracted from the gel slice using QiaPCR (Qiagen) disposable purification columns. DNA was eluted from the column in water and its concentration was measured spectrophotometrically (Ultrospec 3300 Pro, Pharmacia).

Ligation of the Library

10 µl of 17 nM Nco I-Not I cut vector (10¹² molecules) and 10 µl of 270 nM Nco I-Not I cut Vκ(G4) library fragments (1.6×10¹³ molecules) were ligated overnight at 16 C in 50 µl volume using 1000 U of T4 DNA ligase (NEB) in the recommended buffer.

Amplification of the Library and Estimation of its Diversity

Figure 13:
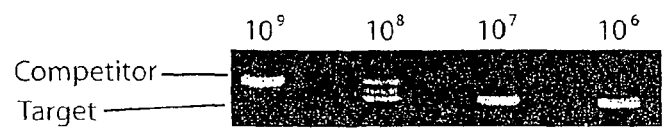
FIG. 13 Semi-quantitative competition PCR of the V$_\kappa$(G4) scArc library in pIE2a$^2$A vector. All PCR reactions contained a 0.5 µl aliquot of the ligated library (target) and were supplemented with 10$^9$, 10$^8$, 10$^7$ or 10$^6$ copies of the competitor fragment, both amplifiable with primers AS12 and AS18.
Figure 14:
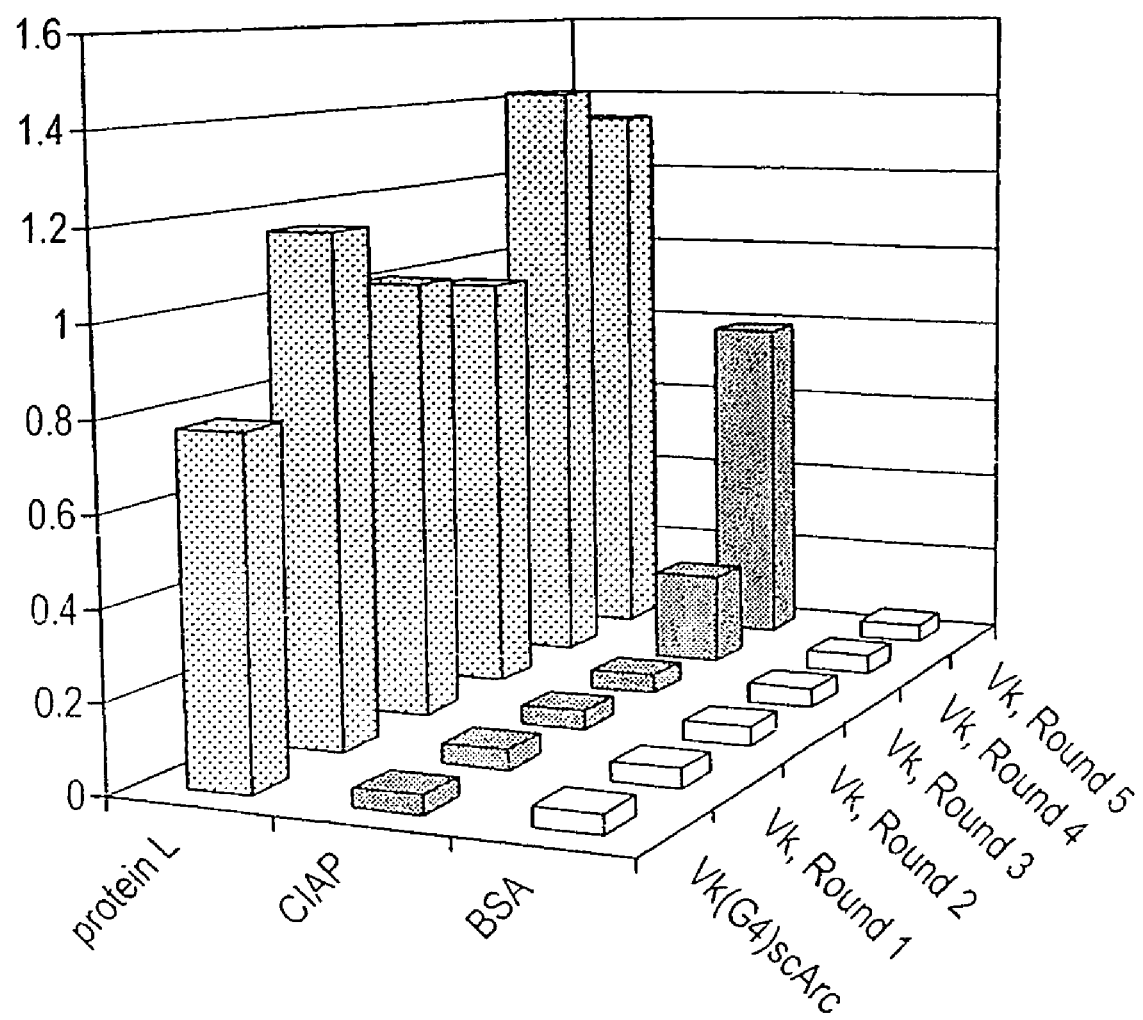
FIG. 14 One-Step ELISA screening of protein L, CIAP and BSA-binding activities of the polyclonal V$_\kappa$ population selected from the V$_\kappa$(G4) library by sequential enrichment on CIAP. V$_\kappa$(G4)scArc is the polyclonal naïve starting library in fusion to the N-terminus of scArc. The rest of the samples encode HA-tagged V$_\kappa$ polyclonal populations enriched for the CIAP-binding clones.

The diversity reached in the ligation reaction, i.e. the number of vector molecules that had acquired the Vκ(G4) dAb insert, was estimated by semi-quantitative competitive PCR (Siegling A. et al., J Immunol Methods, 1994, 177, 23-8). Specifically, 0.5 µl aliquots of the ligation reaction were co-amplified in a series of PCR reactions in the presence of 10⁹, 10⁸, 10⁷ and 10⁶ copies of competitor DNA. Both the library-derived target and the competitor fragment, derived from a similar pIE2-based construct, were co-amplified using SuperTaq DNA polymerase, PCR profile 25X60C2M and primers AS12+AS18. The library-derived fragment is 1731 bp long whereas the competitor fragment is 2124 bp long. Both fragments could be resolved by 1% agarose gel electrophoresis and the approximate number of successfully vector-ligated $V_\kappa$ dAb molecules in 0.5 µl of ligation reaction product was found to be approximately equal to $10^8$ (FIG. 13), indicating that there were $10^{10}$ vector molecules in the entire ligation reaction volume that had incorporated a $V_\kappa$ fragment. The remaining 48 µl volume of the ligation reaction was added directly to 400 µl of PCR mix and PCR amplified using SuperTaq DNA polymerase, primers AS1 and AS17 and thermal cycling profile 25X60C2M. The resulting 1778 bp PCR fragment-based $V_\kappa$(G4) library was loaded onto 1.2% E-Gel (Invitrogen), purified from the gel using QiaQuick columns (Qiagen), eluted in water and its concentration measured spectrophotometrically (Ultrospec 3300 Pro, Pharmacia). An aliquot of the library was diluted to the final concentration of 1.7 nM in water containing 0.25 mg/ml yeast tRNA.

Selection from the Library:

In the first round of selections 2 µl of 1.7 nM $V_\kappa$(G4) library ($2\times10^9$ molecules) were added to 125 µl of in vitro translation mix and this was emulsified in two 62.5 µl aliquots, each in 0.7 ml hydrophobic phase, as described above for the model selection. Emulsified reactions were incubated for four hours at 25° C. and the aqueous phase was recovered by six hexane extractions, each followed by a 1 minute 16000 g centrifugation step at 20° C.

As an example, biotinylated calf intestine alkaline phosphatase (Sigma) was used as a model antigen. Affinity capture of specific antibodies was carried out using biotinylated CIAP on four Streptavidin-coated PCR tubes cut from a Strep ThermoFast 96-well plate (ABGene). The tubes were coated with 50 µl of 10 µg/ml CIAP in PBS for two hours at room temperature. Unbound CIAP was removed and any remaining binding sites were blocked with 50 µg/ml biotinylated BSA in PBS for another 30 min at room temperature. Unbound CIAP was removed and the wells were washed three times with 150 µl PBS. The tubes were then filled with 150 µl buffer C+ for another 30 minutes. Buffer C+ was removed immediately before the volume of the aqueous phase recovered from the emulsion was adjusted to 200 µl and then aliquoted into freshly CIAP-coated PCR tube at 50 µl per well. The tubes were incubated for 30 min at room temperature and then washed 4 times with 150 µl of buffer C+. After final wash the buffer was removed and replaced with PCR premix containing primers AS12 and AS18. The bound molecules of DNA were thereafter amplified using the PCR profile 35X60C2M. The PCR product was gel purified by electrophoresis on a disposable 1.2% E-Gel agarose gel (Invitrogen), cut out from the gel under UV illumination and extracted from the gel slice using QiaQuick (Qiagen) disposable purification columns. DNA was eluted from the column in water and its concentration was measured spectrophotometrically (Ultrospec 3300 Pro, Pharmacia). An aliquot of the PCR-amplified population was diluted to the final concentration of 1.7 nM in water containing 0.25 mg/ml yeast tRNA.

The next four cycles of selection were carried out in the same fashion, each time using a new pair of nested primers, AS14+AS20, AS15+AS21, AS16+AS22 and AS29+AS153 respectively.

Characterisation of the Selection Process and the Selected Clones.

Slightly modified sandwich ELISA on biotinylated antigens immobilised onto streptavidin-coated microtitre plate wells (Streptawell 96, ABGene) was used to monitor the progress of the selection process through rounds of selection as well as for the characterisation of individual clones. The wells of the microtitre plate were coated for two hours at room temperature with 50 µl of biotinylated protein L (Pierce), biotinylated CIAP (Sigma) or biotinylated BSA (Sigma), at 2 µg/ml antigen per well in PBS. At the end of the coating step the antigen solution was removed and replaced with 200 µl of ELISA blocking solution (Roche) for another 30 min at room temperature. At the end of the blocking step the solution was removed and the wells were rinsed four times with 200 µl PBS/0.1% Tween 20 before the sample was applied in PBS/0.1% BSA/0.1% Tween 20.

The $V_\kappa$(G4) library polyclonal populations were in vitro translated by using the PCR fragments encoding the HA-tagged $V_\kappa$ domains as the template. The PCR fragments used for the translation were amplified from the selected $V_\kappa$-scArc encoding populations by using primers AS96 and AS263. The AS96 upstream primer retains the T7 promoter whilst the AS273 primer replaces the scArc domain at the 3' end of the $V_\kappa$ domain with as simple HA tag followed by a stop codon. Typically 1 µl of 1.7 nM library-encoding polyclonal population from all rounds of selection were amplified in 50 ml volume using SuperTaq DNA polymerase and the profile 35X60C1M. The PCR fragments were purified on QiaPCR columns, eluted in 30 µl of water at approximately 130 nM concentration and used for in vitro translation without any further manipulations. Typical 15 µl in vitro translation reaction was assembled according to manufacturer's instructions and contained either 1 µl of either QiaQuick-purified polyclonal 130 nM CIAP-selected $V_\kappa$-encoding template or gel-purified polyclonal 116 nM scArc-fused $V_\kappa$(G4) library-encoding template. In vitro translation was carried out in the conditions used during the selection process, except for the addition of the antis 3F10 mAb and emulsification.

Figure 15:
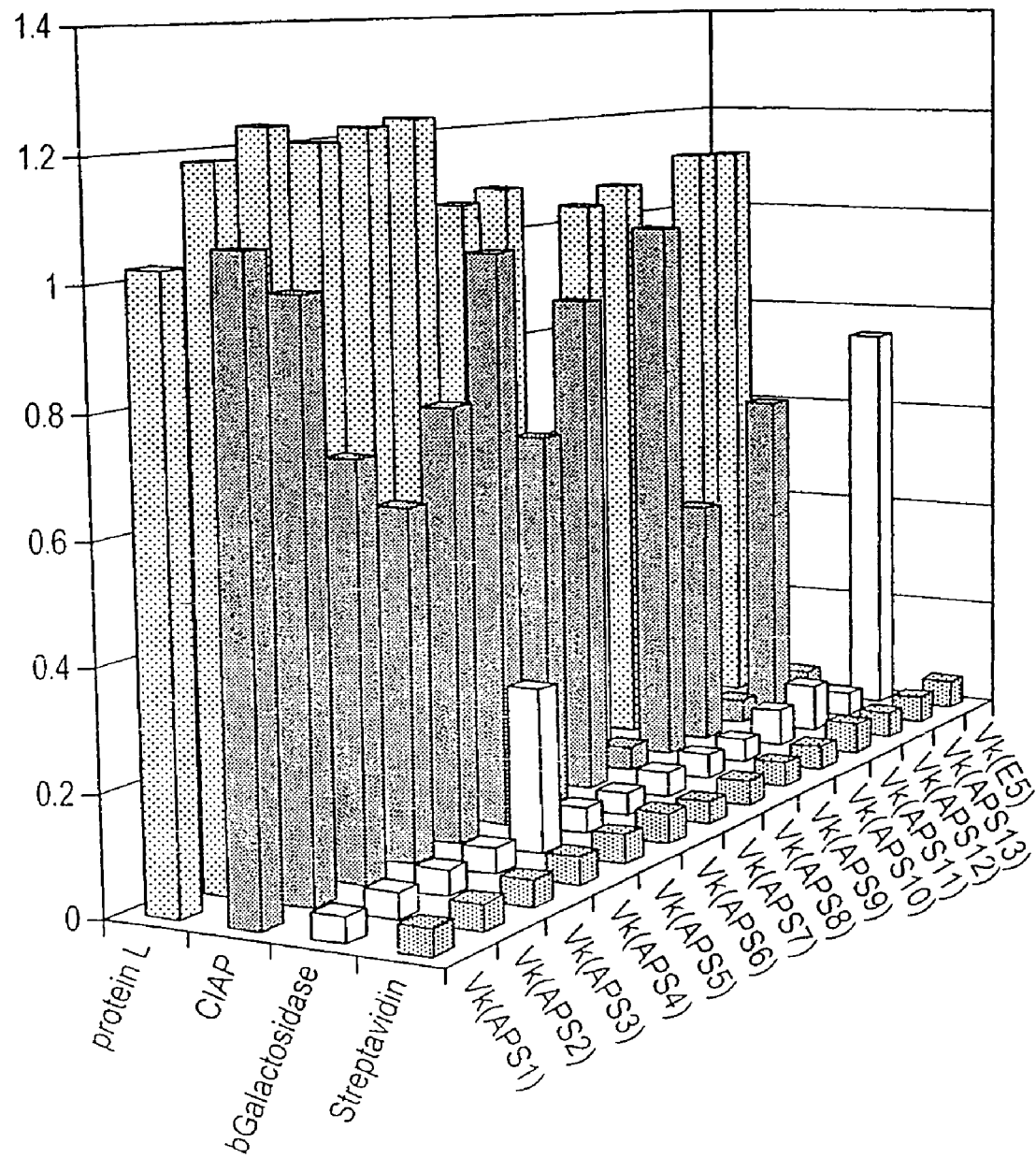
FIG. 15 ELISA screening of individual clones isolated from the CIAP-selection Round 5. 13 CIAP-selected and one positive control clone, β-galactosidase-specific Vk(E5), were analysed according to their protein L, CIAP, β-galactosidase and BSA-binding activities.

At the end of the translation reaction the samples were assayed using a "Single-Step" sandwich ELISA protocol. 15 µl of in vitro translation reaction products were diluted to 150 µl with PBS/0.1% BSA/0.1% Tween 20 containing 50 ng/ml 3F10 anti-HA mAb-HRP (horseradish peroxidase) conjugate (Roche) and incubated at room temperature for 30 min to allow complex formation between the translation reaction products and the antibody-HRP conjugate. Pre-formed $V_\kappa$ dAb-3F10 mAb-HRP (Cat.: 2 013 819) complexes were thereafter aliquoted into the pre-coated plate at 50 µl per well and allowed to bind to the immobilised antigen for 30 min at room temperature. Unbound material was removed and the wells were washed four times with PBS/0.1% Tween 20. HRP activity was measured by adding 50 µl/well of SureBlue substrate (KPL Laboratories). The reactions were stopped by adding 50 µl of 2M $H_2SO_4$ and read immediately at 405 nm platereader (Molecular Devices). As it can be seen on FIG. 15, the protein L-binding activity of the polyclonal selected population remains largely invariable throughout selection while, beginning from the fourth round of selection, the CIAP-binding activity becomes detectable above background. It should be noted that the presence of scArc at the C-terminus of $V_\kappa$ dAb does not compromise its protein L-binding activity, as demonstrated for Sample 1 on FIG. 4.

Figure 16:
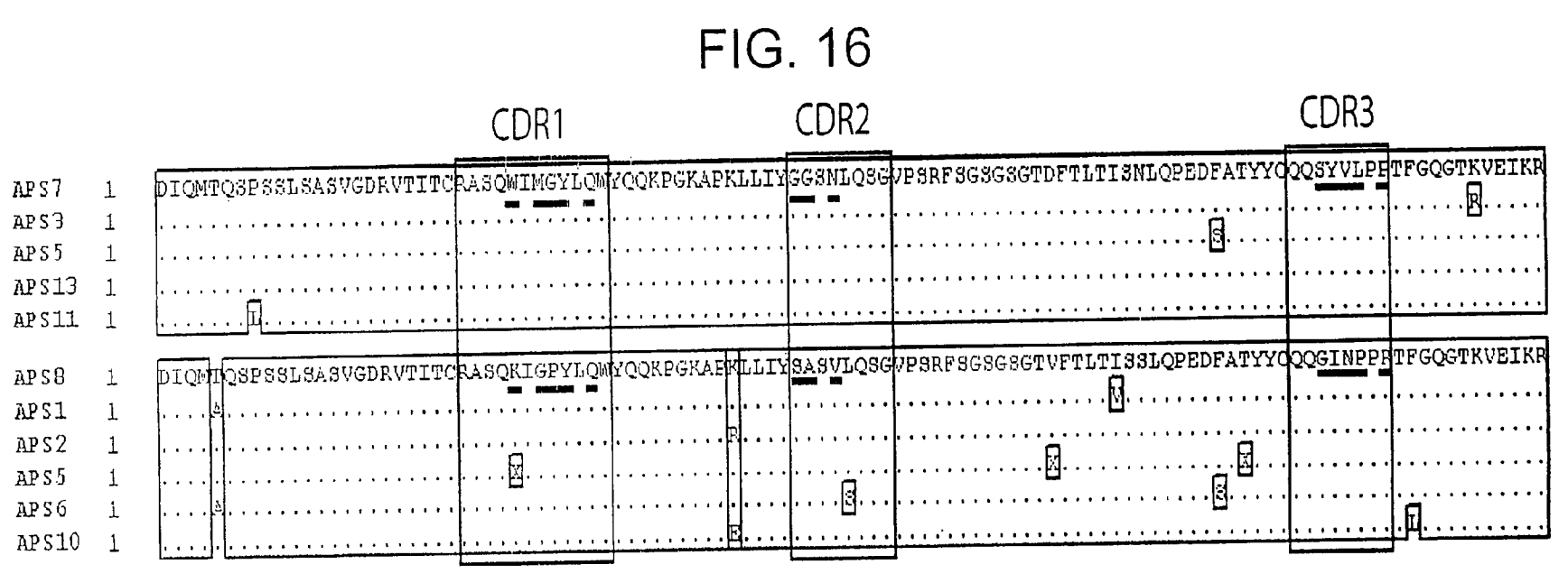

The DNA recovered in the final round of selection on CIAP was PCR-amplified from a 1 µl aliquot of 1.7 nM library using primers AS251+AS252 and the cycling profile 25X60C1M. The resulting fragment was gel purified on 2% E-Gel cut of by Nco I/Not I cut and subcloned into an aliquot of the Nco I/Not I-digested pIE2 vector for further characterisation at clonal level. In vector pIE2 the VK domains are expressed without any DNA-binding domains in direct fusion to the C-terminal HA tag. In total 32 bacterial colonies were analysed for the insert using nested PCR with primers AS11+AS17, profile 20X60C2M, followed by 25 cycles with primers AS12+AS18 and the 25X60C2M profile. 30 clones out of 32 proved to have the insert as judged by the expected 1317 bp length of the PCR product. The first thirteen PCR fragments containing the $V_\kappa$ insert were used as templates for the in vitro translation reaction as described above for the polyclonal assay and analysed in similar manner by ELISA, using the biotinylated protein L, CIAP and β-galactosidase to assess the specificity of the clones. β-Galactosidase-specific clone $V_\kappa$(E5) served as a negative control. As it can be seen on FIG. 15, 11 $V_\kappa$ dAb clones out of 13 tested (85%) showed good binding to immobilised CIAP. All except one displayed no cross-reactivity with β-galactosidase and none bound to streptavidin. The $V_\kappa$ dAb inserts of all 11 binding clones were sequenced and found to encode two families differing from each other at all three CDRs (FIG. 16).

$V_\kappa$(APS7) and $V_\kappa$(APS8), two representative clones of both sets of sequences, were further assayed by ELISA serial dilution assay. Both conventional sandwich, and the modified "One-Step" ELISA protocols described above for the polyclonal $V_\kappa$ population analysis, were used and the results are presented on FIG. 17. Both clones were found give specific binding to CIAP even in highly diluted (100-500-fold) in vitro translation mixes when the single-step protocol was used, presumably due to avidity effect as a result of pre-complexing with bivalent rat mAb. Conventional sandwich ELISA "Two-step" protocol yielded specific binding in the conditions used only for $V_\kappa$(APS8), with detection threshold about 1000-fold worse than in the "Single-step" assay. Since in "Single-step" ELISA clone $V_\kappa$(APS7) gives lower ELISA readout and has about 10-fold lower detection threshold than than $V_\kappa$(APS8), it appears that the affinity of clone $V_\kappa$(APS7) is too low to be detectable by sandwich ELISA in the conditions used.

In summary, five rounds of selection from a naïve synthetic $V_\kappa$(G4) library yielded a population of clones by the end of the fifth round of selection, 85% of which were positive. Two distinct families of sequences were identified, with one of the two representative clones apparently having higher affinity for CIAP than the other.

Example 8

Construction of $V_h$ Domain Antibody Fusion Construct with scArc DNA-Binding Protein Successful emulsion-based in vitro selection of $V_\kappa$ domain antibodies in fusion to the N-terminus of scArc DNA-binding domain suggests that a similar approach can be used for the selection of $V_H$ domain antibodies as well. In this example, it is demonstrated how human heavy chain $V_H$(DOM1h-10-27) domain antibody, isolated from a phage display library against human TNF receptor, can be selectively enriched in a model selection from the excess of non-binding molecules.

Assembly of $V_H$(DOM1h-10-27)-scArc expression construct.

Figure 18:
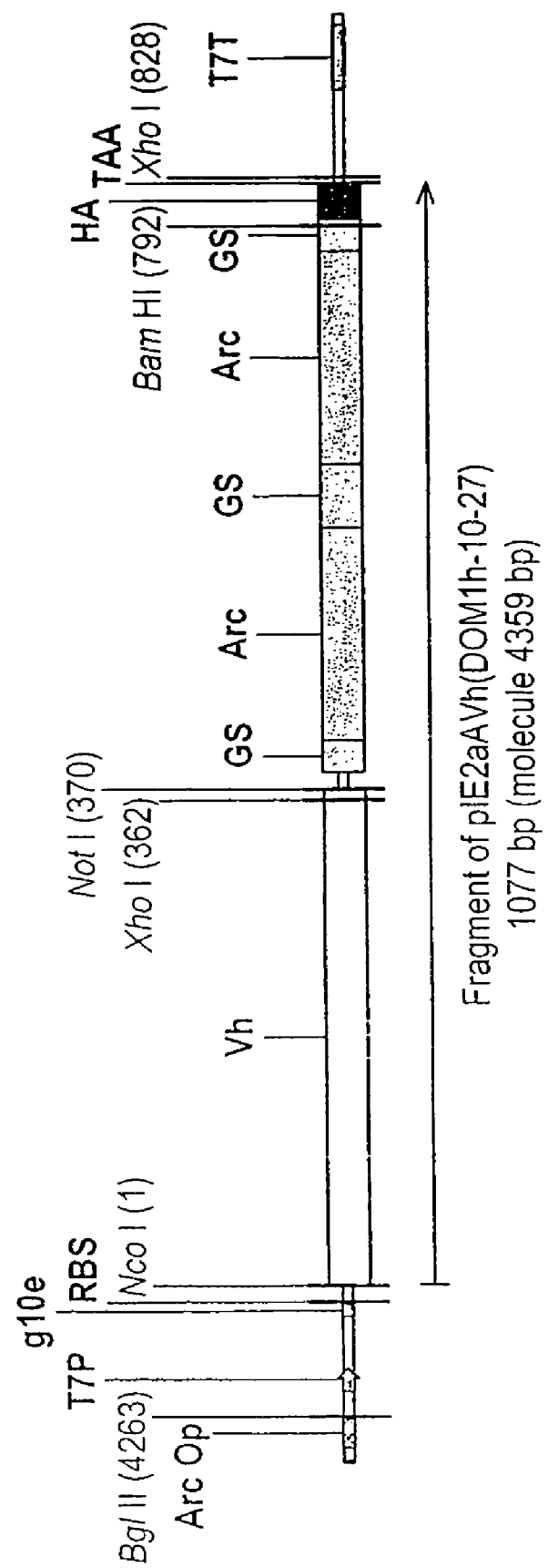
FIG. 18 The expression construct pIE2aAVh(DOM1h-10-27). A) The domain structure of the expression cassette, B) The sequence of the expression cassette. The sequences shown correspond to SEQ ID NOs 75 and 76.

Anti-human TNF Receptor $V_H$ clone (DOM1h-10-27) is cloned into the NcoI/NotI cut pIE2aA vector already harbouring the scArc construct at the BamHI and one Arc operator at the Bgl II site, yielding a $V_H$(DOM1h-10-27)-scArc fusion construct in the vector pIE2aAV$_H$(DOM1h-10-27). In this construct the Vh dAb is fused to the N-terminus of the scArc DNA-binding domain via a 8-amino acid flexible glycine-serine linker (FIG. 18).

Functional activity of $V_H$(DOM1h-10-27) domain antibody fusion construct with scArc DNA-binding protein.

The expression cassette of the vector pIE2aAV$_H$(DOM1h-10-27) encoding the model selection target molecule, was PCR-amplified from a 10 ng aliquot of the vector using primers AS11 and AS17 in the PCR cycling protocol 25X60C2M.

The resulting 1764 bp DNA fragment was run on a 1.2% E-Gel (Invitrogen) unit, cut out from the gel under UV illumination and purified using Qiagen Gel Extraction kit (Qiagen). The purified DNA fragment was quantified by UV spectroscopy and diluted to 1.7 nM final concentration in 0.2 mg/ml yeast tRNA (Sigma). The 1416 bp expression cassette of the vector pIE2aA, encoding the model selection competitor molecule scArc, was also —PCR-amplified from a 10 ng aliquot of the vector using primers AS11 and AS17 in the PCR cycling protocol 25X60C2M, purified on 1.2% E-Gel and diluted to 1.7 nM final concentration in 0.2 mg/ml yeast tRNA (Sigma).

The functional activity of the $V_H$(DOM1h-10-27)-scArc fusion protein can be assessed by PCR amplification of the DNA co-captured during the $V_H$-dependent immunoprecipitation of the in vitro translation reaction product. As in the case of $V_\kappa$-scArc fusion constructs, 1 µl of 1.7 nM template in 0.2 mg/ml tRNA is added to 25 µl EcoPro T7 in vitro translation mix (Novagen), supplemented with 0.75 µl of 100 mM oxidized glutathione (Sigma), and incubated at 25° C. for four hours. During the translation reaction the streptavidin-coated PCR tubes, cut from Strep Thermofast 96-well plates (Abgene), are first incubated at room temperature for three hours with 50 µl of at least 40 nM biotinylated target protein in PBS. The coating buffer is thereafter removed and any remaining free biotin-binding sites are blocked with a 15 min pulse of 50 µg/ml biotinylated BSA in PBS. The precoated wells are thereafter three times washed with PBS and then filled with 100 µl of binding buffer C+ (100 mM KCl, 20 mM Tris, 5 mM MgCl$_2$, 0.05% Tween 20, 0.05 mM EDTA, 1% BSA). Upon completion of the translation reaction the products are diluted in Buffer C+ and applied to the pre-coated and blocked PCR tubes, allowed to bind for 30 min at room temperature and washed 4 times with 150 µl of Buffer C+. The retained genetic elements are amplified with PCR using a nested set of primers AS12/AS18 and a 30-cycle PCR protocol 30X60C2M. In 30X60C2M protocol 50 µl PCR reactions contain 200 µM each of dATP dTTP dGTP dCTP (Amersham), 300 nM forward and reverse primers AS13+AS19 and 1 U of SuperTaq DNA polymerase (HT Biotechnology) in 1× polymerase Buffer (HT Biotechnology). Initial denaturation at 94° C. for 2 min is followed by 30 cycles of denaturation at 94° C. for 15 sec, annealing at 60° C. for 30 sec and extension at 72° C. for two minutes. Final extension is at 72° C. for 5 min, followed by a hold step at 10° C. The reaction products are separated thereafter by electrophoresis on a 1% agarose gel in 1×TAE buffer.

Figure 19:
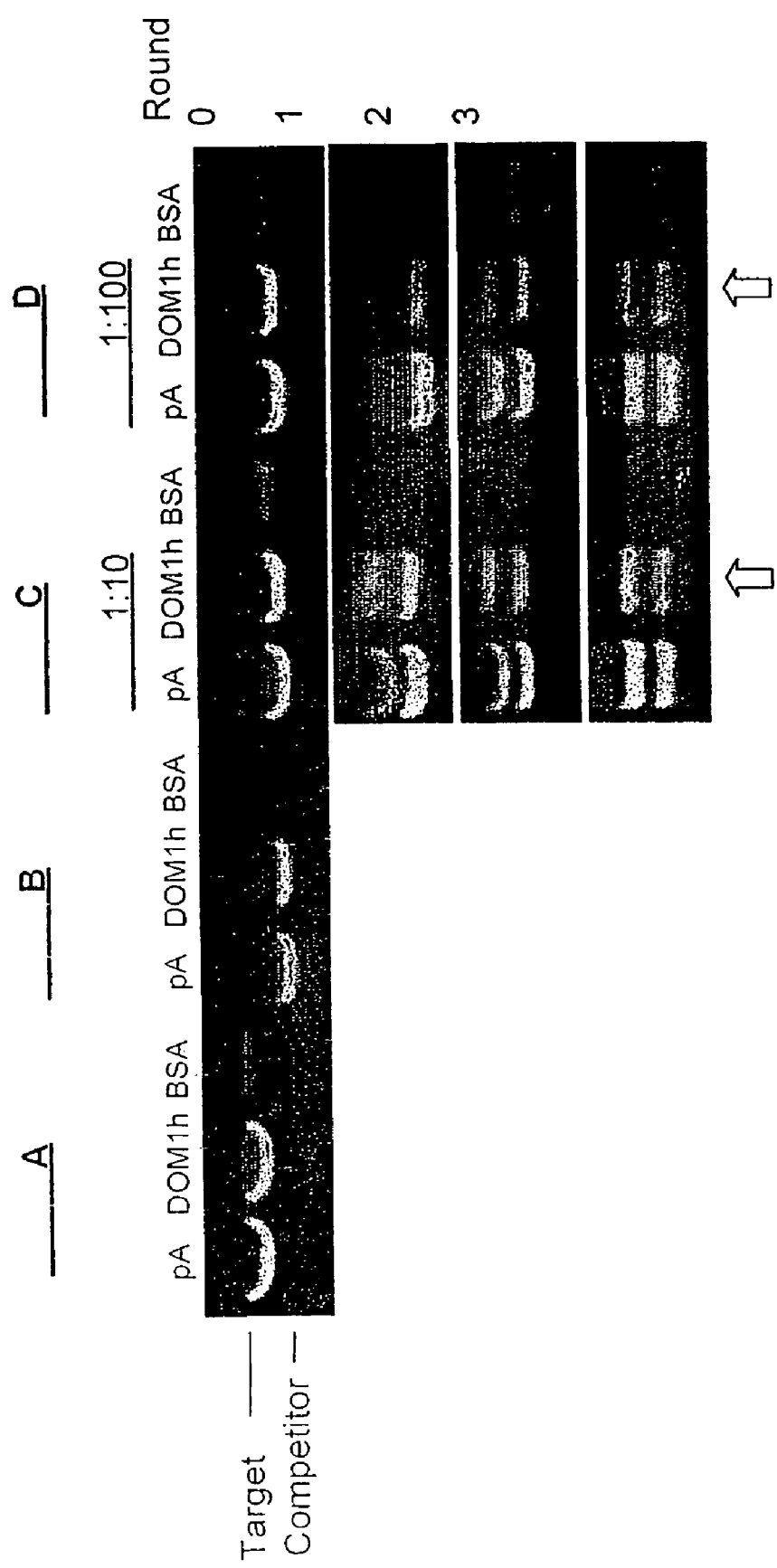
FIG. 19 The antigen-binding activities of the pIE2aAV$_h$(DOM1h-10-27)-encoded target protein V$_h$(DOM1h-10-27)-scArc and the pIE2aA-encoded competitor protein scArc. The pIE2aAV$_h$(DOM1h-10-27)-derived genetic elements expressing V$_h$(DOM1h-10-27)-scArc are efficiently captured on protein A and human TNF receptor-coated tubes, but not on the BSA-coated one. B) Compared with the V$_h$(DOM1h-10-27)-scArc target construct, the pIE2aA-derived competitor genetic elements expressing scArc are captured weakly on protein A, human TNF receptor and BSA. C and D) Sequential enrichment of the V$_h$(DOM1h-10-27)-scArc-encoding target construct from the excess of the scArc-encoding construct starting from 1:10 and 1:100 dilution as assayed by the protein A, human TNF receptor and BSA-binding activity of the mixed population: 0—starting library, 1—after one round of selection, 2—after two rounds of selection, 3—after three rounds of selection.

As it can be seen on panel A of FIG. 19, both immobilised biotinylated protein A and human TNF receptor, but not BSA, co-precipitated the DNA encoding the $V_h$(DOM1h-10-27)-scArc molecule. Protein A can be expected to interact both with the $V_h$ dAb as well as with the stabilizing 3F10 mAb, while human TNF receptor would interact only with $V_h$(DOM1h-10-27) dAb. BSA serves as a negative control for the non-specific binding of the DNA and protein-DNA complexes. In comparison, as it can be seen on panel B of FIG. 19, the control construct scArc, which lacks the $V_h$ domain, is captured much less efficiently on protein A and human TNF receptor-coated surfaces.

Model selection of $V_H$(DOM1h-10-27) domain antibody fusion construct with scArc DNA-binding protein.

An aliquot of the 1.7 nM solution of $V_H$(DOM1h-10-27)-scArc fusion protein expression construct was diluted either 10- or 100-fold into 1.7 nM solution of the DNA fragment encoding the scArc DNA-binding protein. Both solutions contained 0.2 mg/ml yeast tRNA as a carrier nucleic acid.

Emulsion selection experiments were set up as described in Example 4. In rounds 1 and 2, 0.5 µl of 1.7 nM library solution to 50 µl of in vitro translation mix was used, whilst in round 3 this was decreased five-fold, to improve segregation of the library. The genetic elements encoding $V_H$(DOM1h-10-27)-scArc can be sequentially enriched from the excess of scArc-encoding genetic elements by affinity purification of $V_H$(DOM1h-10-27)-scArc fusion protein, complexed with its encoding DNA, on solid surface immobilised human TNF receptor, the specific antigen of $V_H$(DOM1h-10-27). Sequential enrichment of the pIE2aA $V_H$(DOM1h-10-27)-derived target genetic construct over the competitor construct scArc, derived from pIE2aA, is demonstrated on FIG. 19. In this model selection the volume of the aqueous phase recovered from the emulsion was adjusted to 150 µl and allowed to bind in 50 µl aliquots in three different PCR tubes to streptavidin-captured biotinylated protein A, human TNF receptor and BSA. The surface-bound genetic elements were amplified in the first round of selection using primers AS12 and AS18, in the second round using primers AS14 and AS20, while in the final round primers AS15 and AS21 were used. In the amplification protocol 30X60C2M 50 µl PCR reactions contain 200 µM each of dATP, dTTP, dGTP and dCTP (Amersham), 300 nM forward and reverse primers and 1 U of SuperTaq DNA polymerase (HT Biotechnology) in 1× polymerase Buffer (HT Biotechnology). Initial denaturation at 94° C. for 2 min is followed by 35 cycles of denaturation at 94° C. for 15 sec, annealing at 60° C. for 30 sec and extension at 72° C. for two minutes. Final extension is at 72° C. for 5 min, followed by a hold step at 10° C. 10 µl aliquots of the amplification reaction products were run on 1% agarose gels and are shown on FIG. 19. The rest of the PCR product from the β-galactosidase-coated well was purified on 1.2% E-Gels (Invitrogen) and cut out on the UV transilluminator using a razor blade whilst making sure that the excised gel fragment was sufficiently large to contain both the target and the competitor genetic elements.

Approximately 5-10-fold enrichment of the pIE2aA$V_H$ (DOM1h-10-27)-derived target genetic element over the pIE2aA-derived competitor genetic element was observed in both cases, with 5×10$^8$ genetic elements dispersed in 50 µl aqueous phase.

Example 9

Genotype-Phenotype Linkage Between a Single-Chain Fv Fusion to scArc and its Encoding Gene pIE2aA, pIE2a2A, pIE2a3A and pIE2a4A were further modified through insertion of a linker sequence into the Not I site of the vectors. Linkers of the type A(EAAAK)$_n$A ($n$=2-5) have been characterised as being rigidly helical and capable of effectively separating the domains of bifunctional fusion proteins (Arai, R., H. Ueda, A. Kitayama, N. Kamiya and T. Nagamune (2001). "Design of the linkers which effectively separate domains of a bifunctional fusion protein." Protein Eng 14(8): 529-32). The nucleotide sequence encoding the (KEAAA)$_6$ linker is assembled by ligating the DNA duplex formed from the annealed phosphorylated oligonucleotides AS48 and AS49 into gel purified Not I-cut dephosphorylated pIE2aA, pIE2a2A, pIE2a3A and pIE2a4A in vitro expression vectors yielding pIE7'aA, pIE7'a2A, pIE7'a3A and pIE7'a4A. Typically both oligonucleotides used in a reaction are phosphorylated simultaneously in 50 µl volume at 2 µM concentration using 5 units of T4 polynucleotide kinase (NEB) in T4 DNA ligase buffer (NEB). Polynucleotide kinase is inactivated by 5 min incubation of the reaction mix at 95° C., followed by 30 nm in cooling step to 40° C. to allow the annealing of the oligonucleotides to take place. 0.1 µl aliquot of the annealed phosphorylated DNA duplex is added to 100 ng of digested and phosphorylated vector and ligated for 1 h at room temperature in 5 µl volume using 50 units of T4 DNA ligase (NEB). 0.5 µl aliquots of the ligation reaction are thereafter used to transform 5 µl aliquots of supercompetent XL-10 E. coli cells (Stratagene) according to the manufacturer's instructions. The sequences of the inserted fragments are verified by DNA sequencing of plasmid DNA minipreps (Qiagen) prepared from overnight cultures. Since the oligonucleotides AS48 and AS49 only encode (KEAAA)$_3$ linker, the procedure was repeated on vectors pIE7'aA, pIE7'a2A, pIE7'a3A and pIE7'a4A to yield the final constructs pIEaA, pIE7a2A, pIF7a3A and pIE7a4A.

Example 10

The Formation of Stable Genotype-Phenotype Linkage Between the scFv-scArc Fusion Protein and its Genetic Element Emulsion-based in vitro selection of scFv antibody fragments on the basis of the scFv antigen-binding activity requires that the formation of stable complex between the scFc-scArc fusion protein and its encoding DNA (the genetic element).

In order to demonstrate the formation of such protein-DNA complex, the fluoresceine-specific scFv clone 31IJ1 is cloned into Nco I/Not I-cut vectors pIE7aA, pIE7a2A, pIE7a3A and pIE7a4A to yield respectively pIE7aA-scFv(31IJ1), pIE7a2A-scFv(31IJ1), pIE7a3A-scFv(31IJ1) and pIE7a4A-scFv(31IJ1). The DNA template for the in vitro translation experiments is prepared by PCR using protocol 25X60C2M where 50 µl PCR reactions contain 200 µM each of dATP dTTP dGTP dCTP (Amersham), 300 nM forward and reverse primers AS11+AS17, 10 ng plasmid DNA template and 1 U pf SuperTaq DNA polymerase (HT Biotechnology) in 1× polymerase Buffer (HT Biotechnology). Initial denaturation at 94° C. for 2 min is followed by 25 cycles of denaturation at 94° C. for 15 sec, annealing at 60° C. for 30 sec and extension at 72° C. for two minutes. Final extension is at 72° C. for 5 min, followed by a hold step at 10° C. PCR products are gel purified, spectrophotometrically quantified and an aliquot diluted to 1.7 nM concentration in 0.2 mg/ml yeast tRNA (Sigma) as a carrier nucleic acid. The PCR amplification reaction product lengths for pIE7aA, pIE7a2A, pIE7a3A, pIE7a4A, pIE7aA-scFv(31IJ1), pIE7a2A-scFv(31IJ1), pIE7a3A-scFv(31IJ1) and pIE7a4A-scFv(31IJ1)-derived genetic elements are 1536, 1563, 1590, 1617, 2244, 2271, 2298 and 2325 bp respectively. The PCR fragments are gel-purified using 1.2% E-gels (Invitrogen) and Qiaquick gel extraction kits (Qiagen).

In the solution expression experiments 3 µl of 1.7 nM PCR-amplified pIE7aA, pIE7a2A, pIE7a3A, pIE7a4A, pIE7aA-scFv(31IJ1), pIE7a2A-scFv(31 Ul), pIE7a3A-scFv (31IJ1) or pIE7a4A-scFv(31IJ1) template in 0.2 mg/ml tRNA is added to 25 µl EcoPro T7 in vitro translation mix (Novagen), supplemented with 0.75 µl of 100 mM oxidized glutathione (Sigma) and 0.25 µl 50 µl/ml 3F10 αHA mAb (Roche). Each reactions is split into three 9 µl aliquots. Two of the three in vitro translation aliquots of pIE7aA-scFv(31IJ1), pIE7a2A-scFv(31IJ1), pIE7a3A-scFv(31IJ1) or pIE-7a4A-scFv(31IJ1) are immediately combined with the aliquots of pIE7aA, pIE7a2A, pIE7a3A or pIE7a4A expression reactions respectively, one before and the other after the four-hour incubation at 25° C.

During the translation reaction the streptavidin-coated PCR tubes, cut from Strep Thermofast 96-well plates (Abgene), are first incubated at room temperature for three hours with 50 µl of at least 40 nM biotinylated protein A (Sigma), protein L (Pierce) fluorescein (Molecular Probes) of BSA (Sigma) in PBS. The coating buffer is thereafter removed and any remaining free biotin-binding sites are blocked with a 15 min pulse of 50 µg/ml biotinylated BSA in PBS. The pre-coated wells are thereafter three times washed with PBS and then filled with 100 µl of binding buffer C+ (100 mM KCl, 20 mM Tris, 5 mM MgCl2, 0.05% Tween 20, 0.05 mM EDTA, 1% BSA).

Upon completion of the translation reaction the products are diluted in Buffer C+ and applied to the pre-coated and blocked PCR tubes, allowed to bind for 30 min at room temperature and washed 4 times with 150 µl of Buffer C+. The retained genetic elements are amplified with PCR using a nested set of primers AS79/AS80 and a 30-cycle PCR protocol 30X60C2M. In 30X60C2M protocol 50 µl PCR reactions contain 200 µM each of dATP dTTP dGTP dCTP (Amersham), 300 nM forward and reverse primers AS13+ AS19 and 1 U of SuperTaq DNA polymerase (HT Biotechnology) in 1× polymerase Buffer (HT Biotechnology). Initial denaturation at 94° C. for 2 min is followed by 30 cycles of denaturation at 94° C. for 15 sec, annealing at 60° C. for 30 sec and extension at 72° C. for two minutes. Final extension is at 72° C. for 5 min, followed by a hold step at 10° C. The PCR amplification reaction product lengths for pIE7aA, pIE7a2A, pIE7a3A, pIE7a4A, pIE7aA-scFv(31IJ1), pIE7a2A-scFv(31IJ1), pIE7a3A-scFv(31IJ1) and pIE7a4A-scFv(31IJ1)-derived genetic elements are 757, 784, 811, 838, 1465, 1492, 1519 and 1546 bp respectively.

Figure 21:
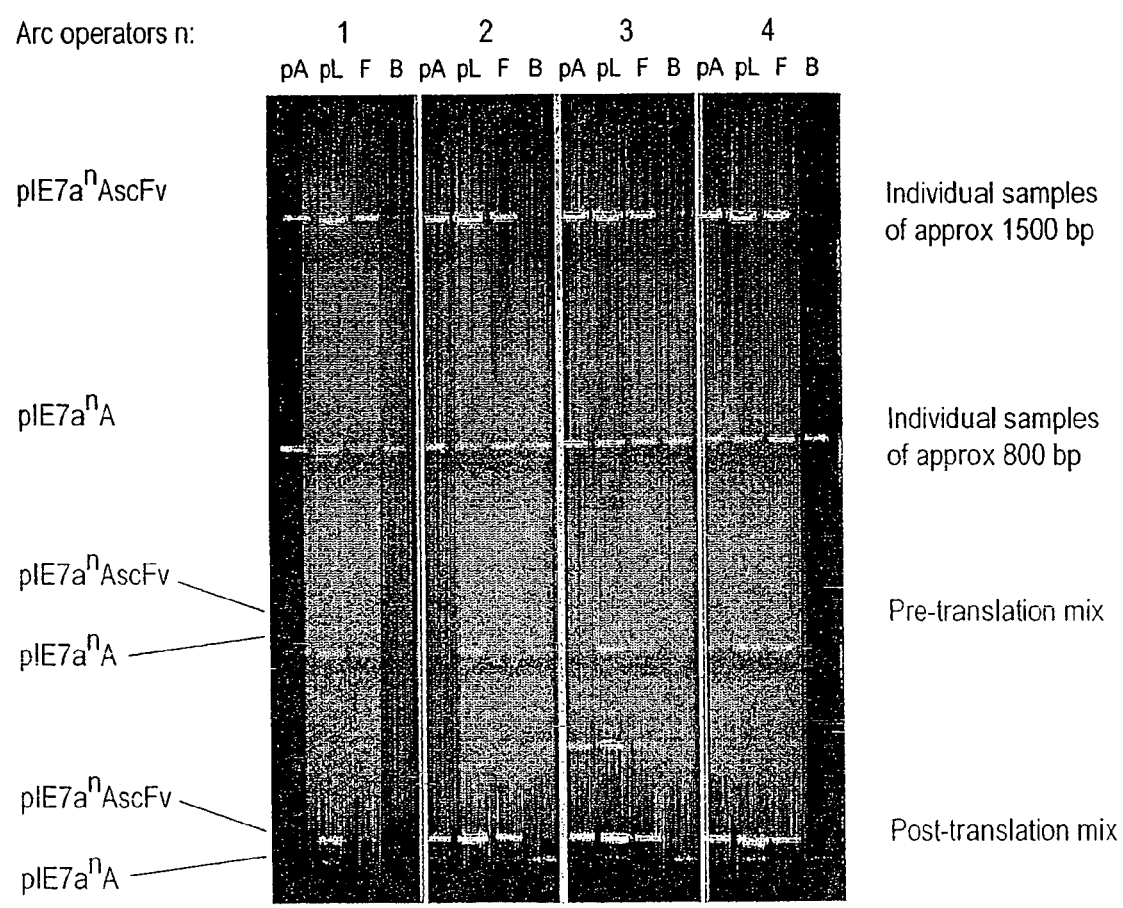
FIG. 21 scFv-scArc fusion protein-encoding genetic elements are efficiently recovered on protein A (pA), protein L (pL) and fluorescein (F) only when translated individually or from the post-translation mixes of translation reactions. There is specific recovery on PSA (B). There is improved recovery as the number of Arc operators per gene (n) is increased from 1 to 4.

As it can be seen on FIG. 21, the scFv-scArc proteins-DNA complexes show improved binding to specific ligands as protein A, protein L and fluorescein, whilst binding to the BSA-coated surface is minimal. Increase in the number of Arc operators on the genetic element improves the construct recovery, presumably through the avidity effect. In contrast, scArc complex with DNA is not effectively captured in these conditions because none of the reagents binds scArc. When the constructs pIE7aA-scFv(31IJ1), pIE7a2A-scFv(31IJ1), pIE7-a3A-scFv(31IJ1) or pIE7a4A-scFv(31IJ1) are co-translated with pIE7aA, pIE7a2A, pIE7a3A or pIE7a4A respectively both species of genetic elements are retained approximately in equal amounts. However, when the constructs are translated separately and combined immediately before the affinity purification step, there is improved recovery of the scFv-encoding constructs on the surfaces coated with specific ligands protein A, protein L and fluorescein. This indicates that scFv-scArc fusion protein can form complexes with its encoding genetic elements during the separate translations that are sufficiently stable to remain associated in the presence of excess of scArc proteins during the capture and washing steps. Increase in the number of Arc operators improves the yield of the scFv-encoding genetic elements, suggesting a role for the avidity effect. When both types of genetic elements are present during the reaction, like in the case of mixed templates, the genotype-phenotype linkage is not established and the ration of both templates is approximately the same on all surfaces.

All publications mentioned in the above specification are herein incorporated by reference. Various modifications and variations of the described methods and system of the invention will be apparent to those skilled in the art without departing from the scope and spirit of the invention. Although the invention has been, described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

```
SEQUENCES
Seq ID No. 1: DNA sequence of Arc operator
atgatagaagcactctactat

Seq ID No. 2: DNA sequence of Arc-operator fragment
atgatagaagcac

Seq ID No. 3: DNA sequence of Arc operator-fragment
agcactctactat

Seq ID No. 4: DNA sequence of scArc Repressor
atgaaaggaatgagcaaaatgccgcagttcaatttgcggtggcctagagaagtattggatttggtacgcaaggtagcggaagagaa
tggtcggtctgttaattctgagatttatcagcgagtaaggaaagctttaagaaggaagggcgcattggcgccggtggcggatcagg
cggtggatctggtggcggatcaggcggtggacatatgaaaggaatgagcaaaatgccgcagttcaatttgcggtggcctagagaa
gtattggatttggtacgcaaggtagcggaagagaatggtcggctgttaattctgagatttatcagcgagtaatggaaagctttaagaa
ggagggcgacattggcgcc Seq ID No 5: Protein sequence of scArc Repressor
MKGMSKMPQFNLRWPREVLDLAVRKVAEENGRSVNEIYQRVMESFKKEGRIGAG
GGSGGGSGGGSGGGHMKGMSKMPQFNLRWPREVLDLVRKVAEENGRSVNSEIY
QRVMESFKKEGRIGA Seq ID No 6: Primer AS1
catggggtcgaccatgcatggcggccgcaggatcccatcatcatcaccatcactaa Seq ID No 7: Primer AS2
gatcttagtgatggtgagatgatgggatcctgcggccgccatgcatggcgaccc Seq ID No 8: Primer AS5
catggggtcgaccggcggcgc Seq ID No 9: Primer AS6
ggccgcgccgccggtcgaccc
```

-continued

Seq ID No 10: Primer AS11
ttcgctattacgccagctgg

Seq ID No: PrimerAS12
aaaggggatgtgctgcaag

Seq ID No 12: Primer AS13
aaggcgattaagttgggtaac

Seq ID No 13: Primer AS14
ccagggttttcccagtcac

Seq ID No 14: Primer AS15
gagatggcgcccaacagtc

Seq ID No 15: Primer AS16
ctgccaccatacccacgcc

Seq ID No 16: Primer AS17
cagtcaggcaccgtgtatg

Seq ID No 17: Primer AS18
aacaatgcgctcatcgtcatc

Seq ID No 18: Primer AS19
tcggcaccgtcaccctgg

Seq ID No 19: Primer AS20
tgctgtaggcataggcttgg

Seq ID No 20: Primer AS21
cctcttgcgggatatcgtc

Seq ID No 21: Primer AS22
tccattccgacagcatcgc

Seq ID No 22: Primer AS29
gaaacaagcgctcatgagcc

Seq ID No 23: Primer AS51
tcgagagatcggttggcggatcaggcggtggacatatggagagagagattggcgccggtggcggatcaggcggtg Seq ID No 24: Primer AS52
gatccaccgcctgatccgccaccggcgccaatctctctctccatatgtccaccgcctgatccgccaccagatctc Seq ID No 25: Primer AS53
gagagagacatatgaaaggaatgagcaaaatgccgcagttcaatttgcggtggcctagagaagtattg Seq ID No 26: Primer AS54
ctgataaatctcagaattaacagaccgaccattctcttccgctaccttgcgtaccaaatccaatacttctctaggcca Seq ID No 27: Primer AS59
tgtggcaaggcgccaatgc Seq ID No 28: Primer AS60
gatctatgatagaagcactctactat Seq ID No 29: Primer AS61
gatccatagtagagtgcttctatcat Seq ID No 30: Primer AS62
aattctgagatttatcagcgagtaatggaaagctttaagaaggaagggcgcattggcgccttgccaca Seq ID No 31: Primer AS79
ggcgtagaggatcgagatc Seq ID No 32: Primer AS80
ttgttaccggatctctcgag Seq ID No 33: Primer AS93
catgagcggatccatggggtcgaccggcggcgcggccgcaa Seq ID No 34: Primer AS94
gatcttgcggccgcgccgccggtcgacccatggatccgct Seq ID No 35: Primer AS153
cagtcactatggcgtgctgc Seq ID No 36: Primer AS175
gatcctccgtttcgtgatgagtatagtagagtgcttctatcata -continued Seq ID No 37: Primer AS176
gatctatgatagaagcactctactatactcatcacgaaacggag Seq ID No 38: Primer AS251
cggtacccatggcgtcgacggacatccag Seq ID No 39: Primer AS252
aaggaaaaaagcggccgcccgtttgatttccac Seq ID No 40: Primer AS96
ggatgggagagcgatatagg Seq ID No 41: Primer AS263
ctctcgagttacgcataaccggcacatcatacggataggatcttgcggccgcccgtttgatttccaccttgg Seq ID No 42: Primer AS124
ggccgcaaaagaagcggcggcgaaagaagcggcggcgaaagaagcggcggcgaaagaatt Seq ID No 43: Primer AS125
ggccaattctttcgccgccgcttctttcgccgccgcttctttcgccgccgcttcttttgc Seq ID No 44: Primer AS171
ggccgccggtggcggatcaggcggtggatcggg Seq ID No 45: Primer AS172
Ggcccccgatccaccgcctgatccgccaccggc Seq ID No 46: Vk(E5) Nco I - Not I fragment
cggtttccctctagaaataattttgtttaactttaagaaggagatataccatggggtcgacggacatccagatgacccagtctccatcct
ccctgtctgcatctgtaggagacagagtcaccatcacttgccgggcaagtcagagcgttagcagctatttaaattggtatcagcagaa
accagggaaagcccctaagctcctgatctatcttgcatcccgtttgcaaagtggggtcccatcaaggttcagtggcagtggatctgg
gacagatttcactctcaccatcagcagtctgcaacctgaagattttgcaacttactactgtcaacagaattggtggctgcctcctacgtt
cggccaagggaccaaggtggaaatcaaacgggcggccgc Seq ID No 47: Vh(DOM1h-10-27) Nco I-Not I fragment
Ccatggccgaggtgcagctgttggagtctgggggaggcttggtacagcctggggggtccctgcgtctctcctgtgcagcctccgg
attcacctttgagtggtattggatgggttgggtccgccaggctccagggaagggtctagagtgggtctcagctatcagtggtagtggt
ggtagcacatactacgcagactccgtgaagggccggttcaccatctcccgcgacaattccaagaacacgctgtatctgcaaatgaa
cagcctgcgtgccgaggacgccgcggtatattactgtgcgaaagttaagttgggggggggcctaattttggctaccggggccag
ggaaccctggtcaccgtctcgagcgcggccgc Seq ID No 48: AS48
GGCCGCAAAAGAAGCGGCGGCGAAAGAAGCGGCGGCGAAAGAAGCGGCGGC
GAAAGAATT Seq ID No 49: AS49
ggccaattctttcgccgccgcttctttcgccgccgcttctttcgccgccgcttcttttgc Seq ID No 50: AS79
ggcgtagaggatcgagatc Seq ID No 51: AS80
ttgttaccggatctctcgag Seq ID No 52: scFv 31IJ1
atggccgaggtgcagctgttggagtctgggggaggcttggtacagcctgggggtccctgagactctcctgtgcagcctctggatt
cacctttagcagctatgccatgaagctgggtccgccaggctccagggaaggggctggagtgggtctcagggattaatcatgcgggt
gttcgtacatggtacgcagactccgtgaagggccggttcaccatctccagagacaattccaagaacacgctgtatctgcaaatgaac
agcctgagagccgaggacacggccgtatattactgtgcgaaacgtaaggtggggtttgactactggggtccagggaaccctggtca
ccgtctcgagcggtggaggcggttcaggcggaggtggcagcggcggtggcggtcgacggacatccagatgacccagtctcca
tcctccctgtctgcatctgtaggagacagagtcaccatcacttgccgggcaagtcagagcattagcagctatttaaattggtatcagca
gaaaccagggaaagcccctaagctcctgatctatgctgcatccagtttgcaaagtggggtcccatcaaggttcagtggcagtggatc
tgggacagatttcactctcaccatcagcagtctcaacctgaagattttgcaacttactactgtcaacagagttacagtaccccctaatac
gttcggccaagggaccaaggtggaaatcaaacgg Seq ID No 53: scFv 31IJ1
MAEVQLLESGGGLVQPGGSLRLSCAASGFTFSSYAMSWVRQAPGKGLEWVSGIN
HAGVRTWYADSVKGRFTISRDNSKNTLYLQMNSLRAEDTAVYYCAKRKVGFDY
WGQGTLVTVSSGGGGSGGGGSGGGGSTDIQMTQSPSSLSASVGDRVTITCRASQSI
SSYLNWYQQKPGKAPKLLIYAASSLQSGVPSRFSGSGSGTDFTLTISSLQPEDFATY
YCQQSYSTPNTFGQGTKVEIKR

REFERENCES

Anderson, C. W., Straus, J. W. and Dudock, B. S. (1983) Methods Enzymol; 101, 635-44.
Anderson, J. E. (1993) Curr. Op. Strict. Biol., 3, 24-30.
Ash, M. and Ash, 1. (1993) Handbook of industrial surfactants. Gower, Aldershot.
Baccanari, D. P., Averett, D., Briggs, C. and Burchall, J. (1977) Biochemistry, 16, 3566-72.
Barany, F. (1991) PCR Methods Applic., 1, 5-16.
Bass, S., Greene, R. and Wells, J. A. (1990)-Proteins, 8, 309-14.
Becher, P. (1957) Emulsions: theory and practice. Reinhold, N.Y.

Benita, S., Ed. (1996). Microencapsulation: methods and industrial applications. Drugs and pharmaceutical sciences Edited by Swarbrick, J. New York: Marcel Dekker.

Benner, S. A. (1994) Trends Biotechnol, 12, 158-63.

Berman, J., Eisenberg, S, and Tye, B. K. (1987) Methods Enzymol, 155, 528-37.

Betlach, L., Hershfield, V., Chow, L., Brown, W., Goodman, H. M. & Boyer, H. W. (1976). A restriction endonuclease analysis of the bacterial plasmid controlling the EcoRI restriction and modification of DNA. *Federation Proceedings* 35, 2037-2043.

Blattner, F. R. and Dahlberg, J. E. (1972) Nature New Biol, 237, 227-32.

Bougeleret, L., Schwarzstein, M. Tsugita, A. & Zabeau, M. (1984). Characterization of the genes coding for the Eco RV restrict-ion and modification system of *Escherichia coli*. *Nucleic Acids Res* 12(8), 3659-76.

Bru, R. & Walde, P. (1991). Product inhibition of alpha-chymotypsin in reverse micelles *Eur J Biochem* 199(1), 95-103.

Bru, R & Walde, P. (1993). Catalytic activity of elastase in reverse micelles. *Biochem Mol Biol Int* 31(4), 685-92.

Cahill, P., Foster, K. and Mahan, D. E. (1991) Clin Chem, 37, 1482-5.

Chakrabarti, A. C., Breaker, R. R., Joyce, G. F. & Deamer, D. W. (1994). Production of RNA by a polymerase protein encapsulated within phospholipid vesicles. *J Mol Evol* 39(6), 555-9.

Chamberlin, M. and Ring, J. (1973) J Biol Chem, 248, 2235-2244.

Chang, T. M. (1987). Recycling of NAD(P) by multienzyme systems immobilized by microencapsulation in artificial cells. Methods Enzymol 136(67), 67-82.

Chang, T. M. S. (1992). Recent advances in artificial cells based on microencapsulation. In *Microcapsules and nanoparticles in medicine and pharmacy* (Donbrow, M., ed.), pp. 323-339. CRC Press, Boca Raton, Fla.

Chapman, K. B. and Szostak, J. W. (1994) Curr. op. Struct. Biol., 4, 618-622.

Choo Y, Klug A. (1993) 21(15):3341-6.

Chetverin, A. B. and Spirin, A. S. (1995) Prog Nucleic Acid Res Mol Biol, 51, 225-70.

Clackson, T. and Wells, J. A. (1994) Trends Biotechnol, 12, 173-84.

Creagh, A. L., Prausnitz, J. M, & Blanch, H. W. (1993). Structural and catalytic properties of enzymes in reverse micelles. *Enzyme Microb Technol* 15(5), 3-83-92.

Cull, M. G., Miller, J. F. and Schatz, P. J. (1992) Proc Natl Acad Sci USA, 89, 1865-9.

Dickinson, E. (1994) In Wedlock, D. J. (ed.), Emulsions and droplet size control. Butterworth-Heine-mann, Oxford, Vol. pp. 191-257.

Ellington, A. D. and Szostak, J. W. (1990) Nature, 346, 81822.

Ellman, J., Mendel, D., Anthony, C. S., Noren, C. J. and Schultz, P. G. (1991) Methods Enzymol, 202, 301-36.

Fahy, E., Kwoh, D. Y. and Gingeras, T. R. (1991) PCR Methods Appl, 1, 25-33.

Fields, S. & Song, O. (1989) A novel genetic system to detect protein-protein interactions. *Nature* 340, 245-6.

Finch, C. A. (1993). Encapsulation and controlled release. *Spec. Publ.-R. Soc. Chem.* 138, 35.

Fisch, I., Kontermann, R. E., Finnern, R., Hartley, O., Soler, G. A., Griffiths, A. D. and Winter, G. (1996) Proc Natl Acad Sci USA, 93, 7761-6.

Freese, E. (1959) J. Mol. Biol., 1, 87.

Friedberg, E. C., Wallcer, G. C. and Siede, W. (1995) DNA repair and mutagenesis. ASM Press, Washington D.C.

Gold, L., Polisky, B., Uhlenbeck, O. and Yarus, M. (1995) Annu Rev Biochem, 64, 763-97.

Green, R. and Szostak, J. W. (1992) Science, 258, 1910-5.

Gregoriadis, G. (1976) Methods Enzymol, 44, 21 8-27.

Griffiths, A. D., Williams, S. C., Hartley, O., Tomlinson, I. M., Waterhouse, P., Crosby, W. L., Kontermann, R. E., Jones, P. T., Low, N. M., Allison, T. J. and et a.l. (1994) Embo *J*, 13, 3245-60.

Haber, J., Maslakiewicz, P., Rodakiewicz, N. J. & Walde, P. (1993). Activity and spectroscopic properties of bovine liver catalase in sodium bis(2-ethylhexyl)sulfosuccinate/isooctane reverse micelles. *Eur J Biochem* 217(2), 567-73.

Hermanson, G. T. (1996) Bioconjugate techniques. Academic Press, San Diego.

Hochuli, E., Dobeli, H. and Schacher, A. (1987) J Chromatogr, 411, 177-84.

Hoogenboom, H. R., et al., (1991) Nucl. Acids Res., 91, 4133-4137.

Hoogenboom, H. R. (1997). Designing and optimizing library selection strategies for generating high-affinity antibodies. *Trends Biotechnol.* 15, 62-70.

Hoogenboom, H. R (1997) Trends Biotechnol., 15, 62-70.

Hopp T P, Pricket K S, Price V L, Libby R T, March C J, Ceretti D P, Urdai D L, Conlon P J (1988) Bio/Technology 6:1204-1210.

Janda, K. D., Lo, L.-C., Lo, C.-H. L., Sim, M., -M., Wang, R., Wong, C.-H. and Lerner, R. A. (1997) Science, 275, 945-948.

Johannsson, A. (1991) In Price, C. P. and Newman, D. J. (ed.), Heterogeneous enzyme immunoassays. Stockton Press, New York, Vol. pp. 295-325.

Johannsson, A. and Bates, D. L. (1988) In Kemeny, D. M. and Challacombe, S. i. (ed.), Amplification by second enzymes. John Wiley, Chichester, Vol. pp. 85-106.

Joyce, G. F. (1994) *Curr. op. Structural Biol.*, 4, 331-336.

Kadir, F. H. and Moore, G. R. (1990) Febs Lett, 276, 81-4.

Kallen, R. G. & Jencks, W. P. (1966). The mechanism of the condensation of formaldehyde with tetrahydrofolic acid. *J. Biol. Chem.* 241, 5851-5863.

Karmirantzou M, Hamodraka S J. (2001) Protein Eng. July; 14(7):465-72.

Katanaev, V. L., Kurnasov, O. V. and Spirin, A. S. (1995) Febs Lett, 359, 89-92.

Keij, J. F., Groenewegen, A. C. & Visser, J. W. M. (1994) High-speed photodamage cell sorting: An evaluation of the ZAPPER prototype. *Methods in cell biology* 42, 371-358.

Klug, A. (1995) Ann NY Acad Sci, 758, 143-60.

Klug, A. and Schwabe, J. W. (1995) Faseb T, 9, 597-604.

Kolb, V. A., Makeyev, E. V., Kommer, A. and Spirin, A. S. (1995) Biochem Cell Biol, 73, 1217-20.

Kowalczykowski, S. C., Dixon, D. A., Eggleston, A. K., Lauder, S. D. and Rehrauer, W. M. (1994) Microbiol Rev, 58, 401-65.

Krumdiek, C. L. & Baugh, C. M. (1980) Solid-phase synthesis of pteroylpolyglutamates. Methods Enzymol. pp. 524-529

Kumar, A., Kumar, A. & Katiyar, S. S. (1989). Activity and kinetic characteristics of glutathione reductase in vitro in reverse micellar waterpool. *Biochim Biophys Acta* 996(1-2), 1-6.

Landegren, U., Kaiser, R., Sanders, J. and Hood, L. (1988) Science, 241, 1077-80.

Lesley, S. A., Brow, M. A. & Burgess, R. R. (1991). Use of in vitro protein synthesis from polymerase chain reaction-generated templates to study interaction of Escherichia

*coli* transcription factors with core RNA polymerase and for epitope mapping of monoclonal antibodies. *J Biol Chem* 266(4), 2632-8.

Lesley, S. A. (1995) Methods Mol Biol, 37, 265-78.

Lesley, S. A., Brow, M. A. and Burgess, R. R. (1991) J Biol Chem, 266, 2632-8.

Leung, D. W., Chen, E. and Goeddel, D. V. (1989) Technique, 1, 11-15.

Liao, H., McKenzie, T. and Hageman, R. (1986) Proc Natl Acad Sci USA, 83, 576-80.

Lim, F. & Sun, A. M. (1980). Microencapsulated islets as bioartificial endocrine pancreas. *Science* 210(4472), 908-10.

Lim, F., Ed. (1984). Biomedical applications of microencapsulation. Boca Raton, Fla.: CRC Press.

Lissant, K. J., ed Emulsions and emulsion technology. Surfactant Science New York: Marcel-Dekker, 1974.

Lissant, K. J., ed. Emulsions and emulsion technology. Surfactant Science New York: Marcel Dekker, 1974.

Lissant, K. J., ed. Emulsions and emulsion technology. Surfactant Science New York: Marcel Dekker, 1984.

Low, N. M., Holliger, P. H. and Winter, G. (1996) J Mol Biol, 260, 359-68.

Lowman, H. B., Bass, S. H., Simpson, N. and Wells, J. A. (1991) Biochemistry, 30, 10832-8.

Luisi, P. L. & B., S.-H. (1987). Activity and conformation of enzymes in reverse micellar solutions. *Methods Enzymol* 136(188), 188-216.

Ma, C., Kudlicki, W., Odom, O. W., Kramer, G. and Hardesty, B. (1993) Biochemistry, 32, 7939-45.

Magdassi, S., Frenkel, M., Carti, N. and Cazan, R. (1984) 97, 377-379.

Manley, J. L., Fire, A., Samuels, M. and Sharp, P. A. (1983) Methods Enzymol, 101, 568-82.

Mao, Q. & Walde, P. (1991). Substrate effects on the enzymatic activity of alpha-chymotrypsin in reverse micelles. *Biochem Biophys Res Commun* 178(3), 1105-12.

Mao, Q., Walde, P. & Luisi, P. L. (1992). Kinetic behaviour of alpha-chymotrypsin in reverse micelles. A stopped-flow study. *Eur J Biochem* 208(1), 165-70.

Mattheakis, L. C., Bhatt, R. R. and Dower, W. J. (1994) Proc Natl Acad Sci USA, 91, 9022-6.

McCafferty, J., Griffiths, A. D., Winter, G. and Chiswell, D. J. (1990) Nature, 348, 552-4.

Melton, D. A., Krieg, P. A., Rebagliati, M. R., Maniatis, T., Zinn, K. and Green, M. R. (1984) Nucleic Acids Res, 12, 703556.

Mendel, D., Cornish, V. W. and Schultz, P. G. (1995) Annu Rev Biophys Biomol Struct, 24, 435-62.

Menger, F. M. & Yamada, K. (1979). *J. Am. Chem. Soc.* 101, 6731-6734.

Miele, E. A., Mills, D. R. and Kramer, F. R. (1983) J Mol Biol, 171, 281-95.

Miller J, McLachlan A D, Klug A. (1984) EMBO J. 1985 June; 4(6):1609-14.

Mize, P. D., Hoke, R. A., Linn, C. P., Reardon, J. E. and Schulte, T. H. (1989) Anal Biochem, 179, 229-35.

Montigiani, S., Neri, G., Neri, P. and Neri; D. (1996) J Mol Biol, 258, 6-13.

Moore, M. F. (1995) Nature, 374, 766-7.

Moore M, Choo Y, Klug A. (2001) 98(4), 1432-6.

New, R. W. C., Ed. (1990). Liposomes: a practical approach. The practical approach series. Edited by Rickwood, D. & Hames, B. D. Oxford: Oxford University Press.

Nissim, A., Hoogenboom, H. R. I Tomlinson, I. M., Flynn, G., Midgley, C., Lane, D. and Winter, G. (1994) Embo J, 13, 692-8.

Oberholzer, T., Albrizio, M. & Luisi, P. L. (1995a). Polymerase chain reaction in liposomes. *Chemistry and Biology* 2, 677-682.

Oberholzer, T., Wick, R., Luisi, P. L. & Biebricher, C. K. (1995b). Enzymatic RNA replication in self-reproducing vesicles: an approach to a minimal cell. *Biochem Biophys Res Commun* 207(1), 250-7.

Parmley, S. F. and Smith, G. P. (1988) Gene, 73, 305-18.

Pelham, H. R. and Jackson, R. J. (1976) Eur J Biochem, 67, 247-56.

Perelson, A. S. and Oster, G. F. (1979) J Theor Biol, 81, 64570.

Perez, G. M., Sanchez, F. A. & Garcia, C. F. (1992). Application of active-phase plot to the kinetic analysis of lipoxygenase in reverse micelles. *Biochem J*.

Pirrung, M. C. and Huang, C. Y. (1996) Bioconjug Chem, 7, 31721.

Posner, B. A., Li, L., Bethell, R., Tsuji, T. and Benkovic, S. J. (1996) Biochemistry, 35, 1653-63.

Raumann, B. E., Rould, M. A., Pabo, C. O. And Sauer, R. T. (1994) *Nature* 367, 6465, 754-7.

Roberts, B. E., Gorecki, M., Mulligan, R. C., Danna, K. J., Rozenblatt, S. and Rich, A. (1975) Proc Natl Acad Sci USA, 72, 1922-6.

Roberts, J. W. (1969) Nature, 224, 1168-74.

Roberts, R & Szostak, J. (1997) RNA-peptide fusions for the in vitro selection of peptides and proteins. *Proc Natl Acad Sci USA* 94, 12297-12302.

Robinson, C. R. and R. T. Sauer (1996), Biochemistry 35(1), 109-16.

Rosenberg, M., Weissman, S, and Decrombrugghe, B. (1975) J Biol Chem, 250, 4755-64.

Ryabova, L. A., Desplancq, D., Spirin, A. S. And Pluckthun (1997) Nat Biotechnol 15(1): 79-84.

Saiki, R. K., Gelfand, D. H., Stoffel, S., Scharf, S. J., Higuchi, R., Horn, G. T., Mullis, K. B. and Erlich, H. A. (1988) Science, 239, 487-91.

Sambrook, J., Fritsch, E. F. and Maniatis, T. (1989) Molecular cloning: a laboratory manual. Cold Spring Harbor Laboratory Press, New York.

Savage, M. D., Mattson, G., Desai, S., Nielander, G. W., Morgensen, S, and Conklin, E. J. (1994) Avidin-biotin chemistry: a handbook. Pierce Chemical Company, Rockford.

Schick, M. J. (1966) Nonionic surfactants. Marcel Dekker, New York.

Sherman, P. (1968) Emulsion science. Academic Press, London.

Smith, G. P. (1985) Science, 228, 1315-7.

Smith, T. L. and R. T. Sauer (1996). "Role of operator subsites in Arc repression." *J Mol Biol* 264(2): 233-42.

Soumillion, P., Jaspers, L., Bouchet, M., Marchand, B. J., Winter, G. and Fastrez, J. (1994) J Mol Biol, 237, 415-22.

(Speight, R. E., Hart, D. J., Sutherland, J. D. and Blackburn, J. M. (2001) Chem & Biol 8, 951-956.

Stemmer, W. P. (1994a) Nature, 370, 389-91.

Stemmer, W. P. (1994b) Proc Natl Acad Sci USA, 91, 10747-51.

Stofko, H. R., Carr, D. W. and Scott, J. D. (1992) Febs Lett, 302, 274-8.

Sun, A. M., Vasek, I. & Tai, I. (1992). Microencapsulation of living cells and tissues. In *Microencapsulation and nanoparticles in medicine and pharmacy* (Donbrow, M., ed.), pp. 315-322. CRC Press, Boca Raton, Fla.

Sundberg, S. A., Barrett, R. W., Pirrung, M., Lu, A. L., Kiangsoontra, B. and Holmes, C. P. (1995) J. Am. CheM. Soc., 117, 12050-12057.

Tawfik, D. S., Green, B. S., Chap, R., Sela, N. & Eshhar, Z. (1993). catELISA: a facile general route to catalytic antibodies. *Proc Natl Acad Sci USA* 90(2), 373-7.

Tokatlidis, K., Friguet, B., Deville, B. D., Baleux, F., Fedorov, A. N., Navon, A., Djavadi, O. L. and Goldberg, M. E. (1995) Philos Trans R Soc Lond B Biol Sci, 348, 89-95.

Tripet, B., Yu, L., Bautista, D. L., Wong, W. Y., Irvin, R. T. and Hodges, R. S. (1996) Protein Engng., 9, 1029-1042.

Tuerk, C. and Gold, L. (1990) Science, 249, 505-10.

van Hal, D. A., Bouwstra, J. A. & Junginger, H. E. (1996). Nonionic surfactant vesicles containing estradiol for topical application. In *Microencapsulation: methods and industrial applications* (Benita, S., ed.), pp. 329-347. Marcel Dekker, New York.

Walde, P., Goto, A., Monnard, P.-A., Wessicken, M. & Luisi, P. L. (1994). Oparin's reactions revisited: enzymatic synthesis of poly(adenylic acid) in micelles and self-reproducing vesicles. *J. Am. Chem. Soc.* 116, 7541-7547.

Walde, P., Han, D. & Luisi, P. L. (1993). Spectroscopic and kinetic studies of lipases solubilized in reverse micelles. *Biochemistry* 32(15), 4029-34.

Walde, P., Peng, Q., Fadnavis, N. W., Battistel, E. & Luisi, P. L. (1988). Structure and activity of trypsin reverse micelles. *Eur. J Biochem* 173(2); 401-9.

Walker, G. T., Fraiser, M. S., Schram, J. L., Little, M. C, Nadeau, J. G. and Malinowski, D. P. (1992) Nucleic Acids Res, 20, 1691-6.

Weil, P. A., Luse, D. S., Segall, J. and Roeder, R. G. (1979) Cell, 18, 469-84.

Whateley, T. L. (1996). Microcapsules: preparation by interfacial polymerisation and interfacial complexation and their applications. In *Microencapsulation: methods and industrial applications* (Benita, S., ed.), pp. 349-375. Marcel Dekker, New York.

Wick, R. & Luisi, P. L. (1996). Enzyme-containing liposomes can endogenously produce membrane-constituting lipids. *Chem Biol* 3(4), 277-85.

Widersten, M. and Mannervik, B. (1995) J Mol Biol, 250, 115-22.

Williams, J. W., Morrison, J. F. and Duggleby, R. G. (1979) Biochemistry, 18, 2567-73.

Wilson I A, Niman H L, Houghten R A, Cherenson A R, Connolly M L, Lerner R A. (1984) The structure of an antigenic determinant in a protein. Cell, 37(3), 767-78.

Winter, G., Griffiths, A. D., Hawkins, R. E. and Hoogenboom, H. R. (1994) Annu Rev Immunol, 12, 433-55.

Wolfe, S. A., R. A. Grant, Pabo, C. (2003). "Structure of a designed dimeric zinc finger protein bound to DNA." Biochemistry, 42(46): 13401-9).

Wyatt, J. R. I Chastain, M. and Puglisi, J. D. (1991) Biotechniques, 11, 764-9.

Yamagishi, J., Kawashima, H., Matsuo, N., Ohue, M., Yamayoshi, M., Fukui, T., Kotani, H., Furuta, R., Nakano, K. and Yamada, M. (1990) Protein Eng, 3, 713-9.

Yelamos, J., Klix, N., Goyenechea, B., Lozano, F., Chui, Y. L., Gonzalez, F. A., Pannell, R., Neuberger, M. S. and Milstein, C. (1995) Nature, 376, 225-9.

Zaccolo, M., Williams, D. M., Brown, D. M. and Gherardi, E. (1996) J Mol Biol, 255, 589-603.

Zakrzewski, S. F. (1980) Preparation of tritiated dihydrofolic acid of high specific activity. Methods Enzymol. pp. 539-.

Zaug, A. J. and Cech, T. R. (1986) Biochemistry, 25, 4478-82.

Zaug, A. J. and Cech, T. R. (1986) Science, 231, 470-5.

Zaug, A. J., Been, M. D. and Cech, T. R. (1986) Nature, 324, 429-33.

Zubay, G. (1973) Annu Rev Genet, 7, 267-87.

Zubay, G. (1980) Methods Enzymol, 65, 856-77.

---

The invention claimed is:

1. An isolated nucleotide sequence encoding at least one Arc DNA binding domain, at least one Arc DNA binding site and at least one polypeptide domain that is an antibody domain, or an antigen binding fragment thereof, that is fused to the at least one Arc DNA binding domain.

2. The isolated nucleotide sequence of claim 1, wherein the antibody domain is selected from the group consisting of a $V_L$, $V_H$, Camelid $V_{HH}$ domain, scFv, antibody single variable domain and V-linker-V.

3. The isolated nucleotide sequence of claim 2, wherein the nucleotide sequence comprises a tag sequence.

4. The isolated nucleotide sequence of claim 3, wherein the tag sequence is included at the 3' end of the nucleotide sequence.

5. The isolated nucleotide sequence of claim 4, wherein the tag sequence encodes a polypeptide is selected from the group consisting of HA, FLAG and c-Myc.

6. The isolated nucleotide sequence of claim 2, wherein the nucleotide sequence encodes an antibody domain is fused to the N- or C-terminus of the at least one Arc DNA binding domain.

7. The isolated nucleotide sequence of claim 2, wherein the nucleotide sequence additionally comprises at least one linker.

8. The isolated nucleotide sequence of claim 2, wherein the antibody $V_L$ domain is $V_K$.

9. A construct comprising the isolated nucleotide sequence of claim 2.

10. A vector comprising the isolated nucleotide sequence of claim 2.

11. An isolated host cell comprising the construct of claim 9.

12. An isolated host cell comprising the vector of claim 10.

13. An isolated nucleotide sequence encoding at least one Arc DNA binding domain comprising the amino acid sequence shown in Seq ID No 5, at least one Arc DNA binding site and at least one polypeptide domain that is an antibody domain, or an antigen binding fragment thereof, that is fused to the at least one Arc DNA binding domain, wherein the antibody domain is selected from the group consisting of a $V_L$, $V_H$, Camelid $V_{HH}$ domain, scFv, antibody single variable domain and V-linker-V.

14. An isolated nucleotide sequence encoding 1, 2 or 3 Arc DNA-binding domains, at least one Arc DNA binding site and at least one polypeptide domain that is an antibody domain, or an antigen binding fragment thereof, that is fused to the at least one Arc DNA binding domain, wherein the antibody domain is selected from the group consisting of a $V_L$, $V_H$, Camelid $V_{HH}$ domain, scFv, antibody single variable domain and V-linker-V.

15. An isolated protein encoded by an isolated nucleotide sequence encoding at least one Arc DNA binding domain, at least one Arc DNA binding site and at least one polypeptide domain that is an antibody domain, or an antigen binding fragment thereof, that is fused to the at least one Arc DNA binding domain, wherein the antibody domain is selected from the group consisting of a $V_L$, $V_H$, Camelid $V_{HH}$ domain scFv, antibody single variable domain and V-linker-V; comprising the at least one Arc DNA binding domain fused to the at least one polypeptide domain that is an antibody domain, or an antigen binding fragment thereof.

16. An isolated protein-DNA complex comprising an isolated protein encoded by an isolated nucleotide sequence encoding at least one Arc DNA binding domain, at least one Arc DNA binding site and at least one polypeptide domain that is an antibody domain, or an antigen binding fragment thereof, that is fused to the at least one Arc DNA binding domain, wherein the antibody domain is selected from the group consisting of a $V_L$, $V_H$, Camelid $V_{HH}$ domain scFv antibody single variable domain and V-linker-V; said isolated protein comprising the at least one Arc DNA binding domain fused to the at least one polypeptide domain that is an antibody domain, or an antigen binding fragment thereof, wherein the isolated protein is bound to an Arc DNA binding site in the isolated nucleotide sequence.

17. An isolated protein-DNA complex comprising an isolated protein encoded by an isolated nucleotide sequence encoding at least one Arc DNA binding domain, at least one Arc DNA binding site and at least one polypeptide domain that is an antibody domain, or an antigen binding fragment thereof, that is fused to the at least one Arc DNA binding domain, wherein the antibody domain is selected from the group consisting of a $V_L$, $V_H$, Camelid $V_{HH}$ domain scFv antibody single variable domain and V-linker-V and wherein the isolated nucleotide sequence comprises a tag sequence encoding a polypeptide tag; said isolated protein comprising the at least one Arc DNA binding domain fused to the at least one polypeptide domain that is an antibody domain, or an antigen binding fragment thereof, and the polypeptide tag encoded by the tag sequence, wherein the isolated protein is bound to the at least one Arc DNA binding site in the isolated nucleotide sequence and a second protein bound to the polypeptide tag.

18. The isolated protein-DNA complex of claim 17, wherein the polypeptide tag is HA.

19. The isolated protein-DNA complex of claim 18, wherein the second protein bound to the polypeptide tag is an antibody.

20. The isolated protein-DNA complex of claim 19, wherein the antibody is a monoclonal antibody.

21. The isolated protein-DNA complex of claim 20, wherein the monoclonal antibody is selected from the group consisting of an αHA rat monoclonal antibody 3F10 and a monoclonal antibody that binds the same HA epitope as the αHA rat monoclonal antibody 3F10 and competes with αHA rat mAb 3F10 for binding to the same HA epitope.

22. A method for preparing an isolated protein-DNA complex comprising the steps of:
 (a) providing an isolated nucleotide sequence encoding at least one Arc DNA binding domain, at least one Arc DNA binding site and at least one polypeptide domain that is an antibody domain, or an antigen binding fragment thereof, that is fused to the at least one Arc DNA binding domain, wherein the antibody domain is selected from the group consisting of a $V_L$, $V_H$, Camelid $V_{HH}$ domain, scFv, antibody single variable domain and V-linker-V;
 (b) expressing the isolated nucleotide sequence to produce a polypeptide encoded by the isolated nucleotide sequence, said polypeptide comprising the at least one Arc DNA binding domain fused to the at least one polypeptide domain that is an antibody domain; and
 (c) allowing for the formation of the isolated protein-DNA complex; wherein the polypeptide encoded by the isolated nucleotide sequence is bound to an Arc DNA binding site in the isolated nucleotide sequence.

23. A method for preparing an isolated protein-DNA complex comprising the steps of:
 (a) providing an isolated nucleotide sequence encoding at least one Arc DNA binding domain, at least one Arc DNA binding site and at least one polypeptide domain that is an antibody domain, or an antigen binding fragment thereof, that is fused to the at least one Arc DNA binding domain, wherein the antibody domain is selected from the group consisting of a $V_L$, $V_H$, Camelid $V_{HH}$ domain scFv antibody single variable domain and V-linker-V and wherein the isolated nucleotide sequence comprises a tag sequence encoding a polypeptide tag;

(b) expressing the isolated nucleotide sequence to produce a polypeptide encoded by the isolated nucleotide sequence, said polypeptide comprising the at least one Arc DNA binding domain fused to the at least one polypeptide domain that is an antibody domain, or an antigen binding fragment thereof, and the polypeptide tag, in the presence of a protein that binds to the polypeptide tag; and (c) allowing for the formation of the isolated protein-DNA complex; wherein the polypeptide encoded by the isolated nucleotide sequence is bound to an Arc DNA binding site in the isolated nucleotide sequence and the protein is bound to the polypeptide tag.

24. The method of claim 23, wherein the polypeptide tag is HA.

25. The method of claim 23, wherein the protein is a monoclonal antibody.

26. The method of claim 25, wherein the monoclonal antibody is α-HA rat monoclonal antibody 3F10.

27. The method of claim 26, wherein the monoclonal antibody is at a concentration of about 3.4 nM.

28. The method of claim 27, wherein the isolated nucleotide sequence is expressed in the presence of glutathione.

29. The method of claim 28, wherein the glutathione is oxidised glutathione.

30. A method for isolating at least one nucleotide sequence encoding a polypeptide domain with a desired specificity, comprising the steps of:

(a) providing a nucleotide sequence encoding at least one Arc DNA binding domain, at least one Arc DNA binding site, and at least one polypeptide domain or a fragment thereof, a construct comprising said nucleotide sequence or a vector comprising said nucleotide sequence;

(b) compartmentalising the nucleotide sequence into microcapsules;

(c) expressing the nucleotide sequence to produce its respective polypeptide domain;

(d) pooling the microcapsules into a common compartment; and (e) selecting the nucleotide sequence which produces a polypeptide domain having the desired specificity.

31. The method according to claim 30, wherein the nucleotide sequence is expressed in the presence of glutathione.

32. The method according to claim 31, wherein the glutathione is oxidised glutathione.

33. The method according to claim 30 further comprising the additional step of:

(f) introducing at least one mutation into the polypeptide domain.

34. The method according to claim 30 further comprising iteratively repeating at least one of steps (a) to (e).

35. The method according to claim 30 further comprising amplifying the nucleotide sequence which produces the polypeptide domain having the desired specificity.

36. The method according to claim 30, wherein said at least one polypeptide domain is sorted by affinity purification.

37. The method according to claim 36 wherein said at least one polypeptide domain is sorted using protein L.

38. The method according to claim 30, wherein said at least one polypeptide domain is sorted by selective ablation of polypeptide domains that do not encode the desired polypeptide domain gene product.

39. A method for isolating at least one nucleotide sequence encoding a polypeptide domain with a desired specificity, comprising the steps of:

(a) providing a nucleotide sequence encoding at least one Arc DNA binding domain, at least one Arc DNA binding site, at least one polypeptide domain or a fragment thereof and a polypeptide tag, a construct comprising said nucleotide sequence or a vector comprising said nucleotide sequence;

(b) compartmentalizing the nucleotide sequence into microcapsules;

(c) expressing the nucleotide sequence to produce its respective polypeptide domain in the presence of a protein that binds to the polypeptide tag;

(d) pooling the microcapsules into a common compartment; and (e) selecting the nucleotide sequence which produces a polypeptide domain having the desired specificity.

40. The method of claim 39, wherein the polypeptide tag is HA.

41. The method of claim 40, wherein the protein is a monoclonal antibody.

42. The method of claim 41, wherein the monoclonal antibody is α-HA rat monoclonal antibody 3F10.

43. The method according to claim 42, wherein the monoclonal antibody is at a concentration of about 3.4 nM.

44. A method for preparing at least one polypeptide domain having a desired specificity, comprising the steps of:

(a) providing a plurality of nucleotide sequences, wherein each nucleotide sequence encodes at least one Arc DNA binding domain, at least one Arc DNA binding site, and at least one polypeptide domain or a fragment thereof, a plurality of constructs comprising each nucleotide sequence or a plurality of vectors comprising each nucleotide sequence;

(b) compartmentalizing each nucleotide sequence;

(c) expressing each nucleotide sequence to produce its respective gene product;

(d) sorting each nucleotide sequence that produces a polypeptide domain having the desired specificity; and (e) expressing at least one polypeptide domain having the desired specificity.

* * * * *

SEQUENCE LISTING

```
<160> NUMBER OF SEQ ID NOS: 87

<210> SEQ ID NO 1
<211> LENGTH: 21
<212> TYPE: DNA
<213> ORGANISM: Artificial
<220> FEATURE:
<223> OTHER INFORMATION: Bacteriophage p22 Arc operator

<400> SEQUENCE: 1
atgatagaag cactctacta t                                            21

<210> SEQ ID NO 2
<211> LENGTH: 13
<212> TYPE: DNA
<213> ORGANISM: Artificial
<220> FEATURE:
<223> OTHER INFORMATION: Bacteriophage p22 Arc operator fragment

<400> SEQUENCE: 2
atgatagaag cac                                                     13

<210> SEQ ID NO 3
<211> LENGTH: 13
<212> TYPE: DNA
<213> ORGANISM: Artificial
<220> FEATURE:
<223> OTHER INFORMATION: Bacteriophage p22 Arc operator fragment

<400> SEQUENCE: 3
```

```
agcactctac tat                                                        13
```

<210> SEQ ID NO 4
<211> LENGTH: 366
<212> TYPE: DNA
<213> ORGANISM: Artificial
<220> FEATURE:
<223> OTHER INFORMATION: Bacteriophage p22 scArc repressor

<400> SEQUENCE: 4

```
atgaaaggaa tgagcaaaat gccgcagttc aatttgcggt ggcctagaga agtattggat    60
ttggtacgca aggtagcgga agagaatggt cggtctgtta attctgagat ttatcagcga   120
gtaatggaaa gctttaagaa ggaagggcgc attggcgccg gtggcggatc aggcggtgga   180
tctggtggcg gatcaggcgg tggacatatg aaaggaatga gcaaaatgcc gcagttcaat   240
ttgcggtggc ctagagaagt attggatttg gtacgcaagg tagcggaaga gaatggtcgg   300
tctgttaatt ctgagattta tcagcgagta atggaaagct ttaagaagga agggcgcatt   360
ggcgcc                                                              366
```

<210> SEQ ID NO 5
<211> LENGTH: 122
<212> TYPE: PRT
<213> ORGANISM: Artificial
<220> FEATURE:
<223> OTHER INFORMATION: Bacteriophage p22 scArc repressor

<400> SEQUENCE: 5

```
Met Lys Gly Met Ser Lys Met Pro Gln Phe Asn Leu Arg Trp Pro Arg
1               5                   10                  15

Glu Val Leu Asp Leu Val Arg Lys Val Ala Glu Glu Asn Gly Arg Ser
            20                  25                  30

Val Asn Ser Glu Ile Tyr Gln Arg Val Met Glu Ser Phe Lys Lys Glu
        35                  40                  45

Gly Arg Ile Gly Ala Gly Gly Gly Ser Gly Gly Gly Ser Gly Gly Gly
    50                  55                  60

Ser Gly Gly Gly His Met Lys Gly Met Ser Lys Met Pro Gln Phe Asn
65                  70                  75                  80

Leu Arg Trp Pro Arg Glu Val Leu Asp Leu Val Arg Lys Val Ala Glu
                85                  90                  95

Glu Asn Gly Arg Ser Val Asn Ser Glu Ile Tyr Gln Arg Val Met Glu
            100                 105                 110

Ser Phe Lys Lys Glu Gly Arg Ile Gly Ala
        115                 120
```

<210> SEQ ID NO 6
<211> LENGTH: 56
<212> TYPE: DNA
<213> ORGANISM: Artificial
<220> FEATURE:
<223> OTHER INFORMATION: oligonucleotide amplification primer AS1

<400> SEQUENCE: 6

```
catggggtcg accatgcatg gcggccgcag gatcccatca tcatcaccat cactaa       56
```

<210> SEQ ID NO 7
<211> LENGTH: 56
<212> TYPE: DNA
<213> ORGANISM: Artificial
<220> FEATURE:
<223> OTHER INFORMATION: Oligonucleotide amplification primer AS2

```
<400> SEQUENCE: 7
gatcttagtg atggtgatga tgatgggatc ctgcggccgc catgcatggt cgaccc       56

<210> SEQ ID NO 8
<211> LENGTH: 21
<212> TYPE: DNA
<213> ORGANISM: Artificial
<220> FEATURE:
<223> OTHER INFORMATION: Oligonucleotide amplification primer AS5

<400> SEQUENCE: 8
catggggtcg accggcggcg c                                             21

<210> SEQ ID NO 9
<211> LENGTH: 21
<212> TYPE: DNA
<213> ORGANISM: Artificial
<220> FEATURE:
<223> OTHER INFORMATION: oligonucleotide amplification primer AS6

<400> SEQUENCE: 9
ggccgcgccg ccggtcgacc c                                             21

<210> SEQ ID NO 10
<211> LENGTH: 20
<212> TYPE: DNA
<213> ORGANISM: Artificial
<220> FEATURE:
<223> OTHER INFORMATION: oligonucleotide amplification primer AS11

<400> SEQUENCE: 10
ttcgctatta cgccagctgg                                               20

<210> SEQ ID NO 11
<211> LENGTH: 20
<212> TYPE: DNA
<213> ORGANISM: Artificial
<220> FEATURE:
<223> OTHER INFORMATION: oligonucleotide amplification primer AS12

<400> SEQUENCE: 11 aaaggggat gtgctgcaag                                                20

<210> SEQ ID NO 12
<211> LENGTH: 21
<212> TYPE: DNA
<213> ORGANISM: Artificial
<220> FEATURE:
<223> OTHER INFORMATION: oligonucleotide amplification primer AS13

<400> SEQUENCE: 12
aaggcgatta agttgggtaa c                                             21

<210> SEQ ID NO 13
<211> LENGTH: 19
<212> TYPE: DNA
<213> ORGANISM: Artificial
<220> FEATURE:
<223> OTHER INFORMATION: oligonucleotide amplification primer AS14

<400> SEQUENCE: 13
ccagggtttt cccagtcac                                                19

<210> SEQ ID NO 14
<211> LENGTH: 19
```

```
<212> TYPE: DNA
<213> ORGANISM: Artificial
<220> FEATURE:
<223> OTHER INFORMATION: oligonucleotide amplification primer AS15

<400> SEQUENCE: 14
gagatggcgc ccaacagtc                                                  19

<210> SEQ ID NO 15
<211> LENGTH: 19
<212> TYPE: DNA
<213> ORGANISM: Artificial
<220> FEATURE:
<223> OTHER INFORMATION: oligonucleotide amplification primer AS16

<400> SEQUENCE: 15
ctgccaccat acccacgcc                                                  19

<210> SEQ ID NO 16
<211> LENGTH: 19
<212> TYPE: DNA
<213> ORGANISM: Artificial
<220> FEATURE:
<223> OTHER INFORMATION: oligonucleotide amplification primer AS17

<400> SEQUENCE: 16
cagtcaggca ccgtgtatg                                                  19

<210> SEQ ID NO 17
<211> LENGTH: 21
<212> TYPE: DNA
<213> ORGANISM: Artificial
<220> FEATURE:
<223> OTHER INFORMATION: Oligonucleotide amplification primer AS18

<400> SEQUENCE: 17
aacaatgcgc tcatcgtcat c                                               21

<210> SEQ ID NO 18
<211> LENGTH: 18
<212> TYPE: DNA
<213> ORGANISM: Artificial
<220> FEATURE:
<223> OTHER INFORMATION: primer AS19

<400> SEQUENCE: 18
tcggcaccgt caccctgg                                                   18

<210> SEQ ID NO 19
<211> LENGTH: 20
<212> TYPE: DNA
<213> ORGANISM: Artificial
<220> FEATURE:
<223> OTHER INFORMATION: oligonucleotide amplification primer AS20

<400> SEQUENCE: 19
tgctgtaggc ataggcttgg                                                 20

<210> SEQ ID NO 20
<211> LENGTH: 19
<212> TYPE: DNA
<213> ORGANISM: Artificial
<220> FEATURE:
<223> OTHER INFORMATION: oligonucleotide amplification primer AS21

<400> SEQUENCE: 20
cctcttgcgg gatatcgtc                                                  19
```

```
<210> SEQ ID NO 21
<211> LENGTH: 19
<212> TYPE: DNA
<213> ORGANISM: Artificial
<220> FEATURE:
<223> OTHER INFORMATION: oligonucleotide amplification primer AS22

<400> SEQUENCE: 21
tccattccga cagcatcgc                                                    19

<210> SEQ ID NO 22
<211> LENGTH: 20
<212> TYPE: DNA
<213> ORGANISM: Artificial
<220> FEATURE:
<223> OTHER INFORMATION: oligonucleotide amplification primer AS29

<400> SEQUENCE: 22
gaaacaagcg ctcatgagcc                                                   20

<210> SEQ ID NO 23
<211> LENGTH: 75
<212> TYPE: DNA
<213> ORGANISM: Artificial
<220> FEATURE:
<223> OTHER INFORMATION: oligonucleotide amplification primer AS51

<400> SEQUENCE: 23
tcgagagatc tggtggcgga tcaggcggtg gacatatgga gagagagatt ggcgccggtg       60
gcggatcagg cggtg                                                        75

<210> SEQ ID NO 24
<211> LENGTH: 75
<212> TYPE: DNA
<213> ORGANISM: Artificial
<220> FEATURE:
<223> OTHER INFORMATION: oligonucleotide amplification primer AS52

<400> SEQUENCE: 24
gatccaccgc ctgatccgcc accggcgcca atctctctct ccatatgtcc accgcctgat       60
ccgccaccag atctc                                                        75

<210> SEQ ID NO 25
<211> LENGTH: 68
<212> TYPE: DNA
<213> ORGANISM: Artificial
<220> FEATURE:
<223> OTHER INFORMATION: oligonucleotide amplification primer AS53

<400> SEQUENCE: 25
gagagagaca tatgaaagga atgagcaaaa tgccgcagtt caatttgcgg tggcctagag       60
aagtattg                                                                68

<210> SEQ ID NO 26
<211> LENGTH: 78
<212> TYPE: DNA
<213> ORGANISM: Artificial
<220> FEATURE:
<223> OTHER INFORMATION: oligonucleotide amplification primer AS54

<400> SEQUENCE: 26
ctgataaatc tcagaattaa cagaccgacc attctcttcc gctaccttgc gtaccaaatc       60
caatacttct ctaggcca                                                     78
```

<210> SEQ ID NO 27
<211> LENGTH: 19
<212> TYPE: DNA
<213> ORGANISM: Artificial
<220> FEATURE:
<223> OTHER INFORMATION: oligonucleotide amplification primer AS59

<400> SEQUENCE: 27
tgtggcaagg cgccaatgc                                            19

<210> SEQ ID NO 28
<211> LENGTH: 26
<212> TYPE: DNA
<213> ORGANISM: Artificial
<220> FEATURE:
<223> OTHER INFORMATION: oligonucleotide amplification primer AS60

<400> SEQUENCE: 28
gatctatgat agaagcactc tactat                                    26

<210> SEQ ID NO 29
<211> LENGTH: 26
<212> TYPE: DNA
<213> ORGANISM: Artificial
<220> FEATURE:
<223> OTHER INFORMATION: oligonucleotide amplification primer AS61

<400> SEQUENCE: 29
gatccatagt agagtgcttc tatcat                                    26

<210> SEQ ID NO 30
<211> LENGTH: 68
<212> TYPE: DNA
<213> ORGANISM: Artificial
<220> FEATURE:
<223> OTHER INFORMATION: oligonucleotide amplification primer AS62

<400> SEQUENCE: 30
aattctgaga tttatcagcg agtaatggaa agctttaaga aggaagggcg cattggcgcc    60
ttgccaca                                                        68

<210> SEQ ID NO 31
<211> LENGTH: 19
<212> TYPE: DNA
<213> ORGANISM: Artificial
<220> FEATURE:
<223> OTHER INFORMATION: oligonucleotide amplification primer AS79

<400> SEQUENCE: 31
ggcgtagagg atcgagatc                                            19

<210> SEQ ID NO 32
<211> LENGTH: 20
<212> TYPE: DNA
<213> ORGANISM: Artificial
<220> FEATURE:
<223> OTHER INFORMATION: oligonucleotide amplification primer AS80

<400> SEQUENCE: 32
ttgttaccgg atctctcgag                                           20

<210> SEQ ID NO 33
<211> LENGTH: 41
<212> TYPE: DNA
<213> ORGANISM: Artificial

```
<220> FEATURE:
<223> OTHER INFORMATION: oligonucleotide amplification primer AS93

<400> SEQUENCE: 33
catgagcgga tccatggggt cgaccggcgg cgcggccgca a                    41

<210> SEQ ID NO 34
<211> LENGTH: 41
<212> TYPE: DNA
<213> ORGANISM: Artificial
<220> FEATURE:
<223> OTHER INFORMATION: oligonucleotide amplification primer AS94

<400> SEQUENCE: 34
gatcttgcgg ccgcgccgcc ggtcgacccc atggatccgc t                    41

<210> SEQ ID NO 35
<211> LENGTH: 20
<212> TYPE: DNA
<213> ORGANISM: Artificial
<220> FEATURE:
<223> OTHER INFORMATION: oligonucleotide amplification primer AS153

<400> SEQUENCE: 35
cagtcactat ggcgtgctgc                                            20

<210> SEQ ID NO 36
<211> LENGTH: 44
<212> TYPE: DNA
<213> ORGANISM: Artificial
<220> FEATURE:
<223> OTHER INFORMATION: oligonucleotide amplification primer AS175

<400> SEQUENCE: 36
gatcctccgt ttcgtgatga gtatagtaga gtgcttctat cata                 44

<210> SEQ ID NO 37
<211> LENGTH: 44
<212> TYPE: DNA
<213> ORGANISM: Artificial
<220> FEATURE:
<223> OTHER INFORMATION: oligonucleotide amplification primer AS176

<400> SEQUENCE: 37
gatctatgat agaagcactc tactatactc atcacgaaac ggag                 44

<210> SEQ ID NO 38
<211> LENGTH: 29
<212> TYPE: DNA
<213> ORGANISM: Artificial
<220> FEATURE:
<223> OTHER INFORMATION: oligonucleotide amplification primer AS251

<400> SEQUENCE: 38
cggtacccat ggcgtcgacg gacatccag                                  29

<210> SEQ ID NO 39
<211> LENGTH: 33
<212> TYPE: DNA
<213> ORGANISM: Artificial
<220> FEATURE:
<223> OTHER INFORMATION: oligonucleotide amplification primer AS252

<400> SEQUENCE: 39
aaggaaaaaa gcggccgccc gtttgatttc cac                             33
```

```
<210> SEQ ID NO 40
<211> LENGTH: 20
<212> TYPE: DNA
<213> ORGANISM: Artificial
<220> FEATURE:
<223> OTHER INFORMATION: oligonucleotide amplification primer AS96

<400> SEQUENCE: 40
ggatgggaga gcgatatagg                                               20

<210> SEQ ID NO 41
<211> LENGTH: 73
<212> TYPE: DNA
<213> ORGANISM: Artificial
<220> FEATURE:
<223> OTHER INFORMATION: oligonucleotide amplification primer AS263

<400> SEQUENCE: 41
ctctcgagtt acgcataatc cggcacatca tacggatagg atcttgcggc cgcccgtttg   60
atttccacct tgg                                                      73

<210> SEQ ID NO 42
<211> LENGTH: 60
<212> TYPE: DNA
<213> ORGANISM: Artificial
<220> FEATURE:
<223> OTHER INFORMATION: oligonucleotide amplification primer AS124

<400> SEQUENCE: 42
ggccgcaaaa gaagcggcgg cgaaagaagc ggcggcgaaa gaagcggcgg cgaaagaatt   60

<210> SEQ ID NO 43
<211> LENGTH: 60
<212> TYPE: DNA
<213> ORGANISM: Artificial
<220> FEATURE:
<223> OTHER INFORMATION: oligonucleotide amplification primer AS125

<400> SEQUENCE: 43
ggccaattct ttcgccgccg cttctttcgc cgccgcttct ttcgccgccg cttcttttgc   60

<210> SEQ ID NO 44
<211> LENGTH: 33
<212> TYPE: DNA
<213> ORGANISM: Artificial
<220> FEATURE:
<223> OTHER INFORMATION: oligonucleotide amplification primer AS171

<400> SEQUENCE: 44
ggccgccggt ggcggatcag gcggtggatc ggg                                33

<210> SEQ ID NO 45
<211> LENGTH: 33
<212> TYPE: DNA
<213> ORGANISM: Artificial
<220> FEATURE:
<223> OTHER INFORMATION: oligonucleotide amplification primer AS172

<400> SEQUENCE: 45
ggcccccgat ccaccgcctg atccgccacc ggc                                33

<210> SEQ ID NO 46
<211> LENGTH: 394
<212> TYPE: DNA
<213> ORGANISM: Artificial
<220> FEATURE:
<223> OTHER INFORMATION: Vk(E5) NcoI-NotI fragment
```

<400> SEQUENCE: 46

```
cggtttccct ctagaaataa ttttgtttaa ctttaagaag gagatatacc atggggtcga    60
cggacatcca gatgacccag tctccatcct ccctgtctgc atctgtagga cacagagtca   120
ccatcacttg ccgggcaagt cagagcgtta gcagctattt aaattggtat cagcagaaac   180
cagggaaagc ccctaagctc ctgatctatc ttgcatcccg tttgcaaagt ggggtcccat   240
caaggttcag tggcagtgga tctgggacag atttcactct caccatcagc agtctgcaac   300
ctgaagattt tgcaacttac tactgtcaac agaattggtg ctgcctcct acgttcggcc   360
aagggaccaa ggtggaaatc aaacgggcgg ccgc                               394
```

<210> SEQ ID NO 47
<211> LENGTH: 376
<212> TYPE: DNA
<213> ORGANISM: Artificial
<220> FEATURE:
<223> OTHER INFORMATION: Vh(DOM1h-10-27) NcoI-NotI fragment

<400> SEQUENCE: 47

```
ccatggccga ggtgcagctg ttggagtctg ggggaggctt ggtacagcct ggggggtccc    60
tgcgtctctc ctgtgcagcc tccggattca cctttgagtg gtattggatg ggttgggtcc   120
gccaggctcc agggaagggt ctagagtggg tctcagctat cagtggtagt ggtggtagca   180
catactacgc agactccgtg aagggccggt tcaccatctc ccgcgacaat tccaagaaca   240
cgctgtatct gcaaatgaac agcctgcgtg ccgaggacgc cgcggtatat tactgtgcga   300
aagttaagtt ggggggggggg cctaattttg gctaccgggg ccagggaacc ctggtcaccg   360
tctcgagcgc ggccgc                                                   376
```

<210> SEQ ID NO 48
<211> LENGTH: 60
<212> TYPE: DNA
<213> ORGANISM: Artificial
<220> FEATURE:
<223> OTHER INFORMATION: Oligonucleotide AS48

<400> SEQUENCE: 48

```
ggccgcaaaa gaagcggcgg cgaaagaagc ggcggcgaaa gaagcggcgg cgaaagaatt    60
```

<210> SEQ ID NO 49
<211> LENGTH: 60
<212> TYPE: DNA
<213> ORGANISM: Artificial
<220> FEATURE:
<223> OTHER INFORMATION: Oligonucleotide AS49

<400> SEQUENCE: 49

```
ggccaattct ttcgccgccg cttctttcgc cgccgcttct ttcgccgccg cttcttttgc    60
```

<210> SEQ ID NO 50
<211> LENGTH: 19
<212> TYPE: DNA
<213> ORGANISM: Artificial
<220> FEATURE:
<223> OTHER INFORMATION: Oligonucleotide AS79

<400> SEQUENCE: 50

```
ggcgtagagg atcgagatc                                                19
```

<210> SEQ ID NO 51
<211> LENGTH: 20

```
<212> TYPE: DNA
<213> ORGANISM: Artificial
<220> FEATURE:
<223> OTHER INFORMATION: Oligonucleotide AS80

<400> SEQUENCE: 51
ttgttaccgg atctctcgag                                              20

<210> SEQ ID NO 52
<211> LENGTH: 726
<212> TYPE: DNA
<213> ORGANISM: Artificial
<220> FEATURE:
<223> OTHER INFORMATION: scFv 31IJ1

<400> SEQUENCE: 52
atggccgagg tgcagctgtt ggagtctggg ggaggcttgg tacagcctgg ggggtccctg    60
agactctcct gtgcagcctc tggattcacc tttagcagct atgccatgag ctgggtccgc   120
caggctccag gaaggggct ggagtgggtc tcaggatta tcatgcggg tgttcgtaca      180 tggtacgcag actccgtgaa gggccggttc accatctcca gagacaattc caagaacacg   240
ctgtatctgc aaatgaacag cctgagagcc gaggacacgg ccgtatatta ctgtgcgaaa   300
cgtaaggtgg ggtttgacta ctggggccag ggaaccctgg tcaccgtctc gagcggtgga   360
ggcggttcag gcggaggtgg cagcggcggt ggcgggtcga cggacatcca gatgacccag   420
tctccatcct ccctgtctgc atctgtagga cagagtca ccatcacttg ccgggcaagt     480
cagagcatta gcagctattt aaattggtat cagcagaaac cagggaaagc ccctaagctc   540
ctgatctatg ctgcatccag tttgcaaagt ggggtcccat caaggttcag tggcagtgga   600
tctgggacag atttcactct caccatcagc agtctgcaac ctgaagattt tgcaacttac   660
tactgtcaac agagttacag taccctaat acgttcggcc aagggaccaa ggtggaaatc    720
aaacgg                                                             726

<210> SEQ ID NO 53
<211> LENGTH: 242
<212> TYPE: PRT
<213> ORGANISM: Artificial
<220> FEATURE:
<223> OTHER INFORMATION: scFV 31IJ1

<400> SEQUENCE: 53

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Gly Ile Asn His Ala Gly Val Arg Thr Trp Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Arg Lys Val Gly Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
```

```
                130                 135                 140
Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ser Tyr Ser Thr Pro Asn Thr Phe Gly Gln Gly Thr Lys Val Glu Ile
225                 230                 235                 240

Lys Arg

<210> SEQ ID NO 54
<211> LENGTH: 10
<212> TYPE: PRT
<213> ORGANISM: Artificial
<220> FEATURE:
<223> OTHER INFORMATION: C-myc motif

<400> SEQUENCE: 54

Glu Gln Lys Leu Ile Ser Glu Glu Asp Leu
1               5                   10

<210> SEQ ID NO 55
<211> LENGTH: 8
<212> TYPE: PRT
<213> ORGANISM: Artificial
<220> FEATURE:
<223> OTHER INFORMATION: Anti-FLAG-tag

<400> SEQUENCE: 55

Asp Tyr Lys Asp Asp Asp Asp Lys
1               5

<210> SEQ ID NO 56
<211> LENGTH: 9
<212> TYPE: PRT
<213> ORGANISM: Artificial
<220> FEATURE:
<223> OTHER INFORMATION: HA peptide sequence

<400> SEQUENCE: 56

Tyr Pro Tyr Asp Val Pro Asp Tyr Ala
1               5

<210> SEQ ID NO 57
<211> LENGTH: 287
<212> TYPE: DNA
<213> ORGANISM: Artificial
<220> FEATURE:
<223> OTHER INFORMATION: fragment of pIE2

<400> SEQUENCE: 57
tcgagatctc gatcccgcga aattaatacg actcactata gggagaccac aacggtttcc    60
ctctagaaat aattttgttt aactttaaga aggagatata ccatggggtc gaccggcggc   120
gcggccgcag gatcctatcc gtatgatgtg ccggattatg cgtaactcga gagatccggt   180
aacaaagccc gaaaggaagc tgagttggct gctgccaccg ctgagcaata actagcataa   240
ccccttgggg cctctaaacg gtcttgaggg gttttttgc tgaaagg                  287
```

```
<210> SEQ ID NO 58
<211> LENGTH: 20
<212> TYPE: PRT
<213> ORGANISM: Artificial
<220> FEATURE:
<223> OTHER INFORMATION: Fragment of pIE2

<400> SEQUENCE: 58

Met Gly Ser Thr Gly Gly Ala Ala Ala Gly Ser Tyr Pro Tyr Asp Val
1               5                   10                  15

Pro Asp Tyr Ala
            20

<210> SEQ ID NO 59
<211> LENGTH: 299
<212> TYPE: DNA
<213> ORGANISM: Artificial
<220> FEATURE:
<223> OTHER INFORMATION: Fragment of pIE3

<400> SEQUENCE: 59
tcgagatctc gatcccgcga aattaatacg actcactata gggagaccac aacggtttcc     60
ctctagaaat aatttgttt aactttaaga aggagatata ccatgagcgg atccatgggg    120
tcgaccggcg gcgcggccgc aagatcctat ccgtatgatg tgccggatta tgcgtaactc    180
gagagatccg gtaacaaagc ccgaaaggaa gctgagttgg ctgctgccac cgctgagcaa    240
taactagcat aaccccttgg ggcctctaaa cgggtcttga ggggtttttt gctgaaagg    299

<210> SEQ ID NO 60
<211> LENGTH: 24
<212> TYPE: PRT
<213> ORGANISM: Artificial
<220> FEATURE:
<223> OTHER INFORMATION: Fragment of pIE3

<400> SEQUENCE: 60

Met Ser Gly Ser Met Gly Ser Thr Gly Gly Ala Ala Ala Arg Ser Tyr
1               5                   10                  15

Pro Tyr Asp Val Pro Asp Tyr Ala
            20

<210> SEQ ID NO 61
<211> LENGTH: 203
<212> TYPE: DNA
<213> ORGANISM: Artificial
<220> FEATURE:
<223> OTHER INFORMATION: Fragment of pIE3aVk(E5)

<400> SEQUENCE: 61
atcgagatcc atagtagagt gcttctatca tagatctcga tcccgcgaaa ttaatacgac     60
tcactatagg gagaccacaa cggtttccct ctagaaataa ttttgtttaa ctttaagaag    120
gagatatacc atgagcggat ctggtggcgg atcaggcggt ggacatatga aggaatgag     180 caaaatgccg cagttcaatt tgc                                             203

<210> SEQ ID NO 62
<211> LENGTH: 203
<212> TYPE: DNA
<213> ORGANISM: Artificial
<220> FEATURE:
<223> OTHER INFORMATION: Fragment of pIE3a2AVk(E5)

<400> SEQUENCE: 62
```

```
atcgagatcc atagtagagt gcttctatca tagatcctcc gtttcgtgat gagtatagta    60
gagtgcttct atcatagatc tcgatcccgc gaaattaata cgactcacta tagggagacc   120
acaacggttt ccctctagaa ataattttgt ttaactttaa gaaggagata taccatgagc   180
ggatctggtg gcggatcagg cgg                                           203
```

<210> SEQ ID NO 63
<211> LENGTH: 203
<212> TYPE: DNA
<213> ORGANISM: Artificial
<220> FEATURE:
<223> OTHER INFORMATION: Fragment of pIE3a3AVk(E5)

<400> SEQUENCE: 63

```
atcgagatcc atagtagagt gcttctatca tagatcctcc gtttcgtgat gagtatagta    60
gagtgcttct atcatagatc ctccgtttcg tgatgagtat agtagagtgc ttctatcata   120
gatctcgatc ccgcgaaatt aatacgactc actataggga gaccacaacg gtttccctct   180
agaaataatt tgtttaact tta                                           203
```

<210> SEQ ID NO 64
<211> LENGTH: 203
<212> TYPE: DNA
<213> ORGANISM: Artificial
<220> FEATURE:
<223> OTHER INFORMATION: Fragment of pIE3a4AVk(E5)

<400> SEQUENCE: 64

```
atcgagatcc atagtagagt gcttctatca tagatcctcc gtttcgtgat gagtatagta    60
gagtgcttct atcatagatc ctccgtttcg tgatgagtat agtagagtgc ttctatcata   120
gatcctccgt ttcgtgatga gtatagtaga gtgcttctat catagatctc gatcccgcga   180
aattaatacg actcactata ggg                                           203
```

<210> SEQ ID NO 65
<211> LENGTH: 420
<212> TYPE: DNA
<213> ORGANISM: Artificial
<220> FEATURE:
<223> OTHER INFORMATION: scArc

<400> SEQUENCE: 65

```
agatctggtg gcggatcagg cggtggacat atgaaaggaa tgagcaaaat gccgcagttc    60
aatttgcggt ggcctagaga agtattggat ttggtacgca aggtagcgga agagaatggt   120
cggtctgtta attctgagat ttatcagcga gtaatggaaa gctttaagaa ggaagggcgc   180
attggcgccg gtggcggatc aggcggtgga tctggtggcg gatcaggcgg tggacatatg   240
aaaggaatga gcaaaatgcc gcagttcaat ttgcggtggc ctagagaagt attggatttg   300
gtacgcaagg tagcggaaga gaatggtcgg tctgttaatt ctgagattta tcagcgagta   360
atggaaagct ttaagaagga agggcgcatt ggcgccggtg gcggatcagg cggtggatcc   420
```

<210> SEQ ID NO 66
<211> LENGTH: 140
<212> TYPE: PRT
<213> ORGANISM: Artificial
<220> FEATURE:
<223> OTHER INFORMATION: scArc

<400> SEQUENCE: 66

Arg Ser Gly Gly Gly Ser Gly Gly Gly His Met Lys Gly Met Ser Lys

```
  1               5                   10                  15
Met Pro Gln Phe Asn Leu Arg Trp Pro Arg Glu Val Leu Asp Leu Val
            20                  25                  30

Arg Lys Val Ala Glu Glu Asn Gly Arg Ser Val Asn Ser Glu Ile Tyr
            35                  40                  45

Gln Arg Val Met Glu Ser Phe Lys Lys Glu Gly Arg Ile Gly Ala Gly
        50                  55                  60

Gly Gly Ser Gly Gly Gly Ser Gly Gly Gly Ser Gly Gly Gly His Met
65                  70                  75                  80

Lys Gly Met Ser Lys Met Pro Gln Phe Asn Leu Arg Trp Pro Arg Glu
                85                  90                  95

Val Leu Asp Leu Val Arg Lys Val Ala Glu Glu Asn Gly Arg Ser Val
            100                 105                 110

Asn Ser Glu Ile Tyr Gln Arg Val Met Glu Ser Phe Lys Lys Glu Gly
            115                 120                 125

Arg Ile Gly Ala Gly Gly Gly Ser Gly Gly Gly Ser
        130                 135                 140
```

<210> SEQ ID NO 67
<211> LENGTH: 701
<212> TYPE: DNA
<213> ORGANISM: Artificial
<220> FEATURE:
<223> OTHER INFORMATION: pIE2A

<400> SEQUENCE: 67

```
tcgagatctc gatcccgcga aattaatacg actcactata gggagaccac aacggtttcc      60
ctctagaaat aatttgttt aactttaaga aggagatata ccatggggtc gaccggcggc      120
gcggccgcag gatctggtgg cggatcaggc ggtggacata tgaaaggaat gagcaaaatg      180
ccgcagttca atttgcggtg gcctagagaa gtattggatt tggtacgcaa ggtagcggaa      240
gagaatggtc ggtctgttaa ttctgagatt tatcagcgag taatgaaaag ctttaagaag      300
gaagggcgca ttggcgccgg tggcggatca ggcggtggat ctggtggcgg atcaggcggt      360
ggacatatga aaggaatgag caaaatgccg cagttcaatt tgcggtggcc tagagaagta      420
ttggatttgg tacgcaaggt agcggaagag aatggtcggt ctgttaattc tgagatttat      480
cagcgagtaa tggaaagctt taagaaggaa gggcgcattg cgccggtgg cggatcaggc      540
ggtggatcct atccgtatga tgtgccggat tatgcgtaac tcgagagatc cggtaacaaa      600
gcccgaaagg aagctgagtt ggctgctgcc accgctgagc aataactagc ataacccctt      660
ggggcctcta acgggtctt gaggggtttt ttgctgaaag g                          701
```

<210> SEQ ID NO 68
<211> LENGTH: 158
<212> TYPE: PRT
<213> ORGANISM: Artificial
<220> FEATURE:
<223> OTHER INFORMATION: pIE2A

<400> SEQUENCE: 68

```
Met Gly Ser Thr Gly Gly Ala Ala Ala Gly Ser Gly Gly Gly Ser Gly
1               5                   10                  15

Gly Gly His Met Lys Gly Met Ser Lys Met Pro Gln Phe Asn Leu Arg
            20                  25                  30

Trp Pro Arg Glu Val Leu Asp Leu Val Arg Lys Val Ala Glu Glu Asn
            35                  40                  45

Gly Arg Ser Val Asn Ser Glu Ile Tyr Gln Arg Val Met Glu Ser Phe
```

```
                50                  55                  60
Lys Lys Glu Gly Arg Ile Gly Ala Gly Gly Ser Gly Gly Gly Ser
65                  70                  75                  80

Gly Gly Gly Ser Gly Gly His Met Lys Gly Met Ser Lys Met Pro
                85                  90                  95

Gln Phe Asn Leu Arg Trp Pro Arg Glu Val Leu Asp Leu Val Arg Lys
                100                 105                 110

Val Ala Glu Glu Asn Gly Arg Ser Val Asn Ser Glu Ile Tyr Gln Arg
                115                 120                 125

Val Met Glu Ser Phe Lys Lys Glu Gly Arg Ile Gly Ala Gly Gly
                130                 135                 140

Ser Gly Gly Gly Ser Tyr Pro Tyr Asp Val Pro Asp Tyr Ala
145                 150                 155

<210> SEQ ID NO 69
<211> LENGTH: 713
<212> TYPE: DNA
<213> ORGANISM: Artificial
<220> FEATURE:
<223> OTHER INFORMATION: pIE3A

<400> SEQUENCE: 69
tcgagatctc gatcccgcga aattaatacg actcactata gggagaccac aacggtttcc      60
ctctagaaat aattttgttt aactttaaga aggagatata ccatgagcgg atctggtggc     120
ggatcaggcg gtggacatat gaaaggaatg agcaaaatgc cgcagttcaa tttgcgtgg      180 cctagaaag tattggattt ggtacgcaag gtagcggaag agaatggtcg gtctgttaat      240
tctgagattt atcagcgagt aatgaaagc tttaagaagg aagggcgcat ggcgccggt      300 ggcggatcag gcggtggatc tggtggcgga tcaggcggtg acatatgaa aggaatgagc      360 aaaatgccgc agttcaattt gcggtggcct agagaagtat ggatttggt acgcaaggta      420 gcggaagaga atggtcggtc tgttaattct gagatttatc agcgagtaat ggaaagcttt      480
aagaaggaag gcgcattgg cgccggtggc ggatcaggcg gtggatccat ggggtcgacc      540
ggcggcgcgg ccgcaagatc ctatccgtat gatgtgccgg attatgcgta actcgagaga      600
tccggtaaca aagcccgaaa ggaagctgag ttggctgctg ccaccgctga gcaataacta      660
gcataacccc ttggggcctc taaacgggtc ttgagggtt ttttgctgaa agg             713

<210> SEQ ID NO 70
<211> LENGTH: 162
<212> TYPE: PRT
<213> ORGANISM: Artificial
<220> FEATURE:
<223> OTHER INFORMATION: pIE3A

<400> SEQUENCE: 70

Met Ser Gly Ser Gly Gly Gly Ser Gly Gly His Met Lys Gly Met
1               5                   10                  15

Ser Lys Met Pro Gln Phe Asn Leu Arg Trp Pro Arg Glu Val Leu Asp
                20                  25                  30

Leu Val Arg Lys Val Ala Glu Glu Asn Gly Arg Ser Val Asn Ser Glu
                35                  40                  45

Ile Tyr Gln Arg Val Met Glu Ser Phe Lys Lys Glu Gly Arg Ile Gly
                50                  55                  60

Ala Gly Gly Gly Ser Gly Gly Gly Ser Gly Gly Ser Gly Gly Gly
65                  70                  75                  80

His Met Lys Gly Met Ser Lys Met Pro Gln Phe Asn Leu Arg Trp Pro
```

Arg Glu Val Leu Asp Leu Val Arg Lys Val Ala Glu Glu Asn Gly Arg
         85                  90                  95
                    100                 105                 110

Ser Val Asn Ser Glu Ile Tyr Gln Arg Val Met Glu Ser Phe Lys Lys
            115                 120                 125

Glu Gly Arg Ile Gly Ala Gly Gly Ser Gly Gly Ser Met Gly
        130                 135                 140

Ser Thr Gly Gly Ala Ala Ala Arg Ser Tyr Pro Tyr Asp Val Pro Asp
145                 150                 155                 160

Tyr Ala

<210> SEQ ID NO 71
<211> LENGTH: 1047
<212> TYPE: DNA
<213> ORGANISM: Artificial
<220> FEATURE:
<223> OTHER INFORMATION: fragment of pIE2aAVk(E5)

<400> SEQUENCE: 71
atcgagatcc atagtagagt gcttctatca tagatctcga tcccgcgaaa ttaatacgac      60
tcactatagg gagaccacaa cggtttccct ctagaaataa ttttgtttaa ctttaagaag    120
gagatatacc atgggtcga cggacatcca gatgacccag tctccatcct ccctgtctgc    180
atctgtagga gacagagtca ccatcacttg ccgggcaagt cagagcgtta gcagctattt    240
aaattggtat cagcagaaac cagggaaagc ccctaagctc ctgatctatc ttgcatcccg    300
tttgcaaagt ggggtcccat caaggttcag tggcagtgga tctgggacag atttcactct    360
caccatcagc agtctgcaac ctgaagattt tgcaacttac tactgtcaac agaattggtg    420
gctgcctcct acgttcggcc aagggaccaa ggtggaaatc aaacgggcgg ccgcaggatc    480
tggtggcgga tcaggcggtg acatatgaa aggaatgagc aaaatgccgc agttcaattt    540
gcggtggcct agagaagtat tggatttggt acgcaaggta gcggaagaga atggtcggtc    600
tgttaattct gagatttatc agcgagtaat ggaaagcttt aagaaggaag gcgcattgg    660
cgccggtggc ggatcaggcg gtggatctgg tgcggatca gcggtggac atatgaaagg    720
aatgagcaaa atgccgcagt tcaatttgcg gtggcctaga gaagtattgg atttggtacg    780
caaggtagcg gaagagaatg gtcggtctgt taattctgag atttatcagc gagtaatgga    840
aagctttaag aaggaagggc gcattggcgc cggtggcgga tcaggcggtg gatcctatcc    900
gtatgatgtg ccggattatg cgtaactcga gagatccggt aacaaagccc gaaaggaagc    960
tgagttggct gctgccaccg ctgagcaata actagcataa ccccttgggg cctctaaacg   1020
ggtcttgagg gttttttgc tgaaagg                                       1047

<210> SEQ ID NO 72
<211> LENGTH: 264
<212> TYPE: PRT
<213> ORGANISM: Artificial
<220> FEATURE:
<223> OTHER INFORMATION: Fragment of pIE2aAVk(E5)

<400> SEQUENCE: 72

Met Gly Ser Thr Asp Ile Gln Met Thr Gln Ser Pro Ser Ser Leu Ser
1               5                   10                  15

Ala Ser Val Gly Asp Arg Val Thr Ile Thr Cys Arg Ala Ser Gln Ser
            20                  25                  30

Val Ser Ser Tyr Leu Asn Trp Tyr Gln Gln Lys Pro Gly Lys Ala Pro
        35                  40                  45

Lys Leu Leu Ile Tyr Leu Ala Ser Arg Leu Gln Ser Gly Val Pro Ser
            50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Trp
                85                  90                  95

Trp Leu Pro Pro Thr Phe Gly Gln Gly Thr Lys Val Glu Ile Lys Arg
            100                 105                 110

Ala Ala Ala Gly Ser Gly Gly Gly Ser Gly Gly Gly His Met Lys Gly
            115                 120                 125

Met Ser Lys Met Pro Gln Phe Asn Leu Arg Trp Pro Arg Glu Val Leu
            130                 135                 140

Asp Leu Val Arg Lys Val Ala Glu Glu Asn Gly Arg Ser Val Asn Ser
145                 150                 155                 160

Glu Ile Tyr Gln Arg Val Met Glu Ser Phe Lys Lys Glu Gly Arg Ile
                165                 170                 175

Gly Ala Gly Gly Gly Ser Gly Gly Gly Ser Gly Gly Gly Ser Gly Gly
            180                 185                 190

Gly His Met Lys Gly Met Ser Lys Met Pro Gln Phe Asn Leu Arg Trp
            195                 200                 205

Pro Arg Glu Val Leu Asp Leu Val Arg Lys Val Ala Glu Glu Asn Gly
            210                 215                 220

Arg Ser Val Asn Ser Glu Ile Tyr Gln Arg Val Met Glu Ser Phe Lys
225                 230                 235                 240

Lys Glu Gly Arg Ile Gly Ala Gly Gly Gly Ser Gly Gly Gly Ser Tyr
                245                 250                 255

Pro Tyr Asp Val Pro Asp Tyr Ala
            260

<210> SEQ ID NO 73
<211> LENGTH: 1058
<212> TYPE: DNA
<213> ORGANISM: Artificial
<220> FEATURE:
<223> OTHER INFORMATION: Fragment of pIE2aAVk(E5)

<400> SEQUENCE: 73
cgagatccat agtagagtgc ttctatcata gatctcgatc ccgcgaaatt aatacgactc     60
actataggga gaccacaacg gtttccctct agaaataatt ttgtttaact ttaagaagga    120
gatataccat gagcggatct ggtggcggat caggcggtgg acatatgaaa ggaatgagca    180
aaatgccgca gttcaatttg cggtggccta gagaagtatt ggatttggta cgcaaggtag    240
cggaagagaa tggtcggtct gttaattctg agatttatca gcgagtaatg gaaagcttta    300
agaaggaagg gcgcattggc gccggtggcg gatcaggcgg tggatctggt ggcggatcag    360
gcggtggaca tatgaaagga atgagcaaaa tgccgcagtt caatttgcgg tggcctagag    420
aagtattgga tttggtacgc aaggtagcgg aagagaatgg tcggtctgtt aattctgaga    480
tttatcagcg agtaatggaa agctttaaga aggaagggcg cattggcgcc ggtggcggat    540
caggcggtgg atccatgggg tcgacggaca tccagatgac ccagtctcca tcctccctgt    600
ctgcatctgt aggagacaga gtcaccatca cttgccgggc aagtcagagc gttagcagct    660
atttaaattg gtatcagcag aaaccaggga agcccctaa gctcctgatc tatcttgcat     720
cccgtttgca aagtggggtc ccatcaaggt tcagtggcag tggatctggg acagatttca    780
ctctcaccat cagcagtctg caacctgaag attttgcaac ttactactgt caacagaatt    840

```
ggtggctgcc tcctacgttc ggccaaggga ccaaggtgga aatcaaacgg gcggccgcaa      900
gatcctatcc gtatgatgtg ccggattatg cgtaactcga gagatccggt aacaaagccc      960
gaaaggaagc tgagttggct gctgccaccg ctgagcaata actagcataa ccccttgggg     1020
cctctaaacg ggtcttgagg ggttttttgc tgaaagga                              1058
```

<210> SEQ ID NO 74
<211> LENGTH: 268
<212> TYPE: PRT
<213> ORGANISM: Artificial
<220> FEATURE:
<223> OTHER INFORMATION: Fragment of pIE3aAVk(E5)

<400> SEQUENCE: 74

```
Met Ser Gly Ser Gly Gly Gly Ser Gly Gly Gly His Met Lys Gly Met
1               5                   10                  15

Ser Lys Met Pro Gln Phe Asn Leu Arg Trp Pro Arg Glu Val Leu Asp
            20                  25                  30

Leu Val Arg Lys Val Ala Glu Glu Asn Gly Arg Ser Val Asn Ser Glu
        35                  40                  45

Ile Tyr Gln Arg Val Met Glu Ser Phe Lys Lys Glu Gly Arg Ile Gly
    50                  55                  60

Ala Gly Gly Ser Gly Gly Gly Ser Gly Gly Gly Ser Gly Gly Gly
65                  70                  75                  80

His Met Lys Gly Met Ser Lys Met Pro Gln Phe Asn Leu Arg Trp Pro
                85                  90                  95

Arg Glu Val Leu Asp Leu Val Arg Lys Val Ala Glu Glu Asn Gly Arg
            100                 105                 110

Ser Val Asn Ser Glu Ile Tyr Gln Arg Val Met Glu Ser Phe Lys Lys
        115                 120                 125

Glu Gly Arg Ile Gly Ala Gly Gly Ser Gly Gly Gly Ser Met Gly
    130                 135                 140

Ser Thr Asp Ile Gln Met Thr Gln Ser Pro Ser Ser Leu Ser Ala Ser
145                 150                 155                 160

Val Gly Asp Arg Val Thr Ile Thr Cys Arg Ala Ser Gln Ser Val Ser
                165                 170                 175

Ser Tyr Leu Asn Trp Tyr Gln Gln Lys Pro Gly Lys Ala Pro Lys Leu
            180                 185                 190

Leu Ile Tyr Leu Ala Ser Arg Leu Gln Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys Gln Gln Asn Trp Trp Leu
225                 230                 235                 240

Pro Pro Thr Phe Gly Gln Gly Thr Lys Val Glu Ile Lys Arg Ala Ala
                245                 250                 255

Ala Arg Ser Tyr Pro Tyr Asp Val Pro Asp Tyr Ala
            260                 265
```

<210> SEQ ID NO 75
<211> LENGTH: 1077
<212> TYPE: DNA
<213> ORGANISM: Artificial
<220> FEATURE:
<223> OTHER INFORMATION: Fragment of pIE2aAVh(DOM1h-10-27)

<400> SEQUENCE: 75

```
atcgagatcc atagtagagt gcttctatca tagatctcga tcccgcgaaa ttaatacgac    60
tcactatagg gagaccacaa cggtttccct ctagaaataa ttttgtttaa ctttaagaag   120
gagatatacc atggccgagg tgcagctgtt ggagtctggg ggaggcttgg tacagcctgg   180
ggggtccctg cgtctctcct gtgcagcctc cggattcacc tttgagtggt attggatggg   240
ttgggtccgc caggctccag gaagggtct agagtgggtc tcagctatca gtggtagtgg   300
tggtagcaca tactacgcag actccgtgaa gggccggttc accatctccc gcgacaattc   360
caagaacacg ctgtatctgc aaatgaacag cctgcgtgcc gaggacgccg tatatatta   420
ctgtgcgaaa gttaagttgg ggggggggcc taatttttgc taccggggcc agggaaccct   480
ggtcaccgtc tcgagcgcgg ccgcaggatc tggtggcgga tcaggcggtg acatatgaa   540
aggaatgagc aaaatgccgc agttcaattt gcggtggcct agagaagtat tggatttggt   600
acgcaaggta gcggaagaga atggtcggtc tgttaattct gagatttatc agcgagtaat   660
ggaaagcttt aagaaggaag gcgcattgg cgccggtggc ggatcaggcg gtggatctgg   720
tggcggatca ggcggtggac atatgaaagg aatgagcaaa atgccgcagt tcaatttgcg   780
gtggcctaga gaagtattgg atttggtacg caaggtagcg gaagagaatg gtcggtctgt   840
taattctgag atttatcagc gagtaatgga aagctttaag aaggaaggc gcattggcgc   900
cggtggcgga tcaggcggtg gatcctatcc gtatgatgtg ccggattatg cgtaactcga   960
gagatccggt aacaaagccc gaaaggaagc tgagttggct gctgccaccg ctgagcaata  1020
actagcataa ccccttgggg cctctaaacg ggtcttgagg ggttttttgc tgaaagg     1077
```

<210> SEQ ID NO 76
<211> LENGTH: 274
<212> TYPE: PRT
<213> ORGANISM: Artificial
<220> FEATURE:
<223> OTHER INFORMATION: Fragment of pIE2aAVh(DOM1h-10-27)

<400> SEQUENCE: 76

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Glu
            20                  25                  30

Trp Tyr Trp Met Gly Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Ala Ala Val Tyr
                85                  90                  95

Tyr Cys Ala Lys Val Lys Leu Gly Gly Gly Pro Asn Phe Gly Tyr Arg
            100                 105                 110

Gly Gln Gly Thr Leu Val Thr Val Ser Ser Ala Ala Ala Gly Ser Gly
        115                 120                 125

Gly Gly Ser Gly Gly Gly His Met Lys Gly Met Ser Lys Met Pro Gln
    130                 135                 140

Phe Asn Leu Arg Trp Pro Arg Glu Val Leu Asp Leu Val Arg Lys Val
145                 150                 155                 160

Ala Glu Glu Asn Gly Arg Ser Val Asn Ser Glu Ile Tyr Gln Arg Val
                165                 170                 175

Met Glu Ser Phe Lys Lys Glu Gly Arg Ile Gly Ala Gly Gly Gly Ser
```

Gly Gly Gly Ser Gly Gly Gly Ser Gly Gly Gly His Met Lys Gly Met
            180                 185                 190

Ser Lys Met Pro Gln Phe Asn Leu Arg Trp Pro Arg Glu Val Leu Asp
        195                 200                 205

Leu Val Arg Lys Val Ala Glu Glu Asn Gly Arg Ser Val Asn Ser Glu
    210                 215                 220

Ile Tyr Gln Arg Val Met Glu Ser Phe Lys Lys Glu Gly Arg Ile Gly
225                 230                 235                 240

Ala Gly Gly Gly Ser Gly Gly Gly Ser Tyr Pro Tyr Asp Val Pro Asp
            245                 250                 255

Tyr Ala
        260                 265                 270

<210> SEQ ID NO 77
<211> LENGTH: 821
<212> TYPE: DNA
<213> ORGANISM: Artificial
<220> FEATURE:
<223> OTHER INFORMATION: Fragment of pIE7aA

<400> SEQUENCE: 77
catagatctc gatcccgcga aattaatacg actcactata gggagaccac aacggtttcc    60
ctctagaaat aattttgttt aactttaaga aggagatata ccatgggtc gaccggcggc   120
gcggccgcaa agaagcggc ggcgaaagaa gcggcggcga agaagcggc ggcgaaagaa   180
ttggccgcaa agaagcggc ggcgaaagaa gcggcggcga agaagcggc ggcgaaagaa   240
ttggccgcag atctggtgg cggatcaggc ggtggacata tgaaggaat gagcaaaatg   300
ccgcagttca atttgcggtg gcctagaaa gtattggatt tggtacgcaa ggtagcggaa   360
gagaatggtc ggtctgttaa ttctgagatt tatcagcgag taatggaaag ctttaagaag   420
gaagggcgca ttggcgccgg tggcggatca ggcggtggat ctggtggcgg atcaggcggt   480
ggacatatga aggaatgag caaaatgccg cagttcaatt tgcggtggcc tagagaagta   540
ttggatttgg tacgcaaggt agcggaagag aatggtcggt ctgttaattc tgagatttat   600
cagcgagtaa tggaaagctt taagaaggaa gggcgcattg gcgccggtgg cggatcaggc   660
ggtggatcct atccgtatga tgtgccggat tatgcgtaac tcgagagatc cggtaacaaa   720
gcccgaaagg aagctgagtt ggctgctgcc accgctgagc aataactagc ataacccctt   780
ggggcctcta acgggtcttg aggggttttt tgctgaaag g                        821

<210> SEQ ID NO 78
<211> LENGTH: 198
<212> TYPE: PRT
<213> ORGANISM: Artificial
<220> FEATURE:
<223> OTHER INFORMATION: Fragment of pIE7aA

<400> SEQUENCE: 78

Met Gly Ser Thr Gly Gly Ala Ala Ala Lys Glu Ala Ala Ala Lys Glu
1               5                   10                  15

Ala Ala Ala Lys Glu Ala Ala Ala Lys Glu Leu Ala Ala Lys Glu Ala
            20                  25                  30

Ala Ala Lys Glu Ala Ala Ala Lys Glu Ala Ala Ala Lys Glu Leu Ala
        35                  40                  45

Ala Gly Ser Gly Gly Gly Ser Gly Gly Gly His Met Lys Gly Met Ser
    50                  55                  60

Lys Met Pro Gln Phe Asn Leu Arg Trp Pro Arg Glu Val Leu Asp Leu

```
                65                  70                  75                  80
Val Arg Lys Val Ala Glu Glu Asn Gly Arg Ser Val Asn Ser Glu Ile
                    85                  90                  95

Tyr Gln Arg Val Met Glu Ser Phe Lys Lys Glu Gly Arg Ile Gly Ala
                100                 105                 110

Gly Gly Gly Ser Gly Gly Gly Ser Gly Gly Gly Ser Gly Gly Gly His
                115                 120                 125

Met Lys Gly Met Ser Lys Met Pro Gln Phe Asn Leu Arg Trp Pro Arg
    130                 135                 140

Glu Val Leu Asp Leu Val Arg Lys Val Ala Glu Glu Asn Gly Arg Ser
145                 150                 155                 160

Val Asn Ser Glu Ile Tyr Gln Arg Val Met Glu Ser Phe Lys Lys Glu
                165                 170                 175

Gly Arg Ile Gly Ala Gly Gly Gly Ser Gly Gly Gly Ser Tyr Pro Tyr
                180                 185                 190

Asp Val Pro Asp Tyr Ala
                195

<210> SEQ ID NO 79
<211> LENGTH: 108
<212> TYPE: PRT
<213> ORGANISM: Artificial
<220> FEATURE:
<223> OTHER INFORMATION: APS7

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Met Gly Tyr
                20                  25                  30

Leu Gln Trp Tyr Gln Gln Lys Pro Gly Lys Ala Pro Lys Leu Leu Ile
            35                  40                  45

Tyr Gly Gly Ser Asn Leu Gln Ser Gly Val Pro Ser Arg Phe Ser Gly
        50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Gln Gln Gln Ser Tyr Val Leu Pro Pro
                85                  90                  95

Thr Phe Gly Gln Gly Thr Lys Val Glu Ile Lys Arg
                100                 105

<210> SEQ ID NO 80
<211> LENGTH: 108
<212> TYPE: PRT
<213> ORGANISM: Artificial
<220> FEATURE:
<223> OTHER INFORMATION: APS3

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Met Gly Tyr
                20                  25                  30

Leu Gln Trp Tyr Gln Gln Lys Pro Gly Lys Ala Pro Lys Leu Leu Ile
            35                  40                  45

Tyr Gly Gly Ser Asn Leu Gln Ser Gly Val Pro Ser Arg Phe Ser Gly
        50                  55                  60

Ser Gly Ser Gly Thr Asp Phe Thr Leu Thr Ile Ser Asn Leu Gln Pro
```

Glu Asp Phe Ala Thr Tyr Tyr Gln Gln Ser Tyr Val Leu Pro Pro
65                  70                  75                  80

Thr Phe Gly Gln Gly Thr Arg Val Glu Ile Lys Arg
            85                  90                  95

100                 105

<210> SEQ ID NO 81
<211> LENGTH: 108
<212> TYPE: PRT
<213> ORGANISM: Artificial
<220> FEATURE:
<223> OTHER INFORMATION: APS11

<400> SEQUENCE: 81

Asp Ile Gln Met Thr Gln Ser Leu Ser Ser Leu Ser Ala Ser Val Gly
1               5                   10                  15

Asp Arg Val Thr Ile Thr Cys Arg Ala Ser Gln Trp Ile Met Gly Tyr
            20                  25                  30

Leu Gln Trp Tyr Gln Gln Lys Pro Gly Lys Ala Pro Lys Leu Leu Ile
        35                  40                  45

Tyr Gly Gly Ser Asn Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Gln Gln Ser Tyr Val Leu Pro Pro
                85                  90                  95

Thr Phe Gly Gln Gly Thr Lys Val Glu Ile Lys Arg
            100                 105

<210> SEQ ID NO 82
<211> LENGTH: 108
<212> TYPE: PRT
<213> ORGANISM: Artificial
<220> FEATURE:
<223> OTHER INFORMATION: APS8

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Gly Pro Tyr
            20                  25                  30

Leu Gln Trp Tyr Gln Gln Lys Pro Gly Lys Ala Pro Lys Leu Leu Ile
        35                  40                  45

Tyr Ser Ala Ser Val Leu Gln Ser Gly Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Gln Gln Gln Gly Ile Asn Pro Pro Arg
                85                  90                  95

Thr Phe Gly Gln Gly Thr Lys Val Glu Ile Lys Arg
            100                 105

<210> SEQ ID NO 83
<211> LENGTH: 108
<212> TYPE: PRT
<213> ORGANISM: Artificial
<220> FEATURE:
<223> OTHER INFORMATION: APS1

<400> SEQUENCE: 83

-continued

Asp Ile Gln Met Ala Gln Ser Pro Ser Ser Leu Ser Ala Ser Val Gly
1               5                   10                  15

Asp Arg Val Thr Ile Thr Cys Arg Ala Ser Gln Lys Ile Gly Pro Tyr
            20                  25                  30

Leu Gln Trp Tyr Gln Gln Lys Pro Gly Lys Ala Pro Lys Leu Leu Ile
        35                  40                  45

Tyr Ser Ala Ser Val Leu Gln Ser Gly Val Pro Ser Arg Phe Ser Gly
    50                  55                  60

Ser Gly Ser Gly Thr Val Phe Thr Leu Thr Val Ser Ser Leu Gln Pro
65                  70                  75                  80

Glu Asp Phe Ala Thr Tyr Tyr Gln Gln Gln Gly Ile Asn Pro Pro Arg
                85                  90                  95

Thr Phe Gly Gln Gly Thr Lys Val Glu Ile Lys Arg
            100                 105

<210> SEQ ID NO 84
<211> LENGTH: 108
<212> TYPE: PRT
<213> ORGANISM: Artificial
<220> FEATURE:
<223> OTHER INFORMATION: APS2

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Gly Pro Tyr
            20                  25                  30

Leu Gln Trp Tyr Gln Gln Lys Pro Gly Lys Ala Pro Arg Leu Leu Ile
        35                  40                  45

Tyr Ser Ala Ser Val Leu Gln Ser Gly Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Gln Gln Gln Gly Ile Asn Pro Pro Arg
                85                  90                  95

Thr Phe Gly Gln Gly Thr Lys Val Glu Ile Lys Arg
            100                 105

<210> SEQ ID NO 85
<211> LENGTH: 108
<212> TYPE: PRT
<213> ORGANISM: Artificial
<220> FEATURE:
<223> OTHER INFORMATION: APS6

<400> SEQUENCE: 85

Asp Ile Gln Met Ala Gln Ser Pro Ser Ser Leu Ser Ala Ser Val Gly
1               5                   10                  15

Asp Arg Val Thr Ile Thr Cys Arg Ala Ser Gln Lys Ile Gly Pro Tyr
            20                  25                  30

Leu Gln Trp Tyr Gln Gln Lys Pro Gly Lys Ala Pro Lys Leu Leu Ile
        35                  40                  45

Tyr Ser Ala Ser Val Ser Gln Ser Gly Val Pro Ser Arg Phe Ser Gly
    50                  55                  60

```
Ser Gly Ser Gly Thr Val Phe Thr Leu Thr Ile Ser Ser Leu Gln Pro
 65                  70                  75                  80

Glu Asp Ser Ala Thr Tyr Tyr Gln Gln Gln Gly Ile Asn Pro Pro Arg
                 85                  90                  95

Thr Phe Gly Gln Gly Thr Lys Val Glu Ile Lys Arg
            100                 105
```

<210> SEQ ID NO 86
<211> LENGTH: 108
<212> TYPE: PRT
<213> ORGANISM: Artificial
<220> FEATURE:
<223> OTHER INFORMATION: APS10

<400> SEQUENCE: 86

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Lys Ile Gly Pro Tyr
                 20                  25                  30

Leu Gln Trp Tyr Gln Gln Lys Pro Gly Lys Ala Pro Glu Leu Leu Ile
             35                  40                  45

Tyr Ser Ala Ser Val Leu Gln Ser Gly Val Pro Ser Arg Phe Ser Gly
 50                  55                  60

Ser Gly Ser Gly Thr Val Phe Thr Leu Thr Ile Ser Ser Leu Gln Pro
 65                  70                  75                  80

Glu Asp Phe Ala Thr Tyr Tyr Gln Gln Gln Gly Ile Asn Pro Pro Arg
                 85                  90                  95

Thr Leu Gly Gln Gly Thr Lys Val Glu Ile Lys Arg
            100                 105
```

<210> SEQ ID NO 87
<211> LENGTH: 107
<212> TYPE: PRT
<213> ORGANISM: Artificial
<220> FEATURE:
<223> OTHER INFORMATION: APS5

<400> SEQUENCE: 87

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Met Gly Tyr
                 20                  25                  30

Leu Gln Trp Tyr Gln Gln Lys Pro Gly Lys Ala Pro Lys Leu Leu Ile
             35                  40                  45

Tyr Gly Gly Ser Asn Leu Gln Ser Gly Val Pro Ser Arg Phe Ser Gly
 50                  55                  60

Ser Gly Ser Gly Thr Asp Phe Thr Leu Thr Ile Ser Asn Leu Gln Pro
 65                  70                  75                  80

Glu Asp Ser Ala Thr Tyr Tyr Gln Gln Ser Tyr Val Leu Pro Pro Thr
                 85                  90                  95

Phe Gly Gln Gly Thr Lys Val Glu Ile Lys Arg
            100                 105
```